(12) United States Patent
Bond et al.

(10) Patent No.: US 11,603,364 B2
(45) Date of Patent: Mar. 14, 2023

(54) ACYL HYDRAZONE DERIVATIVE COMPOUNDS FOR TREATING DISEASE

(71) Applicant: Alterity Therapeutics Limited, Melbourne (AU)

(72) Inventors: Silas Bond, Melbourne (AU); Penelope Jane Huggins, Melbourne (AU); Jack Gordon Parsons, Melbourne (AU)

(73) Assignee: Alterity Therapeutics Limited, Melbourne (AU)

( * ) Notice: Subject to any disclaimer, the term of this patent is extended or adjusted under 35 U.S.C. 154(b) by 0 days.

(21) Appl. No.: 17/459,854

(22) Filed: Aug. 27, 2021

(65) Prior Publication Data

US 2022/0064142 A1    Mar. 3, 2022

(30) Foreign Application Priority Data

Aug. 27, 2020 (AU) ................................. 2020903058

(51) Int. Cl.

| | |
|---|---|
| *C07D 401/12* | (2006.01) |
| *C07D 491/052* | (2006.01) |
| *C07D 417/12* | (2006.01) |
| *C07D 409/12* | (2006.01) |
| *C07D 495/04* | (2006.01) |
| *C07D 413/12* | (2006.01) |
| *C07D 405/12* | (2006.01) |
| *C07D 221/04* | (2006.01) |
| *C07D 239/26* | (2006.01) |
| *C07D 241/12* | (2006.01) |
| *C07D 213/53* | (2006.01) |
| *C07D 215/12* | (2006.01) |
| *C07D 277/28* | (2006.01) |
| *C07D 333/22* | (2006.01) |
| *C07D 277/64* | (2006.01) |
| *C07D 233/64* | (2006.01) |
| *C07D 471/04* | (2006.01) |
| *C07D 401/06* | (2006.01) |
| *C07D 413/14* | (2006.01) |
| *C07D 409/14* | (2006.01) |
| *C07D 417/14* | (2006.01) |
| *C07D 401/14* | (2006.01) |
| *C07D 405/14* | (2006.01) |
| *C07D 215/40* | (2006.01) |

(52) U.S. Cl.
CPC ......... *C07D 401/12* (2013.01); *C07D 213/53* (2013.01); *C07D 215/12* (2013.01); *C07D 215/40* (2013.01); *C07D 221/04* (2013.01); *C07D 233/64* (2013.01); *C07D 239/26* (2013.01); *C07D 241/12* (2013.01); *C07D 277/28* (2013.01); *C07D 277/64* (2013.01); *C07D 333/22* (2013.01); *C07D 401/06* (2013.01); *C07D 401/14* (2013.01); *C07D 405/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 471/04* (2013.01); *C07D 491/052* (2013.01); *C07D 495/04* (2013.01)

(58) Field of Classification Search
CPC .................................................... C07D 401/12
USPC ..................................................... 514/254.04
See application file for complete search history.

(56) References Cited

U.S. PATENT DOCUMENTS

| | | | | |
|---|---|---|---|---|
| 4,870,082 A | * | 9/1989 | Rector | .................. C07D 215/12 514/311 |
| 5,049,561 A | * | 9/1991 | Rector | .................. C07D 309/20 549/426 |
| 2002/0091148 A1 | | 7/2002 | BaMaung et al. | |
| 2010/0015140 A1 | | 1/2010 | Danter | |

FOREIGN PATENT DOCUMENTS

| | | |
|---|---|---|
| GB | 2325932 A | 12/1998 |
| WO | 8604582 A1 | 8/1986 |
| WO | 8706127 A1 | 10/1987 |
| WO | 0222576 A2 | 3/2002 |
| WO | 2012051708 A1 | 4/2012 |
| WO | 2019234728 A1 | 12/2019 |

(Continued)

OTHER PUBLICATIONS

CAPLUS 1956:89211.*
Australian Patent Office International-type search for Application No. 2020903058 dated Jun. 24, 2021 (31 pages). Bonnett et al., "A Target-Based Whole Cell Screen Approach To Identify Potential Inhibitors of *Mycobacterium tuberculosis* Signal Peptidase", ACS Infectious Diseases, 2016, vol. 2, pp. 893-902.

(Continued)

*Primary Examiner* — Kahsay Habte
(74) *Attorney, Agent, or Firm* — Michael Best & Friedrich LLP

(57) ABSTRACT

The present invention relates to compounds that have zinc and/or iron ionophore activity and their use in treating diseases that are modulated by reducing zinc and/or iron. In particular embodiments, the compounds are compounds of formula (I):

19 Claims, No Drawings

(56) References Cited

FOREIGN PATENT DOCUMENTS

WO  2020058062 A1  3/2020

OTHER PUBLICATIONS

Choudhary et al., "Dynamic Acylhydrazone Metal Ion Complex Libraries: A Mixed-Ligand Approach to Increased Selectivity in Extraction", Agnew. Chem. Int. Ed., 2002, vol. 41, No. 21, pp. 4096-4098.
El-Shorafa et al., "Syntheses, crystal structures, in vitro antitumor and free radical scavenging activity evaluation of a series of 2-substituted thiophenes", Med Chem Res, 2015, vol. 24, pp. 3021-3036.
Khidre et al., "Design, Synthesis, and Antimicrobial Evaluation of some Novel Pyridine, Coumarin, and Thiazole Derivatives", Journal of Heterocyclic Chemistry, vol. 54, 2017, pp. 2511-2519.
Tonkikh et al., "Synthesis and Reactions of 2-(4-Pyridyl)-7,7-Dimethyl-5-OXO-5,6,7,8,-Tetrahydroquinazoline", Chemistry of Heterocyclic Compounds, 1998, vol. 34, No. 1, pp. 92-95.
CAS Registry No. 1883230-00-9, accessed May 17, 2022, 2 pages.
CAS Registry No. 1865921-35-2, accessed May 17, 2022, 2 pages.
CAS Registry No. 1865897-72-8, accessed May 17, 2022, 2 pages.
CAS Registry No. 1865674-82-3, accessed May 17, 2022, 2 pages.
CAS Registry No. 1941939-85-0, accessed May 17, 2022, 2 pages.
Cukierman et al., "X1INH, an improved next-generation affinity-optimized hydrazonic ligand, attenuates abnormal copper(I)/copper(II)-α-Syn interactions and affects protein aggregation in a cellular model of synucleinopathy", Dalton Trans., 2020, 49, pp. 16252-16267.

\* cited by examiner

ACYL HYDRAZONE DERIVATIVE COMPOUNDS FOR TREATING DISEASE

CROSS-REFERENCE TO RELATED APPLICATIONS

This application claims priority to Australian Patent Application No. 2020903058, filed Aug. 27, 2020, the entire contents of which is hereby fully incorporated by reference.

FIELD OF THE INVENTION

The present invention relates to compounds that have zinc and/or iron ionophore activity and their use in treating diseases that are modulated by reducing zinc and/or iron.

BACKGROUND OF THE INVENTION

Zinc and iron are micronutrients involved in a number of biological processes including immune response, metabolism, nucleic acid synthesis and repair, apoptosis and redox homeostasis and can be important in host-pathogen interactions.

Zinc has been implicated in processes involved in diseases such as cancer and neurological diseases and has been shown to have antiviral, antibiotic and anti-infective activities.

Iron has been implicated in processes involved in neurodegenerative disorders and disorders associated with iron overload.

The ability to chelate zinc and/or iron and transport zinc and/or iron, for example, from the extracellular environment to the intracellular environment has utility in diverse disease processes. There is a need for further zinc and iron ionophores that may be useful in treating or managing disease processes.

SUMMARY OF THE INVENTION

Described herein are compounds of formula (I):

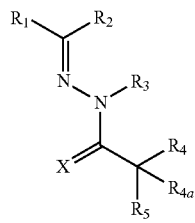

(I)

wherein X is O or S;
$R_1$ is selected from:

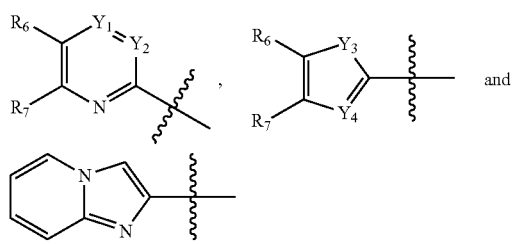
and wherein $Y_1$ is $CR_8$ or N;

$Y_2$ is $CR_8$ or N;

provided that both $Y_1$ and $Y_2$ are not N;

$Y_3$ is $C(R_8)_2$, $NR_9$ or S;

$Y_4$ is $CR_8$ or N;

provided that $Y_3$ is not $C(R_8)_2$ when $Y_4$ is $CR_8$;

$R_6$ and $R_7$ are independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, CN, $CO_2R_9$ and $N(R_9)_2$; or $R_6$ and $R_7$ taken together with the atoms to which they are attached form an optionally substituted 6 membered aryl or heteroaryl ring;

each $R_8$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, $(C(R_{10})_2)_mCO_2R_9$ and $(C(R_{10})_2)_mN(R_9)_2$;

each $R_9$ is independently selected from hydrogen, $C_{1-6}$alkyl, $C_{2-6}$alkenyl, $C_{2-6}$alkynyl and $C_{1-6}$haloalkyl;

$R_2$ is selected from hydrogen, $C_{1-6}$alkyl, $C_{2-6}$alkenyl, $C_{2-6}$alkynyl, $C_{1-6}$haloalkyl, $C_{3-8}$ cycloalkyl and

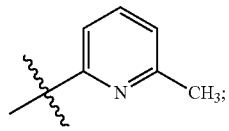 [SMILES: *c1cccc(C)n1]

$R_1$ and $R_2$ taken together for a 5, 6 or 7 membered cycloalkyl or heterocycloalkyl ring fused with a six-membered nitrogen-containing heteroaryl ring, wherein the cycloalkyl, heterocycloalkyl or heteroaryl ring may be optionally substituted, $R_3$ is selected from hydrogen, $C_{1-6}$alkyl, $C_{2-6}$alkenyl, $C_{2-6}$alkynyl and $(C(R_{10})_2)_mCO_2R_9$;

$R_4$ and $R_{4a}$ are each independently selected from hydrogen, $C_{1-6}$alkyl, $C_{2-6}$alkenyl, $C_{2-6}$alkynyl and $C_{1-6}$haloalkyl; and $R_5$ is hydrogen, $(C(R_{10})_2)_m$aryl or $(C(R_{10})_2)_m$heteroaryl wherein aryl and heteroaryl are optionally substituted; or $R_{4a}$ is CN and $R_4$ and $R_5$ taken together form:

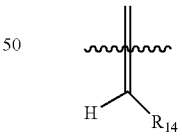

where $R_{14}$ is hydrogen, $(C(R_{10})_2)_m$aryl or $(C(R_{10})_2)_m$heteroaryl where aryl and heteroaryl are optionally substituted; or $R_{4a}$ is absent and $R_4$ and $R_5$ taken together form an optionally substituted aryl or optionally substituted heteroaryl group;

each $R_{10}$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, CN, halo and $N(R_9)_2$;

m is 0 or an integer of 1 to 6;

or a pharmaceutically acceptable salt thereof.

Also described herein are compounds of formula (Ia):

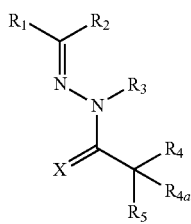

(Ia)

wherein X is O or S;
R$_1$ is selected from:

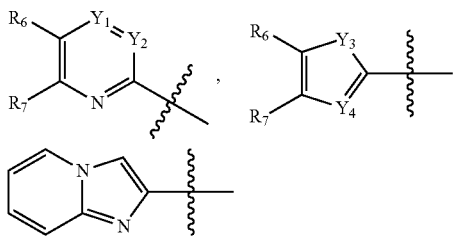

and

Y$_1$ is CR$_8$;
Y$_2$ is CR$_8$ or N;
Y$_3$ is C(R$_8$)$_2$, NR$_9$ or S;
Y$_4$ is CR$_8$ or N;
provided that Y$_3$ is C(R$_8$)$_2$ then Y$_4$ is not CR$_8$;
R$_6$ and R$_7$ are independently selected from hydrogen, C$_{1-6}$alkyl, C$_{2-6}$alkenyl, C$_{2-6}$alkynyl, hydroxy, C$_{1-6}$alkoxy, C$_{1-6}$haloalkyl, C$_{1-6}$haloalkoxy, halo, CN, C$_{O2}$R$_9$ and N(R$_9$)$_2$; or
R$_6$ and R$_7$ taken together with the atoms to which they are attached form an unsubstituted 6 membered aryl or heteroaryl ring;
each R$_8$ is independently selected from hydrogen, C$_{1-6}$alkyl, C$_{2-6}$alkenyl, C$_{2-6}$alkynyl, hydroxy, C$_{1-6}$alkoxy, C$_{1-6}$haloalkyl, C$_{1-6}$haloalkoxy, halo, (CH$_2$)$_m$CO$_2$R$_9$ and (CH$_2$)$_m$N(R$_9$)$_2$;
each R$_9$ is independently selected from hydrogen, C$_{1-6}$alkyl, C$_{2-6}$alkenyl, C$_{2-6}$alkynyl and C$_{1-6}$haloalkyl;
R$_2$ is selected from C$_{1-6}$alkyl, C$_{2-6}$alkenyl, C$_{2-6}$alkynyl, C$_{1-6}$haloalkyl, C$_{3-8}$ cycloalkyl and

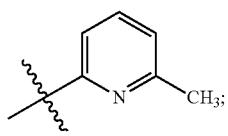 [SMILES: *c1cccc(C)n1]

R$_1$ and R$_2$ taken together for a 5, 6 or 7 membered cycloalkyl ring fused with a six membered nitrogen-containing heteroaryl ring, wherein the cycloalkyl or heteroaryl ring may be optionally substituted,
R$_3$ is selected from hydrogen, C$_{1-6}$alkyl, C$_{2-6}$alkenyl, C$_{2-6}$alkynyl and C(R$_{10}$)$_2$)$_m$CO$_2$R$_9$;
R$_4$ and R$_{4a}$ are each independently selected from hydrogen, C$_{1-6}$alkyl, C$_{2-6}$alkenyl, C$_{2-6}$alkynyl and C$_{1-6}$haloalkyl; and R$_5$ is (C(R$_{10}$)$_2$)$_m$aryl or (C(R$_{10}$)$_2$)$_m$heteroaryl where aryl and heteroaryl are optionally substituted; or R$_{4a}$ is CN and R$_4$ and R$_5$ taken together form:

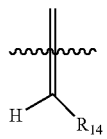

where R$_{14}$ is hydrogen, (C(R$_{10}$)$_2$)$_m$aryl or (C(R$_{10}$)$_2$)$_m$heteroaryl wherein aryl and heteroaryl are optionally substituted; or
R$_{4a}$ is absent and R$_4$ and R$_5$ taken together form an optionally substituted aryl or optionally substituted heteroaryl group;
each R$_{10}$ is independently selected from hydrogen, C$_{1-6}$alkyl, C$_{2-6}$alkenyl, C$_{2-6}$alkynyl, hydroxy, C$_{1-6}$alkoxy, C$_{1-6}$haloalkyl, C$_{1-6}$haloalkoxy, CN, halo and N(R$_9$)$_2$;
m is 0 or an integer of 1 to 6;
or a pharmaceutically acceptable salt thereof.

Also described herein are compounds of formula (Ib):

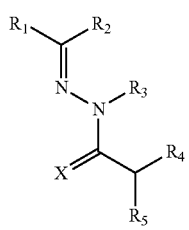

(Ib)

wherein X is O;
R$_1$ is selected from:

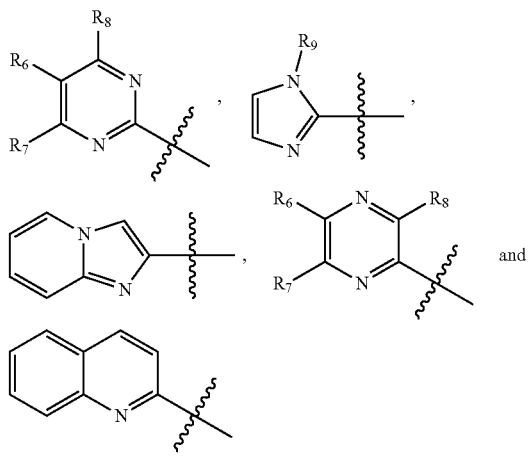

and

R$_6$ and R$_7$ are independently selected from hydrogen, C$_{1-6}$alkyl, C$_{2-6}$alkenyl, C$_{2-6}$alkynyl, hydroxy, C$_{1-6}$alkoxy, C$_{1-6}$haloalkyl, C$_{1-6}$haloalkoxy, halo, CN, C$_{O2}$R$_9$ and N(R$_9$)$_2$; or
R$_6$ and R$_7$ taken together with the atoms to which they are attached form an optionally substituted 6-membered aryl or heteroaryl ring;
each R$_8$ is independently selected from hydrogen, C$_{1-6}$alkyl, C$_{2-6}$alkenyl, C$_{2-6}$alkynyl, hydroxy, C$_{1-6}$alkoxy, C$_{1-6}$haloalkyl, C$_{1-6}$haloalkoxy, halo, (C(R$_{10}$)$_2$)$_m$CO$_2$R$_9$ and (C(R$_{10}$)$_2$)$_m$N(R$_9$)$_2$;

each $R_9$ is independently selected from hydrogen, $C_{1-6}$alkyl, $C_{2-6}$alkenyl, $C_{2-6}$alkynyl and $C_{1-6}$haloalkyl;

$R_2$ is selected from hydrogen, $C_{1-6}$alkyl, $C_{2-6}$alkenyl, $C_{2-6}$alkynyl, $C_{1-6}$haloalkyl, $C_{3-8}$ cycloalkyl and

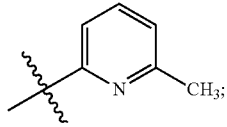 [SMILES: *c1cccc(C)n1]

$R_1$ and $R_2$ taken together form

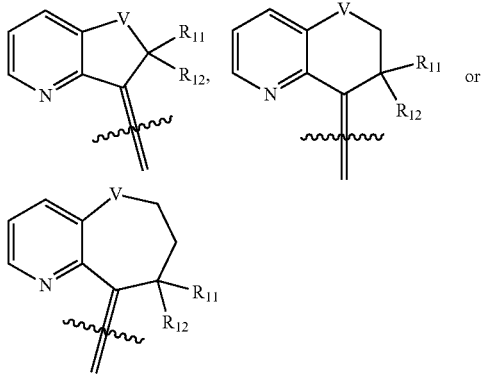

wherein V is CH, O or S and Rn and $R_{12}$ are each independently selected from hydrogen, $C_{1-6}$alkyl, $C_{2-6}$alkenyl, $C_{2-6}$alkynyl, halo, $C_{1-6}$haloalkyl, $(CH_2)_mC_{3-8}$cycloalkyl, $(CH_2)_m$aryl, $(CH_2)_m$heterocyclyl, $(CH_2)_m$heteroaryl and $COR_{13}$ where $R_{13}$ is selected from OH, $OC_{1-6}$alkyl, $OC_{2-6}$alkenyl, $OC_{2-6}$alkynyl and $N(R_9)_2$, wherein the cycloalkyl, heterocycloalkyl or heteroaryl ring of the bicyclic structure formed from $R_1$ and $R_2$ may be optionally substituted, or $R_1$ and $R_2$ are both:

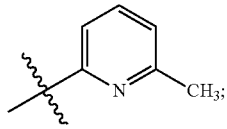 [SMILES: *c1cccc(C)n1]

$R_3$ is selected from hydrogen, $C_{1-6}$alkyl, $C_{2-6}$alkenyl, $C_{2-6}$alkynyl and $(C(R_{10})_2)_mCO_2R_9$; $R_4$ and $R_{4a}$ are each independently selected from hydrogen, $C_{1-6}$alkyl, $C_{2-6}$alkenyl, $C_{2-6}$alkynyl and $C_{1-6}$haloalkyl; and $R_5$ is hydrogen, $(C(R_{10})_2)_m$aryl, $(C(R_{10})_2)_m$heteroaryl, $O(C(R_{10})_2)_m$aryl or $O(C(R_{10})_2)_m$heteroaryl wherein the aryl and heteroaryl are optionally substituted; or $R_{4a}$ is CN and $R_4$ and $R_5$ are each hydrogen or are taken together form:

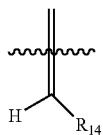

where $R_{14}$ is hydrogen, $(C(R_{10})_2)_m$aryl or $(C(R_{10})_2)_m$heteroaryl wherein the aryl and heteroaryl are optionally substituted; or $R_{4a}$ is absent and $R_4$ and $R_5$ taken together form an optionally substituted aryl or optionally substituted heteroaryl group;

each $R_{10}$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, CN, halo and $N(R_9)_2$;

m is 0 or an integer of 1 to 6;

or a pharmaceutically acceptable salt thereof.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

The term "haloalkyl" as used herein refers to an alkyl group as defined above where one or more hydrogen atoms have been replaced with a halogen atom and includes perhalogenated alkyl groups. Examples of suitable haloalkyl groups include fluoromethyl, difluoromethyl, trifluoromethyl, chloromethyl, dichloromethyl, trichloromethyl, chlorofluoromethyl, difluorochloromethyl, dichlorofluoromethyl, bromomethyl, iodomethyl, 1-fluoroethyl, 2-fluoroethyl, 1-chloroethyl, 2-chloroethyl, 1-bromoethyl, 2-bromoethyl, 1-iodoethyl, 2-iodoethyl, 1-fluoropropyl, 2-fluoropropyl, 3-fluoropropyl, 1-chloropropyl, 2-chloropropyl, 3-chloropropyl, and the like.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_{2-6}$ as in "C$_{2-6}$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, C$_{2-6}$ as in "C$_{2-6}$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 10 membered cycloalkyl group includes 3, 4, 5, 6, 7, 8, 9 or 10 carbon atoms. Examples of suitable cycloalkyl groups include, but are not limited to, cyclopropyl, cyclobutyl, cyclopentyl, cyclohexyl, cycloheptyl, cyclooctyl, cyclononyl and cyclodecyl.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "halogen" or "halo" refers to fluorine (fluoro), chlorine (chloro), bromine (bromo) and iodine (iodo).

As used herein, the terms "alkoxy" and "haloalkyloxy" refer to alkyl and haloalkyl groups defined above respectively when attached to an oxygen. Suitable examples include methoxy, ethoxy, n-propoxy, i-propoxy, n-butoxy, i-butoxy, t-butoxy, n-pentoxy, 2-methylbutoxy, 3-methylbutoxy, 4-methylbutoxy, n-hexoxy, 2-methylpentxoy, 3-methylpentoxy, 4-methylpentoxy, 5-methylpentoxy, 2-ethylbutoxy, 3-ethylbutoxy, fluoromethoxy, difluoromethoxy, trifluoromethoxy, chloromethoxy, dichloromethoxy, trichloromethoxy, chlorofluoromethoxy, difluorochloromethoxy, dichlorofluoromethoxy, bromomethoxy, iodomethoxy, 1-fluoroethoxy, 2-fluoroethoxy, 1-chloroethoxy, 2-chloroethoxy, 1-bromoethoxy, 2-bromoethoxy, 1-iodoethoxy, 2-iodoethoxy, 1-fluoropropoxy, 2-fluoropropoxy, 3-fluoropropoxy, 1-chloropropoxy, 2-chloropropoxy and 3-chloropropyl.

The term "heterocyclic" or "heterocyclyl" as used herein, refers to a cyclic hydrocarbon, such as a cycloalkyl group defined above, in which one to four carbon atoms have been replaced by heteroatoms independently selected from the group consisting of N, N(R), S, S(O), S(O)$_2$ and O. A heterocyclic ring may be saturated or unsaturated but not aromatic. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, 4H-thieno[3,2-c]chromene, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,2,3-thiadiazolyl, 1,3,5-triazinyl, 1,2,4-triazinyl, 1,2,4,5-tetrazinyl and tetrazolyl.

Each alkyl, alkenyl, alkynyl, cycloalkyl, aryl, heterocyclyl and heteroaryl whether an individual entity or as part of a larger entity may be optionally substituted with one or more optional substituents selected from the group consisting of C$_{1-6}$alkyl, C$_{2-6}$alkenyl, C$_{3-6}$cycloalkyl, oxo (=O), —OH, —SH, C$_{1-6}$alkylO—, C$_{2-6}$alkenylO—, C$_{3-6}$cycloalkylO—, C$_{1-6}$alkylS—, C$_{2-6}$alkenylS—, C$_{3-6}$cycloalkylS—, —CO$_2$H, —CO$_2$C$_{1-6}$alkyl, —OC(=O)C$_{1-6}$alkyl, —NH$_2$, —NH(C$_{1-6}$alkyl), —N(C$_{1-6}$alkyl)$_2$, —NH(phenyl), —N(phenyl)$_2$, —C$_{1-6}$alkylNH$_2$, —C$_{1-6}$alkylNH(C$_{1-6}$alkyl), —C$_{1-6}$alkylN(C$_{1-6}$alkyl)$_2$, —C$_{1-6}$alkylNH(phenyl), —C$_{1-6}$alkylN(phenyl)$_2$, —OC$_{1-6}$alkylNH$_2$, —OC$_{1-6}$alkylNH(C$_{1-6}$alkyl), —OC$_{1-6}$alkylN(C$_{1-6}$alkyl)$_2$, —OC$_{1-6}$alkylNH(phenyl), —OC$_{1-6}$alkylN(phenyl)$_2$, —CN, —NO2, -halogen, —CF$_3$, —OCF$_3$, —SCF$_3$, —CHF$_2$, —OCHF$_2$, —SCHF$_2$, -phenyl, -heterocyclyl, -heteroaryl, —Oheteroaryl, —Oheterocyclyl, —Ophenyl, —OC$_{1-6}$alkylheteroaryl, —OC$_{1-6}$alkylheterocyclyl, —OC$_{1-6}$alkylphenyl, —C(=O)phenyl, —C(=O)C$_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, oxo, hydroxymethyl, hydroxyethyl, hydroxypropyl, hydroxybutyl, fluoro, chloro, bromo, iodo, cyano, nitro, —CO$_2$H, —CO$_2$CH$_3$, —OC(=O)CH$_3$, trifluoromethyl, trifluoromethoxy, trifluoromethylthio, difluoromethyl, difluoromethoxy, difluoromethylthio, morpholino, amino, methylamino, dimethylamino, ethylamino, diethylamino, aminoC$_{1-6}$alkyl, methylaminoC$_{1-6}$alkyl, dimethylaminoC$_{1-6}$alkyl, ethylaminoC$_{1-6}$alkyl, diethylaminoC$_{1-6}$alkyl, aminoC$_{1-6}$alkoxy, methylaminoC$_{1-6}$alkoxy, dimethylaminoC$_{1-6}$alkoxy, ethylaminoC$_{1-6}$alkoxy, diethylaminoC$_{1-6}$alkoxy, phenyl, phenoxy, phenylcarbonyl, benzyl, phenylethoxy, phenylmethoxy, phenylpropoxy, pyrrolidinylmethoxy, pyrrolidinylethoxy, pyrrolidinylpropoxy, pyridinylmethoxy, pyridinylethoxy, pyridinylpropoxy and acetyl.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as formic, acetic, propionic, butyric, tartaric, maleic, hydroxymaleic, fumaric, citric, lactic, mucic, malonic, malic (L), lactic (DL), mandelic (DL), gluconic, carbonic, benzoic, succinic, oxalic, phenylacetic, methanesulphonic, ethanesulphonic, toluenesulphonic, camphorsulphonic, benezenesulphonic, salicylic, cinnamic, cyclamic, sulphanilic, aspartic, glutamic, glutaric, galactaric, gentisic, hippuric, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, aluminium, zinc, lysine, histidine, meglumine, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The compounds of the invention may also be in the form of solvates, including hydrates. The term "solvate" is used herein to refer to a complex of variable stoichiometry formed by a solute (a compound of formula (I)) and a solvent. Such solvents should not interfere with the biological activity of the solute. Solvents that may be included in a solvate include, but are not limited to, water, ethanol, propanol, and acetic acid. Methods of solvation are generally known within the art.

The term "pro-drug" is used in its broadest sense and encompasses those derivatives that are converted in vivo to the compounds of formula (I). Such derivatives would readily occur to those skilled in the art and include, for example, compounds where a free hydroxy group is converted into an ester derivative or a ring nitrogen is converted to an N-oxide. Examples of ester derivatives include alkyl esters, phosphate esters and those formed from amino acids. Conventional procedures for the preparation of suitable prodrugs are described in text books such as "Design of Prodrugs" Ed. H. Bundgaard, Elsevier, 1985.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

The compounds of the invention may also exist in the form of rotational isomers or conformers where there is restricted or hindered rotation about a single bond.

Any formula or structure given herein, including Formula (I) compounds are also intended to represent unlabelled forms as well as isotopically labelled forms of the compounds for use as medicaments or as a study tool. This may include metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labelled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{10}B$, $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labelled compounds of the present disclosure, for example those into which radioactive isotopes such as $^3H$, $^{13}C$ and $^{14}C$ are incorporated. In addition to use as pharmaceutical treatments, such isotopically labelled compounds may be useful.

Compounds of the Invention

The present invention provides metal ion modulating compounds, particularly zinc and iron selective ionophores. Such ionophores may have one or more of the desirable properties of: orally deliverable; low liver extraction, non-toxicity and the ability to modulate metals, particularly zinc and iron in biological systems. Advantageous metal selectivity, affinity and kinetic stability of the complexes formed may also be provided by particular compounds.

Described herein are compounds of formula (I):

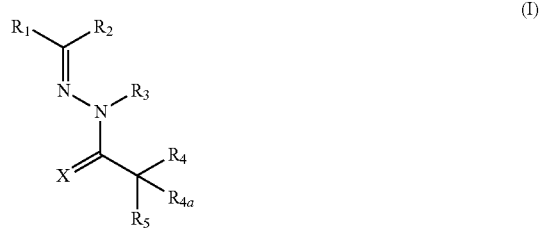

wherein X is O or S;

$R_1$ is selected from:

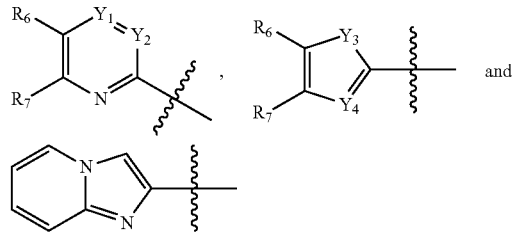

and $Y_1$ is $CR_8$ or N;

$Y_2$ is $CR_8$ or N;

provided that both $Y_1$ and $Y_2$ are not N;

$Y_3$ is $C(R_8)_2$, $NR_9$ or S;

$Y_4$ is $CR_8$ or N;

provided that $Y_3$ is not $C(R_8)_2$ when $Y_4$ is $CR_8$;

$R_6$ and $R_7$ are independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, CN, $CO_2R_9$ and $N(R_9)_2$; or $R_6$ and $R_7$ taken together with the atoms to which they are attached form an optionally substituted 6-membered aryl or heteroaryl ring;

each $R_8$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, $(C(R_{10})_2)_mCO_2R_9$ and $(C(R_{10})_2)_mN(R_9)_2$;

each $R_9$ is independently selected from hydrogen, $C_{1-6}$alkyl, $C_{2-6}$alkenyl, $C_{2-6}$alkynyl and $C_{1-6}$haloalkyl;

$R_2$ is selected from hydrogen, $C_{1-6}$alkyl, $C_{2-6}$alkenyl, $C_{2-6}$alkynyl, $C_{1-6}$haloalkyl, $C_{3-8}$ cycloalkyl and

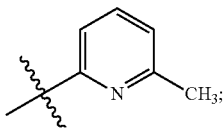 [SMILES: *c1cccc(C)n1]

or

R₁ and R₂ taken together for a 5, 6 or 7 membered cycloalkyl or heterocycloalkyl ring fused with a six membered nitrogen-containing heteroaryl ring, wherein the cycloalkyl, heterocycloalkyl or heteroaryl ring may be optionally substituted, R₃ is selected from hydrogen, $C_{1-6}$alkyl, $C_{2-6}$alkenyl, $C_{2-6}$alkynyl and $(C(R_{10})_2)_mCO_2R_9$;

R₄ and R₄ₐ are each independently selected from hydrogen, $C_{1-6}$alkyl, $C_{2-6}$alkenyl, $C_{2-6}$alkynyl and $C_{1-6}$haloalkyl; and R₅ is hydrogen, $(C(R_{10})_2)_m$aryl or $(C(R_{10})_2)_m$heteroaryl where aryl and heteroaryl are optionally substituted; or R₄ₐ is CN and R₄ and R₅ taken together form:

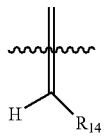

where R₁₄ is hydrogen, $(C(R_{10})_2)_m$aryl or $(C(R_{10})_2)_m$heteroaryl where aryl and heteroaryl are optionally substituted; or R₄ₐ is absent and R₄ and R₅ taken together form an optionally substituted aryl or optionally substituted heteroaryl group;

each R₁₀ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, CN, halo and $N(R_9)_2$;

m is 0 or an integer of 1 to 6;

or a pharmaceutically acceptable salt thereof.

In a particular embodiment, there is provided a compound of formula (Ib):

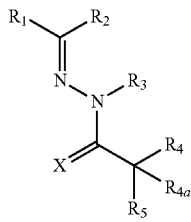

(Ib)

wherein X is O;
R₁ is selected from:

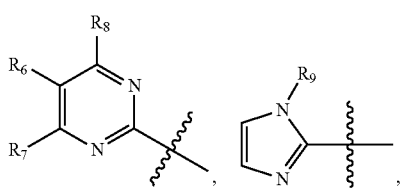

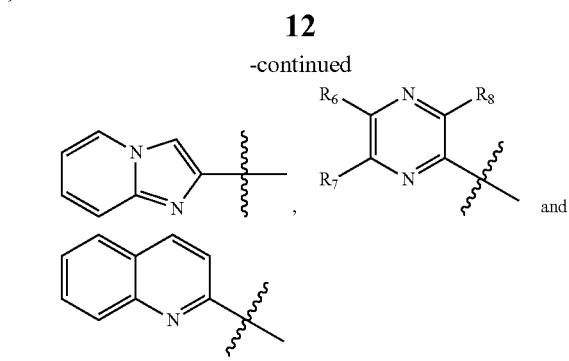

R₆ and R₇ are independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, CN, $CO_2R_9$ and $N(R_9)_2$; or R₆ and R₇ taken together with the atoms to which they are attached form an optionally substituted 6-membered aryl or heteroaryl ring;

each R₈ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, $(C(R_{10})_2)_mCO_2R_9$ and $(C(R_{10})_2)_mN(R_9)_2$;

each R₉ is independently selected from hydrogen, $C_{1-6}$alkyl, $C_{2-6}$alkenyl, $C_{2-6}$alkynyl and $C_{1-6}$haloalkyl;

R₂ is selected from hydrogen, $C_{1-6}$alkyl, $C_{2-6}$alkenyl, $C_{2-6}$alkynyl, $C_{1-6}$haloalkyl, $C_{3-8}$ cycloalkyl and

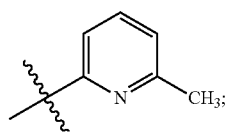 [SMILES: *c1cccc(C)n1]

R₁ and R₂ taken together form

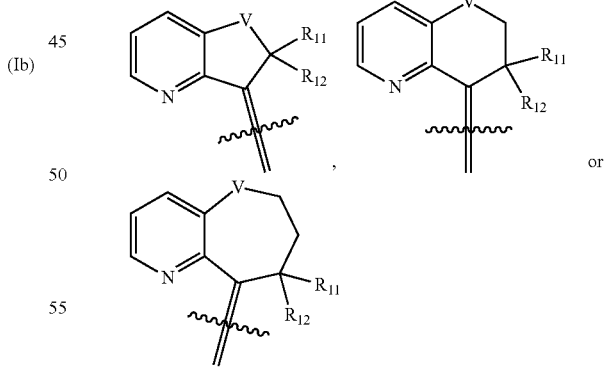

wherein V is CH, O or S and R₁₁ and R₁₂ are each independently selected from hydrogen, $C_{1-6}$alkyl, $C_{2-6}$alkenyl, $C_{2-6}$alkynyl, halo, $C_{1-6}$haloalkyl, $(CH_2)_mC_{3-8}$cycloalkyl, $(CH_2)_m$aryl, $(CH_2)_m$heterocyclyl, $(CH_2)_m$heteroaryl and $COR_{13}$ where R₁₃ is selected from OH, $OC_{1-6}$alkyl, $OC_{2-6}$alkenyl, $OC_{2-6}$alkynyl and $N(R_9)_2$, wherein the cycloalkyl, heterocycloalkyl or heteroaryl ring of the bicyclic structure formed from R₁ and R₂ may be optionally substituted, or $R_1$ and $R_2$ are both:

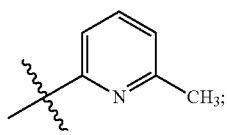 [SMILES: *c1cccc(C)n1]

$R_3$ is selected from hydrogen, $C_{1-6}$alkyl, $C_{2-6}$alkenyl, $C_{2-6}$alkynyl and $(C(R_{10})_2)_m CO_2 R_9$;

$R_4$ and $R_{4a}$ are each independently selected from hydrogen, $C_{1-6}$alkyl, $C_{2-6}$alkenyl, $C_{2-6}$alkynyl and $C_{1-6}$haloalkyl; and $R_5$ is hydrogen, $(C(R_{10})_2)_m$aryl, $(C(R_{10})_2)_m$heteroaryl, $O(C(R_{10})_2)_m$aryl or $O(C(R_{10})_2)_m$heteroaryl wherein the aryl and heteroaryl are optionally substituted; or $R_{4a}$ is CN and $R_4$ and $R_5$ are both hydrogen or taken together form:

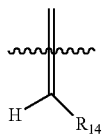

where $R_{14}$ is hydrogen, $(C(R_{10})_2)_m$aryl or $(C(R_{10})_2)_m$heteroaryl where in the aryl and heteroaryl are optionally substituted; or $R_{4a}$ is absent and $R_4$ and $R_5$ taken together form an optionally substituted aryl or optionally substituted heteroaryl group;

each $R_{10}$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, CN, halo and $N(R_9)_2$;

m is 0 or an integer of 1 to 6;

or a pharmaceutically acceptable salt thereof.

In particular embodiments of the compounds of formula (I), one or more of the following applies:

X is O;

$R_1$ is selected from:

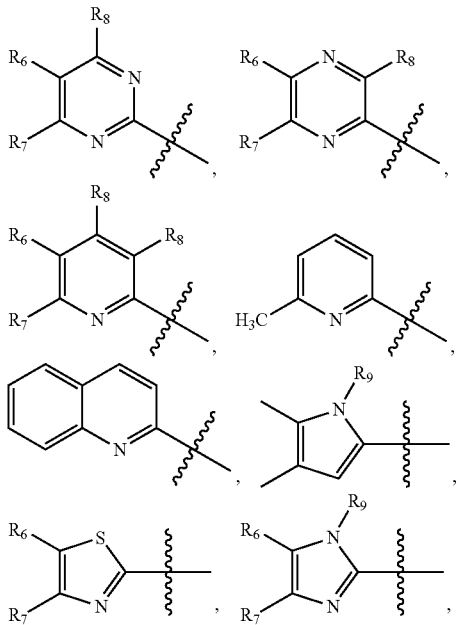

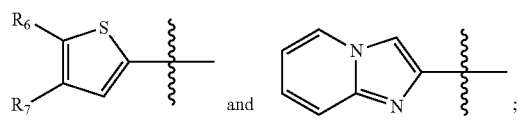

especially

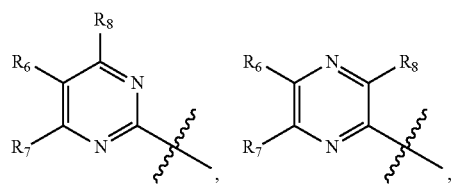

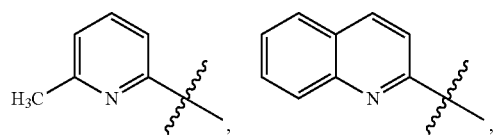

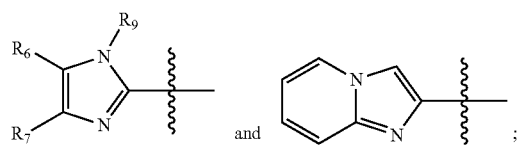

and more especially

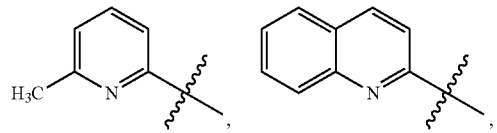

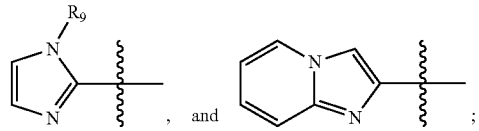

$R_2$ is selected from hydrogen, $C_{1-6}$alkyl, $C_{2-6}$alkenyl, $C_{2-6}$alkynyl, $C_{3-8}$ cycloalkyl and

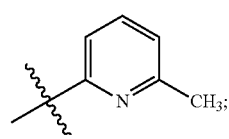 [SMILES: *c1cccc(C)n1]

especially

C$_{1-4}$alkyl, C$_{2-4}$alkenyl, C$_{2-4}$alkynyl, C$_{3-6}$ cycloalkyl and

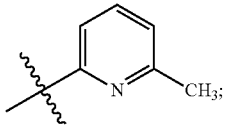 [SMILES: *c1cccc(C)n1]

more especially

C$_{1-4}$alkyl, C$_{3-6}$ cycloalkyl and

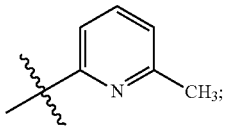

wherein when R$_1$ is

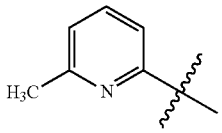 then R$_2$ is

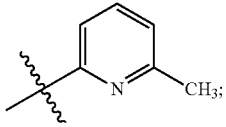 [SMILES: *c1cccc(C)n1]

especially where both R$_1$ and R$_2$ are

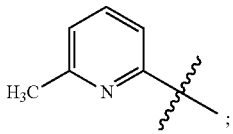 [SMILES: *c1cccc(C)n1];

R$_2$ may be hydrogen when R$_1$ is

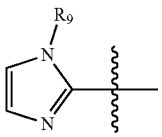, and 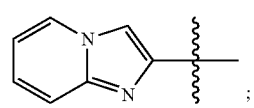;

R$_1$ and R$_2$ together form a 5 or 6 membered cycloalkyl or heterocycloalkyl ring fused with a six-membered nitrogen-containing heteroaryl ring, wherein the cycloalkyl and heteroaryl ring may be optionally substituted; especially where R$_1$ and R$_2$ together are selected from:

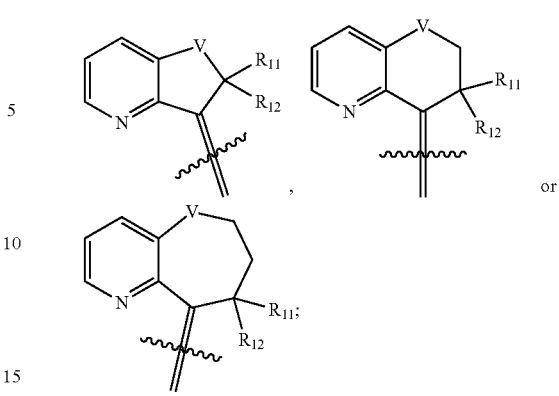,

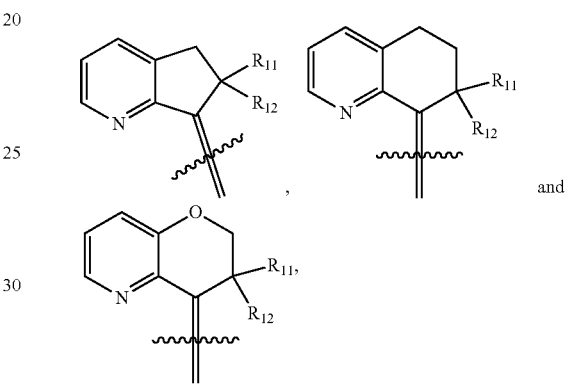

wherein V is CH, O or S, especially CH or O; especially wherein R$_{11}$ and R$_{12}$ are each independently selected from hydrogen, C$_{1-6}$alkyl, C$_{2-6}$alkenyl, C$_{2-6}$alkynyl, halo, C$_{1-6}$haloalkyl, (CH$_2$)$_m$C$_{3-8}$cycloalkyl, (CH$_2$)$_m$aryl, (CH$_2$)$_m$heterocyclyl, (CH$_2$)$_m$heteroaryl and COR$_{13}$ where R$_{13}$ is selected from OH, OC$_{1-6}$alkyl, OC$_{2-6}$alkenyl, OC$_{2-6}$alkynyl and N(R$_9$)$_2$, especially hydrogen, C$_{1-6}$alkyl and COR$_{13}$ where R$_{13}$ is selected from OC$_{1-6}$alkyl and N(R$_9$)$_2$, more especially hydrogen, C$_{1-3}$alkyl and COOC$_{1-3}$alkyl;

R$_3$ is selected from hydrogen, C$_{1-6}$alkyl, (CH$_2$)$_m$CO$_2$H and (CH$_2$)$_m$CO$_2$C$_{1-3}$alkyl, especially hydrogen, C$_{1-3}$alkyl, CH$_2$CO$_2$H and CH$_2$CO$_2$CH$_3$, more especially hydrogen; R$_4$ and R$_{4a}$ are each independently selected from hydrogen, C$_{1-3}$alkyl, C$_{2-3}$alkenyl, C$_{2-3}$alkynyl and C$_{1-3}$haloalkyl; and R$_5$ is hydrogen, (CH$_2$)$_m$aryl or (CH$_2$)$_m$heteroaryl where aryl and heteroaryl are optionally substituted; especially where R$_4$ and R$_{4a}$ are each independently hydrogen and R$_5$ is (CH$_2$)$_m$aryl, (CH$_2$)$_m$heteroaryl or Oaryl; where each aryl or heteroaryl ring are selected from phenyl, pyridinyl, indolyl, thiazolyl, oxazolyl, thiadiazolyl, benzothiophenyl and pyridizinyl, especially phenyl, indolyl and pyridinyl; and especially where each aryl or heteroaryl ring may be unsubstituted or substituted by one or more substituents selected from C$_{1-6}$alkyl, C$_{2-6}$alkenyl, C$_{2-6}$alkynyl, C$_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-}$ haloalkyl, N(C$_{1-3}$alkyl)$_2$ and O(CH$_2$)$_q$N(R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; or R$_{4a}$ is CN and R$_4$ and R$_5$ are each hydrogen or taken together form:

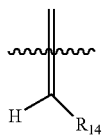

where R$_{14}$ is hydrogen, (CH$_2$)$_m$aryl or (CH$_2$)$_m$heteroaryl wherein the aryl and heteroaryl are optionally substituted; especially (CH$_2$)$_m$aryl or (CH$_2$)$_m$heteroaryl; wherein each aryl or heteroaryl ring may be unsubstituted or substituted by one or more substituents selected from C$_{1-6}$alkyl, C$_{2-6}$alkenyl, C$_{2-6}$alkynyl, C$_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$, (CH$_2$)$_q$N(R$_{15}$)$_2$ and O(CH$_2$)$_q$N(R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; or R$_{4a}$ is absent and R$_4$ and R$_5$ taken together form an optionally substituted aryl or optionally substituted heteroaryl group; especially where R$_4$ and R$_5$ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, -3-(1H)-indolyl ring or a or a 4H-thieno[3,2-c]chromene ring, especially a phenyl ring, a 2-pyridinyl ring, 3-pyridinyl ring, 4-pyridinyl ring, 3-pyridazinyl ring, 2-furanyl, 2-thiophenyl ring, 3-thiazolyl ring, 3-isoxazolyl ring, 5-(1,2,3-thiadiazolyl) ring, 5-thiadiazolyl ring, 2-benzo[b]thiophenyl ring, 3-(1H)-indolyl ring or a 4H-thieno[3,2-c]chromene ring, where each aryl or heteroaryl ring may be unsubstituted or substituted by one or more substituents selected from C$_{1-6}$alkyl, C$_{2-6}$alkenyl, C$_{2-6}$alkynyl, C$_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$ and O(CH$_2$)$_q$N (R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl;

R$_6$ and R$_7$ are independently selected from hydrogen, C$_{1-6}$alkyl, hydroxy, C$_{1-6}$alkoxy, C$_{1-6}$haloalkyl, C$_{1-6}$haloalkoxy, halo, CN, CO$_2$H, CO$_2$C$_{1-3}$alkyl and N(R$_9$)$_2$, especially hydrogen, C$_{1-3}$alkyl, hydroxy, C$_{1-3}$alkoxy, C$_{1-3}$haloalkyl, C$_{1-3}$haloalkoxy, halo, CN, CO$_2$H, CO$_2$CH$_3$ and N(C$_{1-3}$alkyl)$_2$, more especially hydrogen, methyl, ethyl, or CF$_3$, most especially hydrogen or methyl; or R$_6$ and R$_7$ taken together with the atoms to which they are attached form an optionally substituted phenyl, more especially an unsubstituted phenyl ring; each R$_8$ is independently selected from hydrogen, C$_{1-6}$alkyl, hydroxy, C$_{1-6}$alkoxy, C$_{1-6}$haloalkyl, C$_{1-6}$haloalkoxy, halo, (CH$_2$)$_{1-3}$CO$_2$H and (CH$_2$)$_{1-3}$N(R$_9$)$_2$, especially hydrogen, C$_{1-3}$alkyl, hydroxy, C$_{1-3}$alkoxy, C$_{1-3}$haloalkyl, C$_{1-3}$haloalkoxy, halo, CH$_2$CO$_2$H, CH$_2$CH$_2$CO$_2$H and N(C$_{1-3}$alkyl)$_2$, more especially hydrogen, methyl, ethyl, or CF$_3$, most especially hydrogen or methyl;

each R$_9$ is independently selected from hydrogen, C$_{1-6}$alkyl and C$_{1-6}$haloalkyl, especially hydrogen, C$_{1-6}$alkyl, more especially hydrogen, C$_{1-3}$alkyl, most especially hydrogen and methyl;

each R$_{10}$ is independently selected from hydrogen, C$_{1-6}$alkyl, hydroxy, C$_{1-6}$alkoxy, C$_{1-6}$haloalkyl, C$_{1-6}$haloalkoxy, CN, halo and N(R$_9$)$_2$, especially, hydrogen, C$_{1-3}$alkyl, hydroxy, C$_{1-3}$alkoxy, C$_{1-3}$haloalkyl, C$_{1-3}$haloalkoxy, CN, halo and N(C$_{1-3}$alkyl)$_2$, more especially hydrogen, methyl, ethyl, hydroxy, methoxy, ethoxy, trifluoromethyl, trifluoromethyloxy, fluoro and chloro;

m is 0 or an integer 1 to 3, especially where m is 0 or an integer 1 or 2.

In some embodiments, the compound of formula (I) is a compound of formula (II):

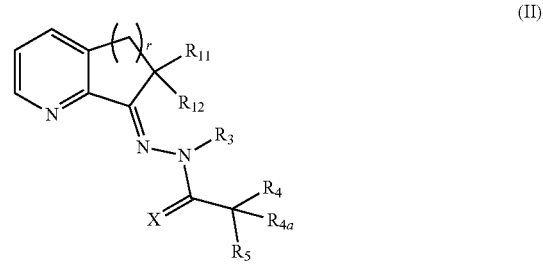

wherein X, R$_3$, R$_4$, R$_{4a}$ and R$_5$ are as defined for formula (I), R$_{11}$ and R$_{12}$ are each independently selected from hydrogen, C$_{1-6}$alkyl, C$_{2-6}$alkenyl, C$_{2-6}$alkynyl, halo, C$_{1-6}$haloalkyl, (CH$_2$)$_m$C$_{3-6}$ cycloalkyl, (CH$_2$)$_m$aryl, (CH$_2$)$_m$heterocyclyl, (CH$_2$)$_m$heteroaryl and COR$_{13}$ where R$_{13}$ is selected from OH, OC$_{1-6}$alkyl, OC$_{2-6}$alkenyl, OC$_{2-6}$alkynyl and N(R$_9$)$_2$ and r is 1, 2 or 3, or a pharmaceutically acceptable salt thereof.

In some embodiments, the compound of formula (II) is a compound of formula (IIa):

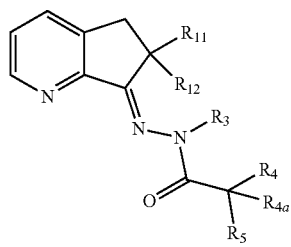

(IIa)

wherein R$_3$, R$_4$, R$_{4a}$, R$_5$, R$_{11}$ and R$_{12}$ are as defined for formula (II), or a pharmaceutically acceptable salt thereof.

In some embodiments, the compound of formula (II) is a compound of formula (IIb):

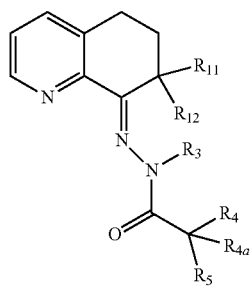

(IIb)

wherein R$_3$, R$_4$, R$_{4a}$, R$_5$, R$_{11}$ and R$_{12}$ are as defined for formula (II), or a pharmaceutically acceptable salt thereof.

In some embodiments, the compound of formula (II) is a compound of formula (IIc):

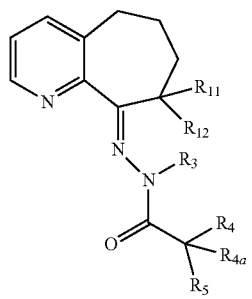

wherein R$_3$, R$_4$, R$_{4a}$, R$_5$, R$_{11}$ and R$_{12}$ are as defined for formula (II), or a pharmaceutically acceptable salt thereof.

In particular embodiments of the compounds of formula (II), one or more of the following applies:

X is O;

R$_3$ is selected from hydrogen, C$_{1-6}$alkyl, (CH$_2$)$_m$CO$_2$H and (CH$_2$)$_m$CO$_2$C$_{1-3}$alkyl, especially hydrogen, C$_{1-6}$alkyl, CH$_2$CO$_2$H and CH$_2$CO$_2$CH$_3$, more especially hydrogen; R$_4$ and R$_{4a}$ are each independently selected from hydrogen, C$_{1-3}$alkyl, C$_{2-3}$alkenyl, C$_{2-3}$alkynyl and C$_{1-3}$haloalkyl; and R$_5$ is hydrogen, (CH$_2$)$_m$aryl or (CH$_2$)$_m$heteroaryl where aryl and heteroaryl are optionally substituted; especially where R$_4$ and R$_{4a}$ are each independently hydrogen and R$_5$ is (CH$_2$)$_m$aryl, O(CH$_2$)$_m$aryl or (CH$_2$)$_m$heteroaryl; where each aryl or heteroaryl ring are selected from phenyl, pyridinyl, indolyl, thiazolyl, oxazolyl, thiadiazolyl, benzothiophenyl and pyridizinyl, especially phenyl, indolyl and pyridinyl; and especially where each aryl or heteroaryl ring may be unsubstituted or substituted by one or more substituents selected from C$_{1-6}$alkyl, C$_{2-6}$alkenyl, C$_{2-6}$alkynyl, C$_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$ and O(CH$_2$)$_q$N(R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; or R$_{4a}$ is CN and R$_4$ and R$_5$ are each hydrogen or taken together form:

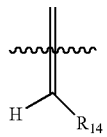

where R$_{14}$ is hydrogen, (CH$_2$)$_m$aryl or (CH$_2$)$_m$heteroaryl where aryl and heteroaryl are optionally substituted; especially (CH$_2$)$_m$aryl or (CH$_2$)$_m$heteroaryl; wherein each aryl or heteroaryl ring may be unsubstituted or substituted by one or more substituents selected from C$_{1-6}$alkyl, C$_{2-6}$alkenyl, C$_{2-6}$alkynyl, C$_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$, (CH$_2$)$_q$N(R$_{15}$)$_2$ and O(CH$_2$)$_q$N(R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; or R$_{4a}$ is absent and R$_4$ and R$_5$ taken together form an optionally substituted aryl or optionally substituted heteroaryl group; especially where R$_4$ and R$_5$ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, -3-(1H)-indolyl ring or a 4H-thieno[3,2-c] chromene ring, especially a phenyl ring, a 2-pyridinyl ring, 3-pyridinyl ring, 4-pyridinyl ring, 3-pyridazinyl ring, 2-furanyl, 2-thiophenyl ring, 3-thiazolyl ring, 3-isoxazolyl ring, 5-(1,2,3-thiadiazolyl) ring, 5-thiadiazolyl ring, 2-benzo[b]thiophenyl ring, 3-(1H)-indolyl ring or a 4H-thieno[3,2-c] chromene ring, where each aryl or heteroaryl ring may be unsubstituted or substituted by one or more substituents selected from C$_{1-6}$alkyl, C$_{2-6}$alkenyl, C$_{2-6}$alkynyl, C$_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$ and O(CH$_2$)$_q$N(R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; R$_{11}$ and R$_{12}$ are each independently selected from hydrogen, C$_{1-6}$alkyl, halo, C$_{1-6}$haloalkyl, (CH$_2$)$_m$C$_{3-8}$cycloalkyl, (CH$_2$)$_m$aryl, (CH$_2$)$_m$heterocyclyl, (CH$_2$)$_m$heteroaryl and COR$_{13}$ where R$_{13}$ is selected from OH, OC$_{1-6}$alkyl, and N(R$_9$)$_2$, especially where R$_{11}$ and R$_{12}$ are independently selected from hydrogen, C$_{1-6}$alkyl, C$_{1-6}$haloalkyl, C$_3$-8cycloalkyl, CH$_2$phenyl, CH$_2$pyridyl, and CO C$_{1-6}$alkyl, more especially where Rn and R$_{12}$ are independently selected from hydrogen, C$_{1-3}$alkyl, C$_{1-3}$haloalkyl, fluoro, C$_{3-6}$cycloalkyl, CH$_2$phenyl, CH$_2$pyridyl and COC$_{1-3}$alkyl, most especially where Rn and R$_{12}$ are both hydrogen, both methyl, both ethyl or where one of R$_{11}$ and R$_{12}$ is hydrogen and the other is methyl, ethyl, fluoro, CH$_2$phenyl, CH$_2$pyridyl, CO$_2$methyl or CO$_2$ethyl.

Particular compounds of formula II include compounds 1 to 42, 156 to 159 as set out in Tables 1 to 3 and compounds 145, 170, 179 and 180.

In some embodiments, the compound of formula (I) is a compound of formula (III):

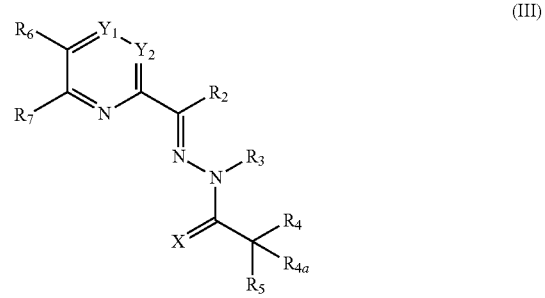

(III)

wherein X, Y$_1$, Y$_2$, R$_2$, R$_3$, R$_4$, R$_{4a}$, R$_5$, R$_6$ and R$_7$ are as defined for formula (I), or a pharmaceutically acceptable salt thereof.

In some embodiments, the compound of formula (III) is a compound of formula (IIIa):

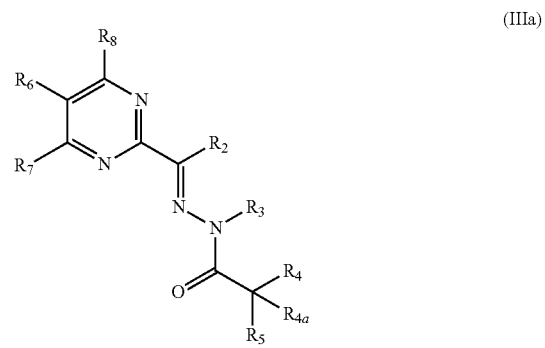

(IIIa)

wherein R$_2$, R$_3$, R$_4$, R$_{4a}$, R$_5$, R$_6$, R$_7$ and R$_8$ are as defined for formula (III), or a pharmaceutically acceptable salt thereof.

In some embodiments, the compound of formula (III) is a compound of formula (IIIb):

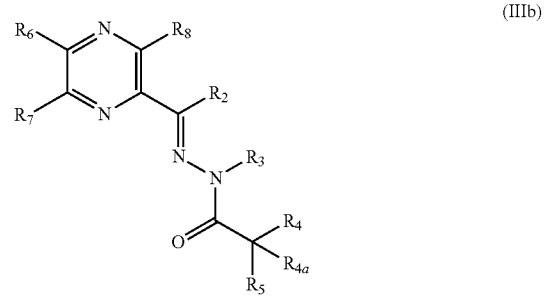

(IIIb)

wherein R$_2$, R$_3$, R$_4$, R$_{4a}$, R$_5$, R$_6$, R$_7$ and R$_8$ are as defined for formula (III), or a pharmaceutically acceptable salt thereof.

In some embodiments, the compound of formula (III) is a compound of formula (IIIc):

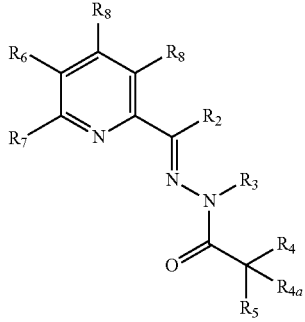
(IIIc)

wherein $R_2$, $R_3$, $R_4$, $R_{4a}$, $R_5$, $R_6$, $R_7$ and each $R_8$ are as defined for formula (III), or a pharmaceutically acceptable salt thereof.

In some embodiments, the compound of formula (III) is a compound of formula (IIId):

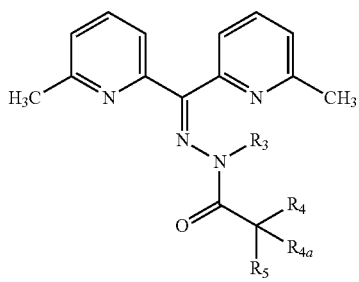
(IIId)

wherein $R_3$, $R_4$, $R_{4a}$ and $R_5$ are as defined for formula (III), or a pharmaceutically acceptable salt thereof.

In particular embodiments of the compounds of formula (III), one or more of the following applies:

X is O;

$R_1$ is selected from:

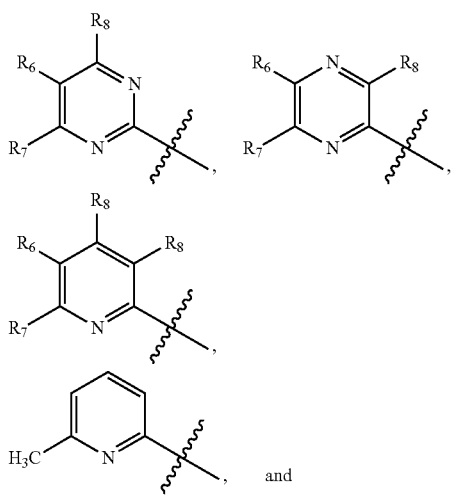

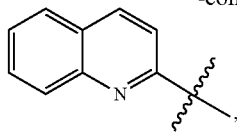, especially

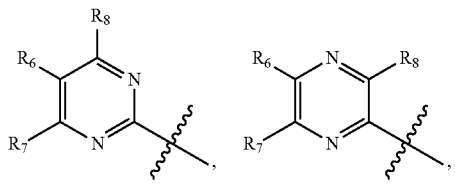,

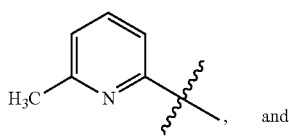, and

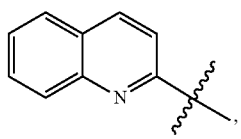,

More especially

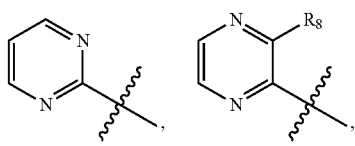,

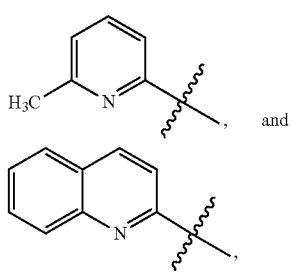, and $R_2$ is selected from hydrogen, $C_{1-6}$alkyl, $C_{2-6}$alkenyl, $C_{2-6}$alkynyl, $C_{3-8}$ cycloalkyl and

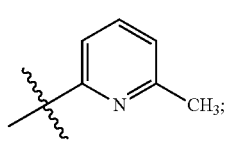 [SMILES: *c1cccc(C)n1];

especially
$C_{1-4}$alkyl, $C_{2-4}$alkenyl, $C_{2-4}$alkynyl, $C_{3-6}$ cycloalkyl and

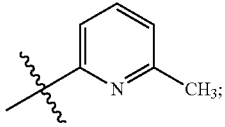 [SMILES: *c1cccc(C)n1]

more especially
$C_{1-4}$alkyl, $C_{3-6}$ cycloalkyl and

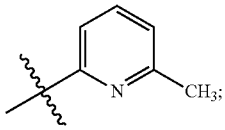 [SMILES: *c1cccc(C)n1]

wherein when $R_1$ is

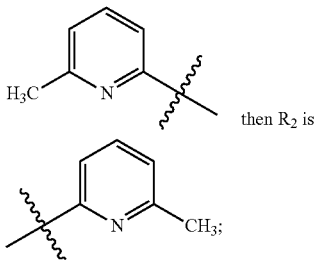

then $R_2$ is especially where both $R_1$ and $R_2$ are

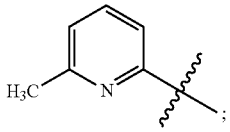 [SMILES: *c1cccc(C)n1]

$R_3$ is selected from hydrogen, $C_{1-6}$alkyl, $(CH_2)_mCO_2H$ and $(CH_2)_mCO_2C_{1-3}$alkyl, especially hydrogen, $C_{1-3}$alkyl, $CH_2CO_2H$ and $CH_2CO_2CH_3$, more especially hydrogen; $R_4$ and $R_{4a}$ are each independently selected from hydrogen, $C_{1-3}$alkyl, $C_{2-3}$alkenyl, $C_{2-3}$alkynyl and $C_{1-3}$haloalkyl; and $R_5$ is hydrogen, $(CH_2)_m$aryl or $(CH_2)_m$heteroaryl where aryl and heteroaryl are optionally substituted; especially where $R_4$ and $R_{4a}$ are each independently hydrogen and $R_5$ is $(CH_2)_m$aryl, $O(CH_2)_m$aryl or $(CH_2)_m$heteroaryl; wherein each aryl or heteroaryl ring are selected from phenyl, pyridinyl, indolyl, thiazolyl, oxazolyl, thiadiazolyl, benzothiophenyl and pyridizinyl, especially phenyl, indolyl and pyridinyl; and especially where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —$OC_{1-6}$alkyl, —$OC_{2-6}$alkenyl, —$OC_{2-6}$alkynyl, —$OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, —$OC_{1-3}$alkyl, —$OC_2$-3alkenyl, —$OC_{2-3}$alkynyl, —$OC_{1-3}$haloalkyl, $N(C_{1-3}$alkyl$)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —$OCH_2CH_2N(CH_3)_2$, —$OCH_2CH_2$piperidinyl, $OCH_2CH_2$pyrrolyl and —$OCH_2CH_2CH_2$piperidinyl; or $R_{4a}$ is CN and $R_4$ and $R_5$ are each hydrogen or taken together form:

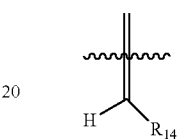

where $R_{14}$ is hydrogen, $(CH_2)_m$aryl or $(CH_2)_m$heteroaryl wherein the aryl and heteroaryl are optionally substituted; especially $(CH_2)_m$aryl or $(CH_2)_m$heteroaryl; wherein each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —$OC_{1-6}$alkyl, —$OC_{2-6}$alkenyl, —$OC_{2-6}$alkynyl, —$OC_{1-6}$haloalkyl, $N(R_9)_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, —$OC_{1-3}$alkyl, —$OC_{2-3}$alkenyl, —$OC_{2-3}$alkynyl, —$OC_{1-3}$haloalkyl, $N(C_{1-3}$alkyl$)_2$, $(CH_2)_qN(R_{15})_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —$OCH_2CH_2N(CH_3)_2$, —$OCH_2CH_2$piperidinyl, $OCH_2CH_2$pyrrolyl and —$OCH_2CH_2CH_2$piperidinyl; or $R_{4a}$ is absent and $R_4$ and $R_5$ taken together form an optionally substituted aryl or optionally substituted heteroaryl group; especially where $R_4$ and $R_5$ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, -3-(1H)-indolyl ring or a 4H-thieno[3,2-c] chromene ring, especially a phenyl ring, a 2-pyridinyl ring, 3-pyridinyl ring, 4-pyridinyl ring, 3-pyridazinyl ring, 2-furanyl, 2-thiophenyl ring, 3-thiazolyl ring, 3-isoxazolyl ring, 5-(1,2,3-thiadiazolyl) ring, 5-thiadiazolyl ring, 2-benzo[b]thiophenyl ring, 3-(1H)-indolyl ring or 4H-thieno[3,2-c] chromene ring, where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each R$_{15}$ is independently selected from hydrogen, C$_{1-6}$alkyl, C$_{2-6}$alkenyl, C$_{2-6}$alkynyl and C$_{1-6}$haloalkyl or two R$_{15}$ taken together with the nitrogen atom to which they are attached form a 5 or 6 membered heterocyclic ring, especially C$_{1-3}$alkyl, C$_{2-3}$alkenyl, C$_{2-3}$alkynyl, C$_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$ and O(CH$_2$)$_q$N(R$_{15}$)$_2$, wherein q is an integer from 1 to 3 and each R$_{15}$ is independently selected from hydrogen, C$_{1-3}$alkyl, C$_{2-3}$alkenyl, C$_{2-3}$alkynyl and C$_{1-3}$haloalkyl or two R$_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; R$_6$ and R$_7$ are independently selected from hydrogen, C$_{1-6}$alkyl, hydroxy, C$_{1-6}$alkoxy, C$_{1-6}$haloalkyl, C$_{1-6}$haloalkoxy, halo, CN, CO$_2$H, CO$_2$C$_{1-3}$alkyl and N(R$_9$)$_2$, especially hydrogen, C$_{1-3}$alkyl, hydroxy, C$_{1-3}$alkoxy, C$_{1-3}$haloalkyl, C$_{1-3}$haloalkoxy, halo, CN, CO$_2$H, CO$_2$CH$_3$ and N(C$_{1-3}$alkyl)$_2$, more especially hydrogen, methyl, ethyl, or CF$_3$, most especially hydrogen or methyl; or R$_6$ and R$_7$ taken together with the atoms to which they are attached form an optionally substituted phenyl, especially an unsubstituted or substituted phenyl ring, more especially an unsubstituted benzene ring;

each R$_8$ is independently selected from hydrogen, C$_{1-6}$alkyl, hydroxy, C$_{1-6}$alkoxy, C$_{1-6}$haloalkyl, C$_{1-6}$haloalkoxy, halo, (CH$_2$)$_{1-3}$CO$_2$H and (CH$_2$)$_{1-3}$N(R$_9$)$_2$, especially hydrogen, C$_{1-3}$alkyl, hydroxy, C$_{1-3}$alkoxy, C$_{1-3}$haloalkyl, C$_{1-3}$haloalkoxy, halo, CH$_2$CO$_2$H, CH$_2$CH$_2$CO$_2$H and N(C$_{1-3}$alkyl)$_2$, more especially hydrogen, methyl, ethyl, or CF$_3$, most especially hydrogen or methyl;

each R$_9$ is independently selected from hydrogen, C$_{1-6}$alkyl and C$_{1-6}$haloalkyl, especially hydrogen, C$_{1-6}$alkyl, more especially hydrogen, C$_{1-3}$alkyl, most especially hydrogen and methyl.

Particular compounds of formula III include compounds 44 to 92 and 160 to 169 as set out in Tables 5 and 6, compounds 122 to 137, 140 to 144, 154, 155 and 181 to 191 as set out in Table 8, compounds 192 to 196 from Table 9 and compounds 146 to 153 as set out in Example 10 and Tables 10 and 11, especially compounds 44 to 54, 56 to 62, 76 to 92, 122 to 137, 140 to 144, 154, 155, 160 to 169, 181 to 183 and 192 to 194.

In some embodiments, the compound of formula (I) is a compound of formula (IV):

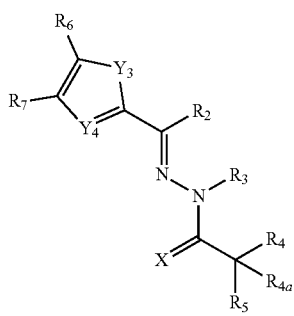

(IV)

wherein X, Y$_3$, Y$_4$, R$_2$, R$_3$, R$_4$, R$_{4a}$, R$_5$, R$_6$ and R$_7$ are as defined for formula (I), or a pharmaceutically acceptable salt thereof.

In some embodiments, the compound of formula (IV) is a compound of formula (IVa):

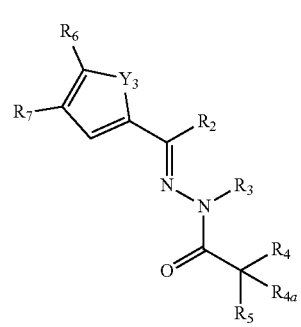

(IVa)

wherein R$_2$, R$_3$, R$_4$, R$_{4a}$, R$_5$, R$_6$, R$_7$ and R$_8$ are as defined for formula (IV) and Y$_3$ is S or NR$_9$, or a pharmaceutically acceptable salt thereof.

In some embodiments, the compound of formula (IV) is a compound of formula (IVb):

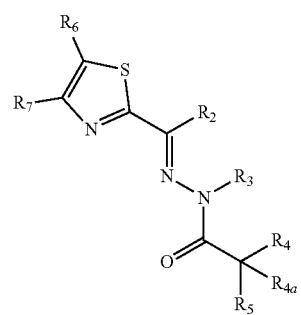

(IVb)

wherein R$_2$, R$_3$, R$_4$, R$_{4a}$, R$_5$, R$_6$ and R$_7$ are as defined for formula (IV), or a pharmaceutically acceptable salt thereof.

In some embodiments, the compound of formula (IV) is a compound of formula (IVc):

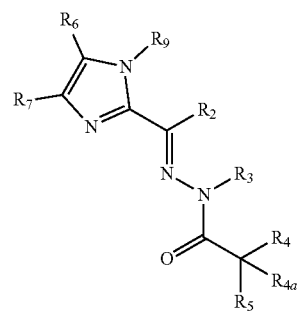

(IVc)

wherein R$_2$, R$_3$, R$_4$, R$_{4a}$, R$_5$, R$_6$, R$_7$ and R$_8$ are as defined for formula (IV), or a pharmaceutically acceptable salt thereof.

In particular embodiments of the compounds of formula (IV), one or more of the following applies:

X is O;

R₁ is selected from:

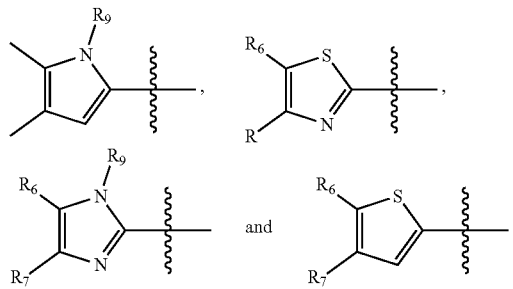

especially

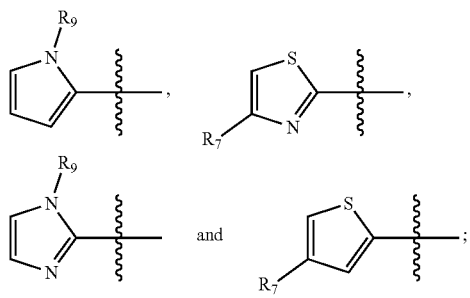

More especially

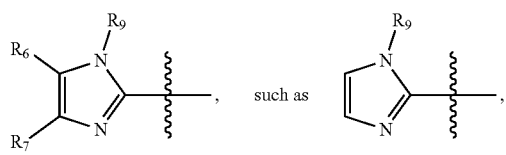 such as

R₂ is selected from hydrogen, $C_{1-6}$alkyl, $C_{2-6}$alkenyl, $C_{2-6}$alkynyl, and $C_{3-8}$ cycloalkyl, especially hydrogen, $C_{1-4}$alkyl, $C_{2-4}$alkenyl, $C_{2-4}$alkynyl and $C_{3-6}$ cycloalkyl, more especially hydrogen, $C_{1-4}$alkyl and $C_{3-6}$ cycloalkyl, R₃ is selected from hydrogen, $C_{1-6}$alkyl, $(CH_2)_mCO_2H$ and $(CH_2)_mCO_2C_{1-3}$alkyl, especially hydrogen, $C_{1-3}$alkyl, $CH_2CO_2H$ and $CH_2CO_2CH_3$, more especially hydrogen; R₄ and R₄ₐ are each independently selected from hydrogen, $C_{1-3}$alkyl, $C_{2-3}$alkenyl, $C_{2-3}$alkynyl and $C_{1-3}$haloalkyl; and R₅ is hydrogen, $(CH_2)_m$aryl, $O(CH_2)_m$aryl or $(CH_2)_m$heteroaryl where aryl and heteroaryl are optionally substituted; especially where R₄ and R₄ₐ are each independently hydrogen and R₅ is $(CH_2)_m$aryl or $(CH_2)_m$heteroaryl; where each aryl or heteroaryl ring are selected from phenyl, pyridinyl, indolyl, thiazolyl, oxazolyl, thiadiazolyl, benzothiophenyl and pyridizinyl, especially phenyl, indolyl and pyridinyl; and especially where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, $-OC_{1-6}$alkyl, $-OC_{2-6}$alkenyl, $-OC_{2-6}$alkynyl, $-OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, $-OC_{1-3}$alkyl, $-OC_{2-3}$alkenyl, $-OC_{2-3}$alkynyl, $-OC_{1-3}$haloalkyl, $N(C_{1-3}$alkyl$)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, $-OCH_2CH_2N(CH_3)_2$, $-OCH_2CH_2$piperidinyl, $OCH_2CH_2$pyrrolyl and $-OCH_2CH_2CH_2$piperidinyl; or R₄ₐ is CN and R₄ and R₅ are each hydrogen or taken together form:

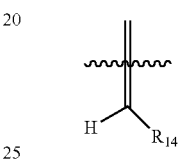

where $R_{14}$ is hydrogen, $(CH_2)_m$aryl or $(CH_2)_m$heteroaryl wherein the aryl and heteroaryl are optionally substituted; especially $(CH_2)_m$aryl or $(CH_2)_m$heteroaryl; wherein each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, $-OC_{1-6}$alkyl, $-OC_{2-6}$alkenyl, $-OC_{2-6}$alkynyl, $-OC_{1-6}$haloalkyl, $N(R_9)_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, $-OC_{1-3}$alkyl, $-OC_{2-3}$alkenyl, $-OC_{2-3}$alkynyl, $-OC_{1-3}$haloalkyl, $N(C_{1-3}$alkyl$)_2$, $(CH_2)_qN(R_{15})_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, $-OCH_2CH_2N(CH_3)_2$, $-OCH_2CH_2$piperidinyl, $OCH_2CH_2$pyrrolyl and $-OCH_2CH_2CH_2$piperidinyl; or R₄ₐ is absent and R₄ and R₅ taken together form an optionally substituted aryl or optionally substituted heteroaryl group; especially where R₄ and R₅ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, -3-(1H)-indolyl ring or 4H-thieno[3,2-c]chromene ring, especially a phenyl ring, a 2-pyridinyl ring, 3-pyridinyl ring, 4-pyridinyl ring, 3-pyridazinyl ring, 2-furanyl, 2-thiophenyl ring, 3-thiazolyl ring, 3-isoxazolyl ring, 5-(1,2,3-thiadiazolyl) ring, 5-thiadiazolyl ring, 2-benzo[b]thiophenyl ring, 3-(1H)-indolyl ring or a 4H-thieno[3,2-c]

chromene ring, where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —$OC_{1-6}$alkyl, —$OC_{2-6}$alkenyl, —$OC_{2-6}$alkynyl, —$OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, —$OC_{1-3}$alkyl, —$OC_{2-3}$alkenyl, —$OC_{2-3}$alkynyl, —$OC_{1-3}$haloalkyl, $N(C_{1-3}alkyl)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —$OCH_2CH_2N(CH_3)_2$, —$OCH_2CH_2$piperidinyl, $OCH_2CH_2$pyrrolyl and —$OCH_2CH_2CH_2$piperidinyl;

$R_6$ and $R_7$ are independently selected from hydrogen, $C_{1-6}$alkyl, hydroxy, $C_{1-6}$alkoxy, $C_{1-6}$haloalkyl, $C_{1-6}$haloalkoxy, halo, CN, $CO_2H$, $CO_2C_{1-3}$alkyl and $N(R_9)_2$, especially hydrogen, $C_{1-3}$alkyl, hydroxy, $C_{1-3}$alkoxy, $C_{1-3}$haloalkyl, $C_{1-3}$haloalkoxy, halo, CN, $CO_2H$, $CO_2CH_3$ and $N(C_{1-3}alkyl)_2$, more especially hydrogen, methyl, ethyl, or $CF_3$, most especially hydrogen or methyl; or $R_6$ and $R_7$ taken together with the atoms to which they are attached form an optionally substituted phenyl, especially an unsubstituted or substituted phenyl ring, more especially an unsubstituted benzene ring;

Each $R_8$ is independently selected from hydrogen, $C_{1-6}$alkyl, hydroxy, $C_{1-6}$alkoxy, $C_{1-6}$haloalkyl, $C_{1-6}$haloalkoxy, halo, $(CH_2)_{1-3}CO_2H$ and $(CH_2)_{1-3}N(R_9)_2$, especially hydrogen, $C_{1-3}$alkyl, hydroxy, $C_{1-3}$alkoxy, $C_{1-3}$haloalkyl, $C_{1-3}$haloalkoxy, halo, $CH_2CO_2H$, $CH_2CH_2CO_2H$ and $N(C_{1-3}alkyl)_2$, more especially hydrogen, methyl, ethyl, or $CF_3$, most especially hydrogen or methyl;

Each $R_9$ is independently selected from hydrogen, $C_{1-6}$alkyl and $C_{1-6}$haloalkyl, especially hydrogen, $C_{1-6}$alkyl, more especially hydrogen, $C_{1-3}$alkyl, most especially hydrogen and methyl.

Particular compounds of formula (IV) include compounds 93 to 119 and 163 to 169 as set out in Table 6 especially compounds 110 to 113, 116, 117 and 163 to 169.

In some embodiments, the compound of formula (I) is a compound of formula (V):

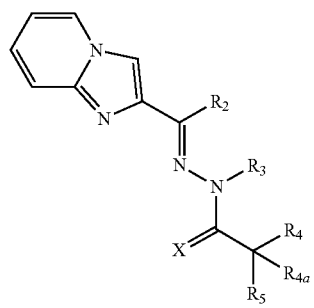

(V)

wherein $R_2$, $R_3$, $R_4$, $R_{4a}$ and $R_5$, are as defined for formula (I).

In particular embodiments of the compounds of formula (V), one or more of the following applies:

$R_2$ is selected from hydrogen, $C_{1-6}$alkyl, $C_{2-6}$alkenyl, $C_{2-6}$alkynyl, and $C_{3-8}$ cycloalkyl, especially hydrogen, $C_{1-4}$alkyl, $C_{2-4}$alkenyl, $C_{2-4}$alkynyl and $C_{3-6}$ cycloalkyl, more especially hydrogen, $C_{1-4}$alkyl and $C_{3-6}$ cycloalkyl, $R_3$ is selected from hydrogen, $C_{1-6}$alkyl, $(CH_2)_mCO_2H$ and $(CH_2)_mCO_2C_{1-3}$alkyl, especially hydrogen, $C_{1-3}$alkyl, $CH_2CO_2H$ and $CH_2CO_2CH_3$, more especially hydrogen;

$R_4$ and $R_{4a}$ are each independently selected from hydrogen, $C_{1-3}$alkyl, $C_{2-3}$alkenyl, $C_{2-3}$alkynyl and $C_{1-3}$haloalkyl; and $R_5$ is hydrogen, $(CH_2)_m$aryl, $O(CH_2)_m$aryl or $(CH_2)_m$heteroaryl where aryl and heteroaryl are optionally substituted; especially where $R_4$ and $R_{4a}$ are each independently hydrogen and $R_5$ is $(CH_2)_m$aryl or $(CH_2)_m$heteroaryl; where each aryl or heteroaryl ring are selected from phenyl, pyridinyl, indolyl, thiazolyl, oxazolyl, thiadiazolyl, benzothiophenyl and pyridazinyl, especially phenyl, indolyl and pyridinyl; and especially where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —$OC_{1-6}$alkyl, —$OC_{2-6}$alkenyl, —$OC_{2-6}$alkynyl, —$OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, —$OC_{1-3}$alkyl, —$OC_{2-3}$alkenyl, —$OC_2$-3alkynyl, —$OC_{1-3}$haloalkyl, $N(C_{1-3}alkyl)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —$OCH_2CH_2N(CH_3)_2$, —$OCH_2CH_2$piperidinyl, $OCH_2CH_2$pyrrolyl and —$OCH_2CH_2CH_2$piperidinyl; or $R_{4a}$ is CN and $R_4$ and $R_8$ are each hydrogen or taken together form:

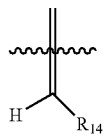

where $R_{14}$ is hydrogen, $(CH_2)_m$aryl or $(CH_2)_m$heteroaryl wherein the aryl and heteroaryl are optionally substituted; especially $(CH_2)_m$aryl or $(CH_2)_m$heteroaryl; where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —$OC_{1-6}$alkyl, —$OC_{2-6}$alkenyl, —$OC_{2-6}$alkynyl, —$OC_{1-6}$haloalkyl, $N(R_9)_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, —$OC_{1-3}$alkyl, —$OC_{2-3}$alkenyl, —$OC_2$-3alkynyl, —$OC_{1-3}$haloalkyl, $N(C_{1-3}alkyl)_2$, $(CH_2)_qN(R_{15})_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl; or $R_{4a}$ is absent and $R_4$ and $R_5$ taken together form an optionally substituted aryl or optionally substituted heteroaryl group; especially where $R_4$ and $R_5$ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, -3-(1H)-indolyl ring or a 4H-thieno[3,2-c]chromene ring, especially a phenyl ring, a 2-pyridinyl ring, 3-pyridinyl ring, 4-pyridinyl ring, 3-pyridazinyl ring, 2-furanyl, 2-thiophenyl ring, 3-thiazolyl ring, 3-isoxazolyl ring, 5-(1,2,3-thiadiazolyl) ring, 5-thiadiazolyl ring, 2-benzo[b]thiophenyl ring, 3-(1H)-indolyl ring or a 4H-thieno[3,2-c]chromene ring, where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, —OC$_{1-6}$alkyl, —OC$_{2-6}$alkenyl, —OC$_{2-6}$alkynyl, —OC$_{1-6}$haloalkyl, N(R$_9$)$_2$, (CH$_2$)$_q$N(R$_{15}$)$_2$ and O(CH$_2$)$_q$N(R$_{15}$)$_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, —OC$_{1-3}$alkyl, —OC$_{2-3}$alkenyl, —OC$_{2-3}$alkynyl, —OC$_{1-3}$haloalkyl, N(C$_{1-3}$alkyl)$_2$ and O(CH$_2$)$_q$N(R$_{15}$)$_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, —OCH$_2$CH$_2$N(CH$_3$)$_2$, —OCH$_2$CH$_2$piperidinyl, OCH$_2$CH$_2$pyrrolyl and —OCH$_2$CH$_2$CH$_2$piperidinyl;

Each $R_8$ is independently selected from hydrogen, $C_{1-6}$alkyl, hydroxy, $C_{1-6}$alkoxy, $C_{1-6}$haloalkyl, $C_{1-6}$haloalkoxy, halo, (CH$_2$)$_{1-3}$CO$_2$H and (CH$_2$)$_{1-3}$N(R$_9$)$_2$, especially hydrogen, $C_{1-3}$alkyl, hydroxy, $C_{1-3}$alkoxy, $C_{1-3}$haloalkyl, $C_{1-3}$haloalkoxy, halo, CH$_2$CO$_2$H, CH$_2$CH$_2$CO$_2$H and N(C$_{1-3}$alkyl)$_2$, more especially hydrogen, methyl, ethyl, or CF$_3$, most especially hydrogen or methyl;

Each $R_9$ is independently selected from hydrogen, $C_{1-6}$alkyl and $C_{1-6}$haloalkyl, especially hydrogen, $C_{1-6}$alkyl, more especially hydrogen, $C_{1-3}$alkyl, most especially hydrogen and methyl.

Particular compounds of formula V include compounds 120, 121, 138 and 139 as set out in Table 7.

In some embodiments, the compound of formula (I) is a compound of formula (VI):

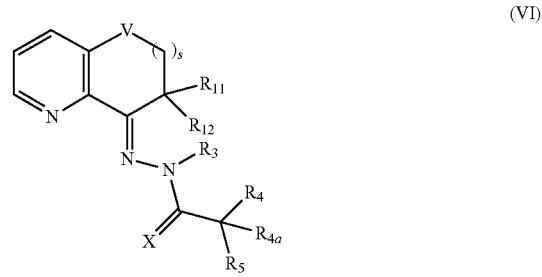

(VI)

wherein X, V, $R_3$, $R_4$, $R_{4a}$ and $R_5$ are as defined for formula (I), $R_{11}$ and $R_{12}$ are each independently selected from hydrogen, $C_{1-6}$alkyl, $C_{2-6}$alkenyl, $C_{2-6}$alkynyl, halo, $C_{1-6}$haloalkyl, (CH$_2$)$_m$C$_{3-6}$ cycloalkyl, (CH$_2$)$_m$aryl, (CH$_2$)$_m$heterocyclyl, (CH$_2$)$_m$heteroaryl and COR$_{13}$ where $R_{13}$ is selected from OH, OC$_{1-6}$alkyl, OC$_{2-6}$alkenyl, OC$_{2-6}$alkynyl and N(R$_9$)$_2$ and s is 0, 1 or 2, or a pharmaceutically acceptable salt thereof.

In some embodiments, the compound of formula (VI) is a compound of formula (VIa):

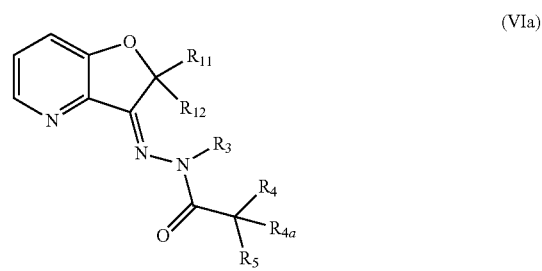

(VIa)

wherein $R_3$, $R_4$, $R_{4a}$, $R_5$, $R_{11}$ and $R_{12}$ are as defined for formula (VI), or a pharmaceutically acceptable salt thereof.

In some embodiments, the compound of formula (VI) is a compound of formula (VIb):

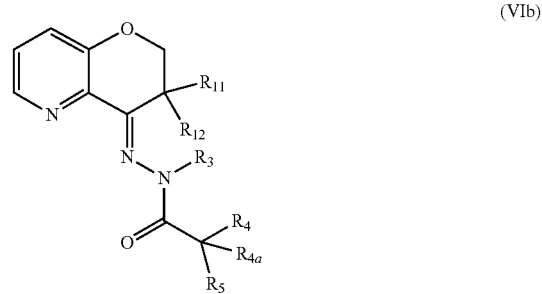

(VIb)

wherein $R_3$, $R_4$, $R_{4a}$, $R_5$, $R_{11}$ and $R_{12}$ are as defined for formula (VI), or a pharmaceutically acceptable salt thereof.

In some embodiments, the compound of formula (VI) is a compound of formula (VIc):

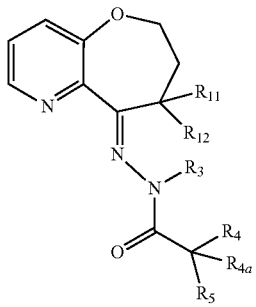

(VIc)

wherein $R_3$, $R_4$, $R_{4a}$, $R_5$, $R_{11}$ and $R_{12}$ are as defined for formula (VI) or a pharmaceutically acceptable salt thereof.

In particular embodiments of the compounds of formula (VI), one or more of the following applies:

X is O;

V is O;

$R_3$ is selected from hydrogen, $C_{1-6}$alkyl, $(CH_2)_mCO_2H$ and $(CH_2)_mCO_2C_{1-3}$alkyl, especially hydrogen, $C_{1-3}$alkyl, $CH_2CO_2H$ and $CH_2CO_2CH_3$, more especially hydrogen; $R_4$ and $R_{4a}$ are each independently selected from hydrogen, $C_{1-3}$alkyl, $C_{2-3}$alkenyl, $C_{2-3}$alkynyl and $C_{1-3}$haloalkyl; and $R_5$ is hydrogen, $(CH_2)_m$aryl, $O(CH_2)_m$aryl or $(CH_2)_m$heteroaryl where aryl and heteroaryl are optionally substituted; especially where $R_4$ and $R_{4a}$ are each independently hydrogen and $R_5$ is $(CH_2)_m$aryl or $(CH_2)_m$heteroaryl; where each aryl or heteroaryl ring are selected from phenyl, pyridinyl, indolyl, thiazolyl, oxazolyl, thiadiazolyl, benzothiophenyl and pyridizinyl, especially phenyl, indolyl and pyridinyl; and especially where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, $-OC_{1-6}$alkyl, $-OC_{2-6}$alkenyl, $-OC_{2-6}$alkynyl, $-OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, $-OC_{1-3}$alkyl, $-OC_{2-3}$alkenyl, $-OC_{2-3}$alkynyl, $-OC_{1-3}$haloalkyl, $N(C_{1-3}$alkyl$)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, $-OCH_2CH_2N(CH_3)_2$, $-OCH_2CH_2$piperidinyl, $OCH_2CH_2$pyrrolyl and $-OCH_2CH_2CH_2$piperidinyl; or $R_{4a}$ is CN and $R_4$ and $R_5$ are each hydrogen or taken together form:

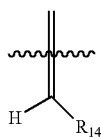

where $R_{14}$ is hydrogen, $(CH_2)_m$aryl or $(CH_2)_m$heteroaryl where aryl and heteroaryl are optionally substituted; especially $(CH_2)_m$aryl or $(CH_2)_m$heteroaryl; where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, $-OC_{1-6}$alkyl, $-OC_{2-6}$alkenyl, $-OC_{2-6}$alkynyl, $-OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, $-OC_{1-3}$alkyl, $-OC_{2-3}$alkenyl, $-OC_{2-3}$alkynyl, $-OC_{1-3}$haloalkyl, $N(C_{1-3}$alkyl$)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, $-OCH_2CH_2N(CH_3)_2$, $-OCH_2CH_2$piperidinyl, $OCH_2CH_2$pyrrolyl and $-OCH_2CH_2CH_2$piperidinyl; or $R_{4a}$ is absent and $R_4$ and $R_5$ taken together form an optionally substituted aryl or optionally substituted heteroaryl group; especially where $R_4$ and $R_5$ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, -3-(1H)-indolyl ring or a 4H-thieno[3,2-c]chromene ring, especially a phenyl ring, a 2-pyridinyl ring, 3-pyridinyl ring, 4-pyridinyl ring, 3-pyridazinyl ring, 2-furanyl, 2-thiophenyl ring, 3-thiazolyl ring, 3-isoxazolyl ring, 5-(1,2,3-thiadiazolyl) ring, 5-thiadiazolyl ring, 2-benzo[b]thiophenyl ring, 3-(1H)-indolyl ring or a 4H-thieno[3,2-c]chromene ring, where each aryl or heteroaryl ring may be unsubstituted or substituted by one or more substituents selected from $C_{1-6}$alkyl, $C_{2-6}$alkenyl, $C_{2-6}$alkynyl, $C_{1-6}$haloalkyl, halo, hydroxy, $-OC_{1-6}$alkyl, $-OC_{2-6}$alkenyl, $-OC_{2-6}$alkynyl, $-OC_{1-6}$haloalkyl, $N(R_9)_2$, $(CH_2)_qN(R_{15})_2$ and $O(CH_2)_qN(R_{15})_2$, wherein q is an integer of 1 to 6 and each $R_{15}$ is independently selected from hydrogen, $C_{1-6}$alkyl, $C_{2-6}$alkenyl, $C_{2-6}$alkynyl and $C_{1-6}$haloalkyl or two $R_{15}$ taken together with the nitrogen atom to which they are attached form a 5 or 6 membered heterocyclic ring, especially $C_{1-3}$alkyl, $C_{2-3}$alkenyl, $C_{2-3}$alkynyl, $C_{1-3}$haloalkyl, halo, hydroxy, $-OC_{1-3}$alkyl, $-OC_{2-3}$alkenyl, $-OC_{2-3}$alkynyl, $-OC_{1-3}$haloalkyl, $N(C_{1-3}$alkyl$)_2$ and $O(CH_2)_qN(R_{15})_2$, wherein q is an integer from 1 to 3 and each $R_{15}$ is independently selected from hydrogen, $C_{1-3}$alkyl, $C_{2-3}$alkenyl, $C_{2-3}$alkynyl and $C_{1-3}$haloalkyl or two $R_{15}$ taken together with the nitrogen atom to which they are attached form a 5 or 6 membered heterocyclic ring, more especially methyl, ethyl, propyl, isopropyl, chloro, fluoro, trifluoromethyl, methoxy, ethoxy, dimethyl amino, diethyl amino, $-OCH_2CH_2N(CH_3)_2$, $-OCH_2CH_2$piperidinyl, $OCH_2CH_2$pyrrolyl and $-OCH_2CH_2CH_2$piperidinyl;

$R_{11}$ and $R_{12}$ are each independently selected from hydrogen, $C_{1-6}$alkyl, halo, $C_{1-6}$haloalkyl, $(CH_2)_mC_{3-8}$cycloalkyl, $(CH_2)_m$aryl, $(CH_2)_m$heterocyclyl, $(CH_2)_m$heteroaryl and $COR_{13}$ where $R_{13}$ is selected from OH, $OC_{1-6}$alkyl, and $N(R_9)_2$, especially where $R_{11}$ and $R_{12}$ are independently selected from hydrogen, $C_{1-6}$alkyl, $C_{1-6}$haloalkyl, $C_{3-8}$cycloalkyl, $CH_2$phenyl, $CH_2$pyridyl, and CO $C_{1-6}$alkyl, more especially where Rn and $R_{12}$ are independently selected from hydrogen, $C_{1-3}$alkyl, $C_{1-3}$haloalkyl, fluoro, $C_{3-6}$cycloalkyl, $CH_2$phenyl, $CH_2$pyridyl and $COC_{1-3}$alkyl, most especially where Rn and $R_{12}$ are both hydrogen, both methyl, both ethyl or where one of $R_{11}$ and $R_{12}$ is hydrogen and the other is methyl, ethyl, fluoro, $CH_2$phenyl, $CH_2$pyridyl, $CO_2$methyl or $CO_2$ethyl.

Particular compounds of formula VI include compounds 171 to 178 in Table 12.

The compounds of the invention may be synthesised from commercially available starting materials using known methods. For example, the hydrazides may be prepared by reacting an appropriate ketone with a carboxylic acid hydrazine in the presence of a catalytic amount of acid.

hydrazone products B. Ketone starting materials were available from commercial suppliers or known literature methods. For example, 5,6-dihydro-7,7-dimethylquinolin-8-one could be prepared, as described by Chuang Bing et al, *New Journal of Chemistry* 2016, 40, 9329-9346. Ethyl 8-oxo-5,6,7,8-tetrahydroquinoline-7-carboxylate starting material is known in the literature (Takashi et al, *Synthesis* 2005, 10, 1593-1600). The compound could be synthesised by heating 6,7-dihydroquinolin-8(5H)-one, sodium hydride and diethyl carbonate at 130° C.

Scheme 1

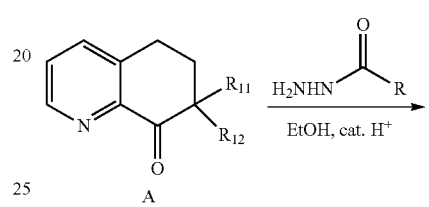

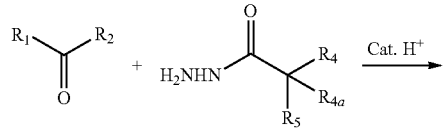

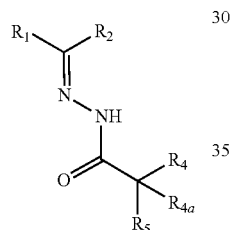

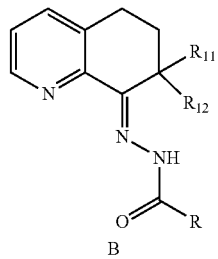

Suitable catalytic acids include concentrated hydrochloric acid or toluene sulphonic acid.

The resulting hydrazides may be further derivatised, for example by alkylation of hydroxy groups or formation of double bonds from ketones and aldehydes. Suitable reactions are provided in the Examples below.

EXAMPLES

| Abbreviations | | | |
|---|---|---|---|
| ACN | acetonitrile | h | Hour(s) |
| conc. | concentrated | $K_2CO_3$ | Potassium carbonate |
| DMF | N,N-Dimethyl formamide | MeOH | methanol |
| EtOH | Ethanol | min | minute |
| EtOAc | Ethyl Acetate | MS | Mass Spectrometry |
| THF | Tetrahydrofuran | LiOH | Lithium hydroxide |
| rt | Room temperature | o/n | Over night |

A range of acyl hydrazones can be prepared by the synthetic route depicted in Scheme 1. Heating an equimolar mixture of a dihydroquinolone ketone derivative A and substituted acyl hydrazides in ethanol or other suitable solvent, with a catalytic amount of acid, furnished target acyl Example: (Table 1)

(E)-N'-(6,7-Dihydroquinolin-8(5H)-ylidene)nicotinohydrazide (1)

To a solution of 6,7-Dihydroquinolin 8(5H)-one (622 mg, 4.22 mmol) in EtOH was added nicotinic acid hydrazide (575 mg, 4.22 mmol) followed by the addition of catalytic para-toluene sulphonic acid (7 mg). The reaction was heated to 45° C. for 1 h, then left to cool overnight. A cream coloured solid was collected by filtration which was suspended in MeOH. The filtrate was cooled to 4° C. overnight. Off-white needles were collected by filtration to afford target compound (E)-N'-(6,7-dihydroquinolin-8(5H-)-ylidene) nicotinohydrazide 1 (112 mg). $^1$H NMR (600 MHz, d6-DMSO) δ 1.96 (t, J=6.0 Hz, 2H), 2.99 (t, J=6.0 Hz, 4H), 7.64 (dd, J=7.8, 4.8 Hz, 1H), 7.85 (br s, 1H), 8.38 (d, J=6.6 Hz, 2H), 8.68 (d, J74.8 Hz, 1H), 8.81 (d, J=4.8 Hz, 1H), 9.13 (s, 1H), 11.64 (s, 1H). MS m/z 267.12 [M+H]$^+$.

TABLE 1

Selected Data for Compounds prepared via Scheme 1

| Compound | Structure | NMR | Mass Spec [M + H]+ |
|---|---|---|---|
| 2 | 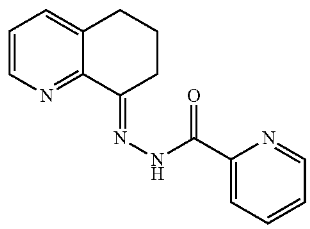 [SMILES: O=C(N/N=C1\CCCc2cccnc21)c1ccccn1] | $^1$H NMR (600 MHz, d6-DMSO) δ 1.97 (t, J = 6.0 Hz, 2H), 2.77 (t, J = 6.0 Hz, 2H), 2.90-2.94 (m, 2H), 7.50 (dd, J = 14.0, 6.6 Hz, 1H), 7.63-7.66 (m, 1H), 7.86-7.89 (m, 1H), 8.01-8.05 (m, 1H), 8.11-8.14 (m, 1H), 8.71-8.74 (m, 1H), 8.75-8.78 (m, 1H), 16.23 (s, 1H), | m/z 267.12 |
| 3 | 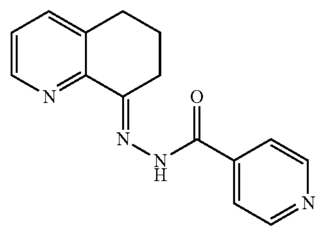 [SMILES: O=C(N/N=C1\CCCc2cccnc21)c1ccncc1] | $^1$H NMR (600 MHz, d6-DMSO) δ 1.96 (t, J = 6.0 Hz, 2H), 2.77 (t, J = 6.0 Hz, 2H), 2.93 (t, J = 6.0 Hz, 2H), 7.55 (dd, J = 7.8, 4.8 Hz, 1H), 7.80 (dd, J = 4.2, 1.2 Hz, 2H), 7.92 (d, J = 7.8 Hz, 1H), 8.77 (d, J = 4.2 Hz, 1H), 8.82 (dd, J = 4.8, 1.2 Hz, 2H). | m/z 267.12 |
| 4 | 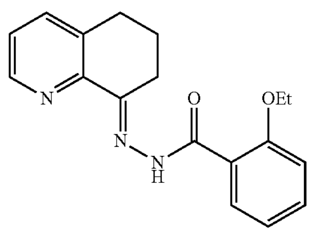 [SMILES: CCOc1ccccc1C(=O)N/N=C1\CCCc2cccnc21] | $^1$H NMR (600 MHz, d6-DMSO) δ 1.43-1.48 (m, 3H), 1.98 (t, J = 6.0 Hz, 2H), 2.86 (t, J = 6.0 Hz, 2H), 2.99 (t, J = 6.0 Hz, 2H), 4.22-4.27 (m, 2H), 7.13 (t, J = 7.8 Hz, 1H), 7.25 (d, J = 7.8 Hz, 1H), 7.56-8.00 (m, 1H), 7.90 (d, J = 4.8 Hz, 2H), 8.41 (d, J = 7.8 Hz, 1H), 8.68 (d, J = 4.8 Hz, 1H). | m/z 310.16 |
| 5 | 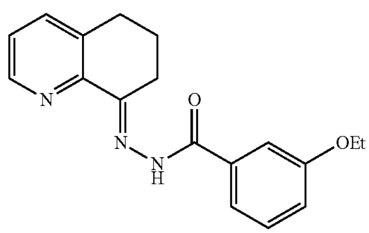 [SMILES: CCOc1cccc(C(=O)N/N=C2\CCCc3cccnc32)c1] | $^1$H NMR (600 MHz, d6-DMSO) δ 1.35 (t, J = 6.6 Hz, 3H), 1.96 (t, J = 6.0 Hz, 2H), 2.94-3.02 (m, 4H), 4.10 (q, J = 14.4, 6.6 Hz, 2H), 7.18 (dd, J = 8.4, 2.4 Hz, 1H), 7.43-7.46 (m, 2H), 7.51 (d, J = 8.4 Hz, 1H), 7.26 (dd, J = 6.6, 1.2 Hz, 1H), 8.44 (d, J = 8.4 Hz, 1H), 8.69 (d, J = 4.8 Hz, 1H), 11.37 (s, 1H). | m/z 310.16 |
| 6 | 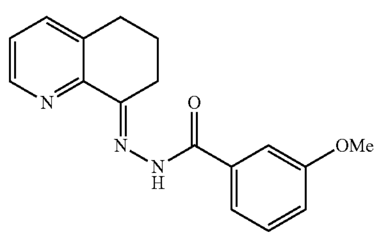 [SMILES: COc1cccc(C(=O)N/N=C2\CCCc3cccnc32)c1] | $^1$H NMR (600 MHz, d6-DMSO) δ 1.91-1.95 (m, 2H), 2.76 (t, J = 6.0 Hz, 2H), 2.92 (t, J = 6.0 Hz, 2H), 3.84 (s, 3H), 7.19 (dd, J = 7.8, 1.8 Hz, 1H), 7.40 (s, 1H), 7.46 (d, J = 7.2 Hz, 1H), 7.48-7.54 (m, 2H), 7.91 (d, J = 6.0 Hz, 1H), 8.68 (s, 1H). | m/z 296.14 |
| 7 | 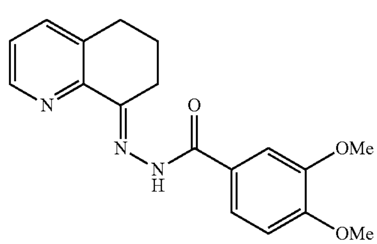 [SMILES: COc1ccc(C(=O)N/N=C2\CCCc3cccnc32)cc1OC] | $^1$H NMR (600 MHz, d6-DMSO) δ 1.95 (t, J = 6.0 Hz, 2H), 2.93-3.01 (m, 4H), 3.84 (s, 3H), 3.86 (s, 3H), 7.09 (d, J = 8.4 Hz, 1H), 7.51 (s, 1H), 7.61 (dd, J = 8.4, 1.8 Hz, 1H), 7.91 (d, J = 6.6 Hz, 1H), 8.42 (d, J = 6.6 Hz, 1H), 8.60 (s, 1H), 11.20 (br s, 1H). | m/z 326.1498 |

TABLE 1-continued

Selected Data for Compounds prepared via Scheme 1

| Compound | Structure | NMR | Mass Spec [M + H]+ |
| --- | --- | --- | --- |
| 8 | 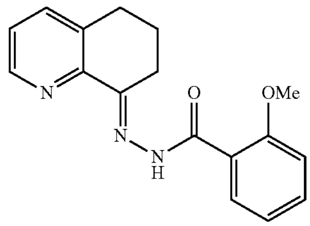 [SMILES: COc1ccccc1C(=O)N/N=C1\CCCc2cccnc21] | $^1$H NMR (600 MHz, d6-DMSO) δ 1.98 (t, J = 6.0 Hz, 2H), 2.85 (t, J = 6.0 Hz, 2H), 2.99 (t, J = 6.0 Hz, 2H), 3.91 (s, 3H), 7.13 (t, J = 7.8 Hz, 1H), 7.26 (d, J = 7.8 Hz, 1H), 7.60 (t, J = 7.8 Hz, 1H), 7.85 (s, 1H), 7.91-7.94 (m, 1H), 8.15 (d, J = 7.8 Hz, 1H), 8.65 (s, 1H), 11.36 (s, 1H). | m/z 296.14 |
| 9 | 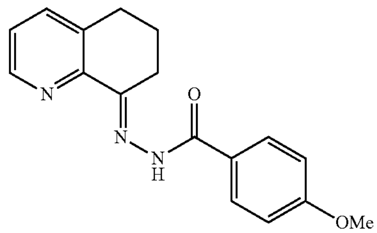 [SMILES: COc1ccc(C(=O)N/N=C2\CCCc3cccnc32)cc1] | $^1$H NMR (600 MHz, d6-DMSO) δ 1.95 (t, J = 6.6 Hz, 2H), 2.75 (s, 2H), 2.92 (t, J = 6.6 Hz, 1H), 3.84 (s, 3H), 7.12 (t, J = 7.8 Hz, 2H), 7.52 (dd, J = 7.8, 3.6 Hz, 1H), 7.85-7.91 (m, 3H), 8.74 (d, J = 3.6 Hz, 1H) | m/z 296.14 |
| 10 | 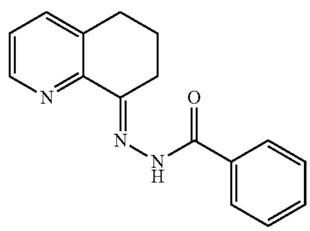 [SMILES: O=C(N/N=C1\CCCc2cccnc21)c1ccccc1] | $^1$H NMR (600 MHz, d6-DMSO) δ 1.95 (t, J = 5.4 Hz, 2H), 2.75-2.80 (m, 2H), 2.92 (t, J = 5.4 Hz, 2H), 7.48-7.52 (m, 1H), 7.57-7.62 (m, 3H), 7.82-7.88 (m, 3H), 8.72 (d, J = 3.0 Hz, 1H). | m/z 266.13 |
| 11 | 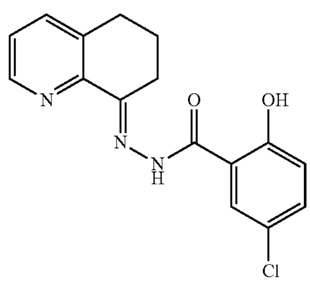 [SMILES: O=C(N/N=C1\CCCc2cccnc21)c1cc(Cl)ccc1O] | $^1$H NMR (600 MHz, d6-DMSO) δ 1.99 (t, J = 6.0 Hz, 2H), 2.79-2.84 (m, 2H), 2.98 (t, J = 6.0 Hz, 2H), 7.13 (d, J = 7.2 Hz, 1H), 7.51 (dd, J = 8.4, 2.4 Hz, 1H), 7.87-7.92 (m, 2H), 8.37 (br s, 1H) 8.68 (s, 1H), 11.65 (br s, 1H), 12.28 (br s, 1H). | m/z 316.08 |
| 12 | 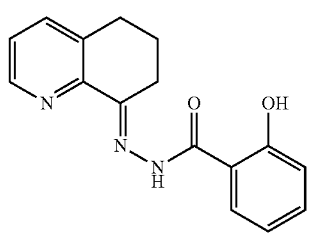 [SMILES: O=C(N/N=C1\CCCc2cccnc21)c1ccccc1O] | $^1$H NMR (600 MHz, d6-DMSO) δ 1.95 (m, 2H), 2.82 (br s, 2H), 2.89 (s, 2H), 6.98 (s, 1H), 7.05 (s, 1H), 7.42 (d, J = 7.2 Hz, 1H), 7.54 (dd, J = 7.8, 4.8 Hz, 1H), 7.93 (d, J = 7.2 Hz, 1H), 7.99 (dd, J = 7.8, 1.8 Hz, 1H), 8.59 (d, J = 3.6 Hz, 1H), 11.56 (br s, 1H), 11.85 (br s, 1H). | m/z 282.12 |
| 13 | 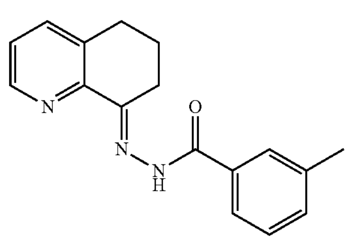 [SMILES: Cc1cccc(C(=O)N/N=C2\CCCc3cccnc32)c1] | $^1$H NMR (600 MHz, d6-DMSO) δ 1.96 (t, J = 6.0 Hz, 2H), 2.40 (s, 3H), 2.96-3.02 (m, 4H), 7.41-7.46 (m 2H), 7.72-7.77 (m, 2H), 7.94 (dd, J = 7.8, 5.4 Hz, 1H), 8.46 (d, J = 7.8 Hz, 1H), 8.69 (d, J = 5.4 Hz, 1H), 11.40 (s, 1H). | m/z 280.14 |

TABLE 1-continued

Selected Data for Compounds prepared via Scheme 1

| Compound | Structure | NMR | Mass Spec [M + H]+ |
|---|---|---|---|
| 14 | 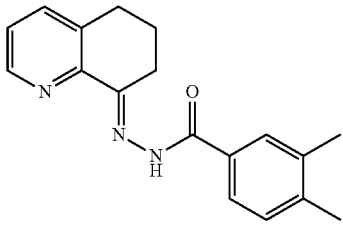 [SMILES: Cc1ccc(C(=O)N/N=C2\CCCc3cccnc32)cc1C] | ¹H NMR (600 MHz, d6-DMSO) δ 1.96 (t, J = 6.0 Hz, 2H), 2.30 (s, 3H), 2.32 (s, 3H), 2.94-3.01 (m, 4H), 7.30 (d, J = 7.8 Hz, 1H), 7.68 (d, J = 7.8 Hz, 1H), 7.74 (s, 1H), 7.92 (t, J = 6.6 Hz, 1H), 8.44 (d, J = 6.6 Hz, 1H), 8.68 (d, J = 4.8 Hz, 1H). | m/z 294.1600 |
| 15 | 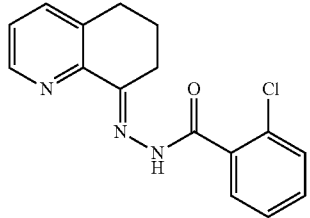 [SMILES: O=C(N/N=C1\CCCc2cccnc21)c1ccccc1Cl] | ¹H NMR (600 MHz, d6-DMSO) some peaks not well resolved δ 1.93 (t, J = 6.0 Hz, 2H), 2.82 (t, J = 6.0 Hz, 2H), 2.97 (t, J = 6.0 Hz, 2H), 7.45 (t, J = 7.8 Hz, 1H), 7.58 (t, J = 7.8 Hz, 1H), 7.87-7.93 (m, 1H), 7.97-8.02 (m, 2H), 8.39-8.44 (m, 1H), 8.66 (s, 1H), 11.61 (s, 1H) | m/z 300.09 |
| 16 | 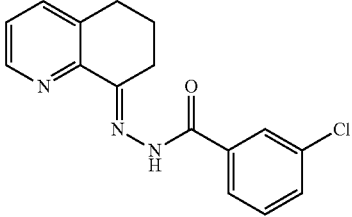 [SMILES: O=C(N/N=C1\CCCc2cccnc21)c1cccc(Cl)c1] | ¹H NMR (600 MHz, d6-DMSO) δ 1.96 (t, J = 6.0 Hz, 2H), 2.77 (t, J = 6.0 Hz, 2H), 2.95 (t, J = 6.0 Hz, 2H), 7.54 (dd, J = 7.8 Hz, 4.8 Hz, 1H), 7.64 (t, J = 7.8 Hz, 1H), 7.71 (d, J = 7.8 Hz, 1H), 7.84 (d, J = 7.8 Hz, 1H), 7.88 (s, 1H), 7.93 (d, J = 7.8 Hz, 1H), 8.70 (d, J = 4.8 Hz, 1H). | m/z 300.09 |
| 17 | 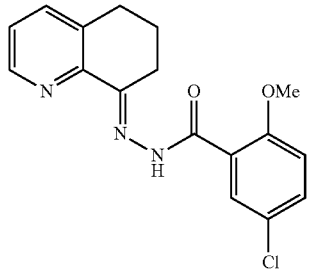 [SMILES: COc1ccc(Cl)cc1C(=O)N/N=C1\CCCc2cccnc21] | ¹H NMR (600 MHz, d6-DMSO) δ 1.90 (t, J = 6.0 Hz, 2H), 2.76-3.01 (m, 4H), 4.00 (s, 3H), 7.28 (d, J = 7.8 Hz, 1H), 7.30-7.35 (m, 1H), 7.60-7.66 (m, 2H), 7.85 (d, J = 7.8 Hz, 1H), 8.53 (t, J = 4.2 Hz, 1H), 10.92 (s, 1H) | m/z 330.10 |
| 18 | 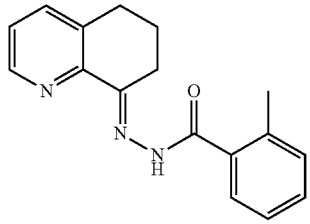 [SMILES: Cc1ccccc1C(=O)N/N=C1\CCCc2cccnc21] | ¹H NMR (600 MHz, d6-DMSO) δ 1.91 (t, J = 6.0 Hz, 2H), 2.34 (s, 3H), 2.94 (t, J = 6.0 Hz, 2H), 2.95 (s, 2H), 7.27-7.32 (m, 2H), 7.39-7.46 (m, 2H), 7.87 (br s, 1H), 8.34 (s, 1H), 8.63 (s, 1H), 11.41 (s, 1H). | m/z 280.15 |
| 19 | 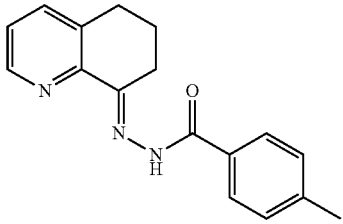 [SMILES: Cc1ccc(C(=O)N/N=C2\CCCc3cccnc32)cc1] | ¹H NMR (600 MHz, d6-DMSO) δ 2.03 (t, J = 6.0 Hz, 2H), 2.50 (s, 3H), 3.05-3.11 (m, 4H), 7.45 (d, J = 7.8 Hz, 2H), 7.96 (d, J = 7.8 Hz, 2H), 8.54 (d, J = 7.8 Hz, 1H), 8.03 (d, J = 6.0 Hz, 1H), 8.79 (s, 1H), 11.4 (s, 1H). | m/z 280.15 |

TABLE 1-continued

Selected Data for Compounds prepared via Scheme 1

| Compound | Structure | NMR | Mass Spec [M + H]+ |
|---|---|---|---|
| 20 | 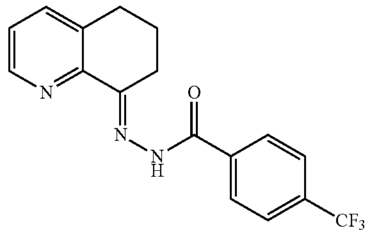 [SMILES: O=C(N/N=C1\CCCc2cccnc21)c1ccc(C(F)(F)F)cc1] | $^1$H NMR (600 MHz, d6-DMSO) δ 1.95-1.98 (m, 2H), 2.96-3.01 (m, 4H), 7.88-7.93 (m, 3H), 8.10-8.14 (m, 2H), 8.40-8.43 (m, 1H), 8.69 (d, J = 4.8 Hz, 1H), 11.61 (s, 1H). | m/z 334.12 |
| 21 | 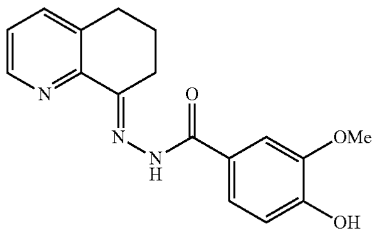 [SMILES: COc1cc(C(=O)N/N=C2\CCCc3cccnc32)ccc1O] | $^1$H NMR (600 MHz, d6-DMSO) δ 1.96 (t, J = 6.0 Hz, 2H), 2.76 (t, J = 6.0 Hz, 2H), 2.93 (t, J = 6.0 Hz, 2H), 3.86 (s, 3H), 6.94 (d, J = 7.8 Hz, 1H), 7.37-7.43 (m, 2H), 7.51 (dd, J = 7.8, 4.8 Hz, 1H), (d, J = 7.8 Hz, 1H), 8.71 (d, J = 4.8 Hz, 1H), 9.89 (br s, 1H). | m/z 312.13 |
| 22 | 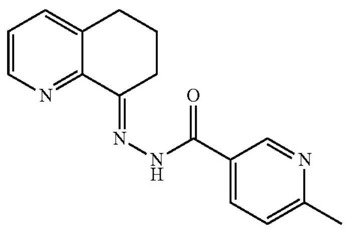 [SMILES: Cc1ccc(C(=O)N/N=C2\CCCc3cccnc32)cn1] | $^1$H NMR (600 MHz, d6-DMSO) δ 1.92-1.99 (m, 2H), 2.56 (s, 3H), 2.74-2.79 (m, 2H), 2.88-2.94 (m, 2H), 7.46 (d, J = 7.8 Hz, 1H), 7.52 (dd, J = 6.6, 4.2 Hz, 1H), 7.91 (d, J = 7.2 Hz, 1H), 8.12 (d, J = 7.2 Hz, 1H), 8.72 (s, 1H), 8.93 (s, 1H) | m/z 281.1392 |
| 23 | 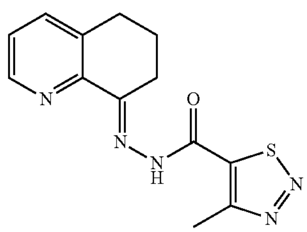 [SMILES: Cc1nnsc1C(=O)N/N=C1\CCCc2cccnc21] | $^1$H NMR (600 MHz, d6-DMSO) δ 1.87 (t, J = 6.0 Hz, 2H), 2.80-2.84 (m, 4H), 2.97 (s, 3H), 7.36 (dd, J = 7.2, 4.8 Hz, 1H), 7.66 (d, J = 7.2 Hz, 1H), 8.68 (d, J = 4.8 Hz, 1H), 11.62 (s, 1H). | m/z 288.0913 |
| 24 | 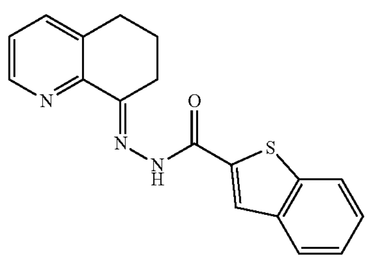 [SMILES: O=C(N/N=C1\CCCc2cccnc21)c1cc2ccccc2s1] | $^1$H NMR (600 MHz, d6-DMSO) δ 1.96 (t, J = 6.0 Hz, 2H), 2.92-2.99 (m, 4H), 7.42-7.58 (m, 2H), 7.72-7.80 (m, 1H), 8.00-8.06 (m, 2H), 8.15-8.26 (m, 1H), 8.51-8.62 (m, 1H), 8.69 (s, 1H), 11.48 (br s, 1H). | m/z 322.1009 |
| 25 | 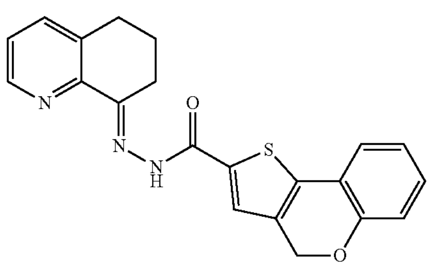 [SMILES: O=C(N/N=C1\CCCc2cccnc21)c1cc2c(s1)-c1ccccc1OC2] | $^1$H NMR (600 MHz, d6-DMSO) δ 1.97 (quintet, J = 6.0 Hz, 2H), 2.94-2.99 (m, 4H), 5.32 (s, 2H), 6.97-7.02 (m, 2H), 8.07 (s, 1H), 7.84-7.88 (m, 1H), 7.25 (d, J = 7.2 Hz, 1H), 7.45 (d, J = 7.2 Hz, 1H), 8.36 (s, 1H), 8.73 (d, J = 4.8 Hz, 1H), 11.43 (s, 1H). | m/z 376.11 |

TABLE 1-continued

Selected Data for Compounds prepared via Scheme 1

| Compound | Structure | NMR | Mass Spec [M + H]+ |
|---|---|---|---|
| 26 | 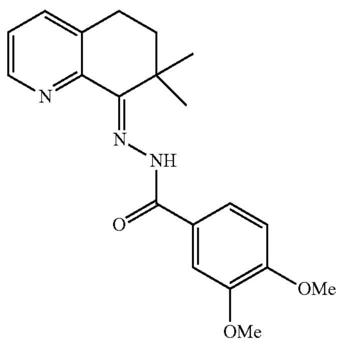 [SMILES: COc1ccc(C(=O)N/N=C2/c3ncccc3CCC2(C)C)cc1OC] | ¹H NMR (500 MHz, d6-DMSO) δ 1.24 (s, 6H), 1.93 (t, J = 6.5 Hz, 2H), 2.95 (t, J = 6.5 Hz, 2H), 3.84 (s, 3H), 3.86 (s, 3H), 7.14 (d, J = 8.5 Hz, 1H), 7.42 (s, 1H), 7.48-7.52 (m, 2H), 7.90 (d, J = 7.5 Hz, 1H), 8.71 (d, J = 3.5 Hz, 1H), 15.98 (s, 1H). | m/z 354.18 |
| 27 | 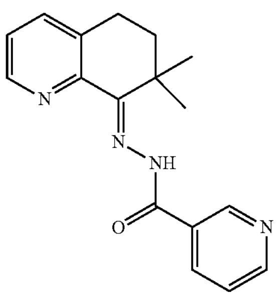 [SMILES: CC1(C)CCc2cccnc2/C1=N/NC(=O)c1cccnc1] | ¹H NMR (600 MHz, d6-DMSO) 3:1 geometric isomers-major isomer δ 1.25 (s, 6H), 1.84 (t, J = 6.6 Hz, 2H), 2.96 (t, J = 6.6 Hz, 2H), 7.52-7.57 (m, 2H), 7.63 (dd, J = 7.8, 4.8 Hz, 1H), 7.92 (d, J = 7.8 Hz, 1H), 8.25 (d, J = 7. Hz, 1H), 8.73 (d, J = 3.6 Hz, 1H), 8.80 (d, J = 4.8 Hz, 1H), 9.06 (s, 1H), 11.98 (br s, 1H). | m/z 295.1554 |
| 28 | 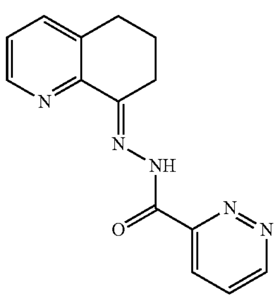 [SMILES: O=C(N/N=C1\CCCc2cccnc21)c1cccnn1] | ¹H NMR (600 MHz, d6-DMSO) 1:1 geometric isomers δ 1.96-2.02 (m, 4H), 2.80 (t, J = 6.0 Hz, 2H), 2.95 (t, J = 6.0 Hz, 2H), 2.99-3.05 (m, 4H), 7.52 (dd, J = 7.8, 4.8 Hz, 1H), 7.90-8.03 (m, 4H), 8.30-8.35 (m, 2H), 8.52 (d, J = 13.8 Hz, 1H), 8.66 (d, J = 3.0 Hz, 1H), 8.73 (d, J = 4.8 Hz, 1H), 9.43-9.46 (m, 1H), 9.51 (d, J = 4.2 Hz, 1H), 11.32 (br s, 1H). | m/z 268.1196 |
| 29 | 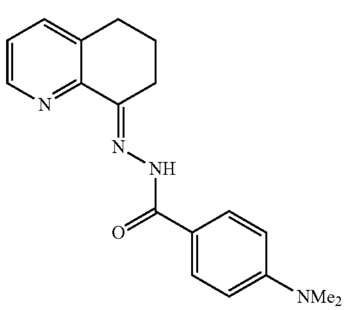 [SMILES: CN(C)c1ccc(C(=O)N/N=C2\CCCc3cccnc32)cc1] | ¹H NMR (600 MHz, d6-DMSO) δ 1.93 (t, J = 6.0 Hz, 2H), 7.72 (t, J = 6.0 Hz, 2H), 2.89 (t, J = 6.0 Hz, 2H), 2.91 (s, 3H), 2.93 (s, 3H), 6.79 (d, J = 9.0 Hz, 1H), 7.48 (d, J = 7.8 Hz, 1H), 7.74 (d, J = 7.2 Hz, 2H), 7.86 (d, J = 7.2 Hz. 1H), 8.72 (d, 3.6 Hz, 1H), | m/z 309.17 |

TABLE 1-continued

Selected Data for Compounds prepared via Scheme 1

| Compound | Structure | NMR | Mass Spec [M + H]+ |
|---|---|---|---|
| 30 | 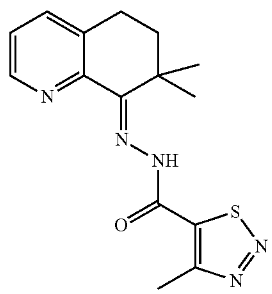 [SMILES: Cc1nnsc1C(=O)N/N=C1/c2ncccc2CCC1(C)C] | $^1$H NMR (500 MHz, d6-DMSO) δ 1.35 (s, 6H), 1.85 (t, J = 6.0 Hz, 2H), 2.96 (t, J = 6.0 Hz, 2H), 3.31 (s, 3H), 7.57 (dd, J = 8.0, 4.5 Hz, 1H), 7.93 (d, J = 6.5 Hz, 1H), 8.50 (d, J = 4.5 Hz, 1H), 15.62 (s, 1H) | m/z 316.12 |
| 31 | 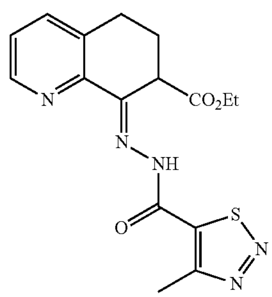 [SMILES: CCOC(=O)C1CCc2cccnc2/C1=N/NC(=O)c1snnc1C] | $^1$H NMR (600 MHz, d6-DMSO) δ 1.12 (t, J = 7.2 Hz, 3H), 2.22-2.26 (m, 1H), 2.34-2.38 (m, 2H), 2.84-2.97 (m, 2H), 2.96 (s, 3H), 4.04 (t, J = 6.0 Hz, 1H), 4.15 (q, J = 7.2, 1.8 Hz, 2H), 7.56 (dd, J = 7.2, 4.2 Hz, 1H), 7.93 (d, J = 7.2 Hz, 1H), 8.73 (d, J = 4.2 Hz, 1H). | m/z 360.1123 |
| 32 | 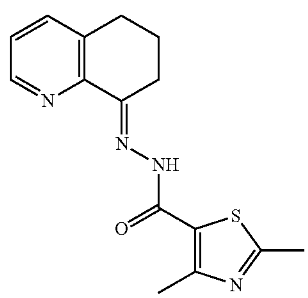 [SMILES: Cc1nc(C)c(C(=O)N/N=C2\CCCc3cccnc32)s1] | $^1$H NMR (600 MHz, d6-DMSO) δ 1.91-1.97 (m, 2H), 2.61 (s, 3H), 2.66 (s, 3H), 2.88 (t, J = 7.8 Hz, 2H), 2.98 (t, J = 7.8 Hz, 2H) 7.95 (app t, J = 7.2 Hz, 1H), 8.47 (d, J = 9.6 Hz, 1H), 8.73 (d, J = 7.2 Hz, 1H), 11.54 (br s, 1H). | m/z 301.1119 |
| 33 | 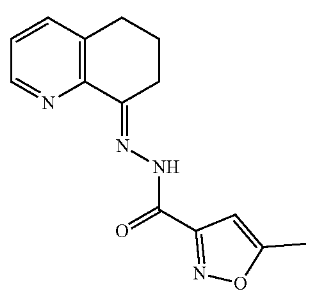 [SMILES: Cc1cc(C(=O)N/N=C2\CCCc3cccnc32)no1] | $^1$H NMR (600 MHz, d6-DMSO) δ 1.94 (t, J = 6.0 Hz, 2H), 2.51 (s, 3H), 2.92 (t, J = 6.0 Hz, 2H), 2.99 (t, J = 6.0 Hz, 2H), 6.75 (s, 1H), 7.92 (s, 1H), 8.41 (s, 1H), 8.69 (d, J = 4.8 Hz, 1H), 11.58 (br s, 1H). | m/z 271.1186 |
| 156 | 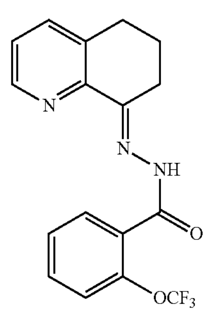 [SMILES: O=C(N/N=C1\CCCc2cccnc21)c1ccccc1OC(F)(F)F] | $^1$H NMR (500 MHz, d6-DMSO) δ 1.93 (t, J = 5.5 Hz, 2H), 2.84 (t, J = 5.5 Hz, 2H), 2.95-2.99 (m, 2H), 7.52-7.56 (m, 2H), 7.67-7.74 (m, 2H), 7.92 (s, 1H), 8.42 (d, J = 6.0 Hz, 1H), 8.68 (s, 1H), 11.63 (s, 1H) | m/z 350.1113 |

TABLE 1-continued

Selected Data for Compounds prepared via Scheme 1

| Compound | Structure | NMR | Mass Spec [M + H]+ |
|---|---|---|---|
| 157 | 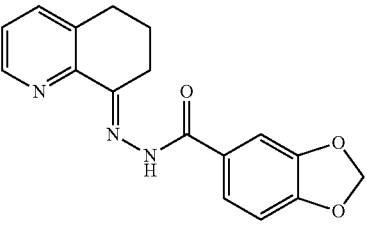 [SMILES: O=C(N/N=C1\CCCc2cccnc21)c1ccc2c(c1)OCO2] | | m/z 310.1187 |
| 158 | 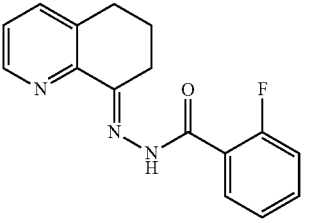 [SMILES: O=C(N/N=C1\CCCc2cccnc21)c1ccccc1F] | | m/z 284.1193 |
| 159 | 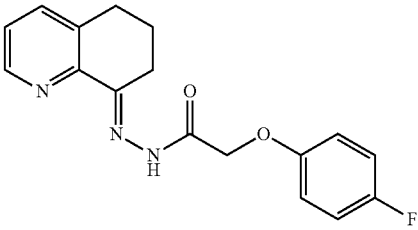 [SMILES: O=C(COc1ccc(F)cc1)N/N=C1\CCCc2cccnc21] | | m/z 314.1301 |
| 180 | 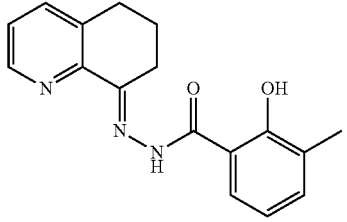 [SMILES: Cc1cccc(C(=O)N/N=C2\CCCc3cccnc32)c1O] | $^1$H NMR (400 MHz, d6-DMSO) δ 1.98 (t, J = 6.0 Hz, 2H), 2.48 (s, 3H), 2.78 (t, J = 6.0 Hz, 2H), 2.94 (t, J = 6.0 Hz, 2H), 6.95 (t, J = 7.2 Hz, 1H), 7.39 (d, J = 7.2 Hz, 1H), 7.54-7.58 (m, 2H), 7.94 (d, J = 7.2 Hz, 1H), 8.80 (d, J = 4.4 Hz, 1H). | m/z 296.1392 |

Similarly, fused cyclopentane derivatives D could be synthesised according to Scheme 2.

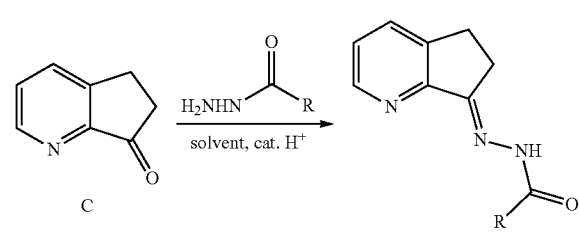

Scheme 2

Example 2 (Table 2)

(E)-N'-(5H-Cyclopenta[b]pyridin-7(6H)-ylidene)-3,4-dimethoxybenzohydrazide (38)

To a solution of 5H-cyclopenta[b]pyridin-7(6H)-one (40 mg, 0.30 mmol) in MeOH (8 mL) was added 3,4-dimethoxybenzhydrazide (59 mg, 1 mol eq), followed by one drop of concentrated hydrochloric acid. The reaction was stirred overnight. An off-white solid was collected by filtration to afford the desired (E)-N'-(5H-cyclopenta[b]pyridin-7(6H)-ylidene)-3,4-dimethoxybenzohydrazide 38 (30 mg). $^1$H NMR (600 MHz, d6-DMSO) δ 2.95 (t, J=6.0 Hz, 2H), 3.11-3.16 (m, 2H), 3.84 (s, 3H), 3.87 (s, 3H), 7.14 (d, J=8.4 Hz, 1H), 7.46 (s, 1H), 7.52 (dd, J=7.8, 4.8 Hz, 2H), 8.02 (d, J=7.2 Hz, 1H), 8.68 (d, J=4.8 Hz, 1H). MS m/z 312.13[M+H]+.

TABLE 2

Selected data for compounds synthesised by Scheme 2.

| Compound | Structure | Spectral Data |
|---|---|---|
| 34 | 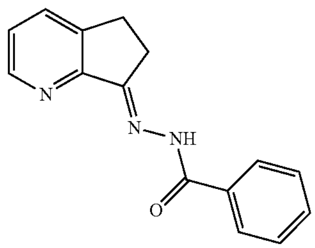 [SMILES: O=C(N/N=C1\CCc2cccnc21)c1ccccc1] | $^1$H NMR (500 MHz, d6-DMSO) δ 2.93-2.96 (m, 2H), 3.15 (t, J = 6.0 Hz, 2H), 7.52 (dd, J = 7.8, 4.8 Hz, 1H), 7.56-7.60 (m, 4H), 7.61-7.65 (m, 1H), 7.92 (d, J = 7.2 Hz, 1H), 8.02 (d, J = 7.2 Hz, 1H). m/z 252.11 [M + H]$^+$ |
| 35 | 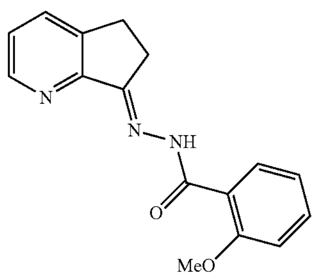 [SMILES: COc1ccccc1C(=O)N/N=C1\CCc2cccnc21] | $^1$H NMR (600 MHz, d6-DMSO) δ 2.92-2.95 (m, 2H), 3.11 (t, J = 6.0 Hz, 2H), 4.02 (s, 3H), 7.12 (d, J = 7.2 Hz, 1H), 7.24 (d, J = 7.8 Hz, 1H), 7.35 (dd, J = 7.8, 4.8 Hz, 1H), 7.54-7.58 (m, 1H), 7.84 (d, J = 7.8 Hz, 1H), 7.93 (dd, J = 7.8, 1.2 Hz, 1H), 8.56 (d, J = 4.8 Hz, 1H). |
| 36 | 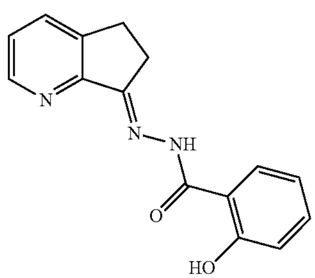 [SMILES: O=C(N/N=C1\CCc2cccnc21)c1ccccc1O] | $^1$H NMR (600 MHz, d6-DMSO) δ 2.92-2.95 (m, 2H), 3.16 (t, J = 6.0 Hz, 2H), 6.97 (t, J = 7.8 Hz, 1H), 7.05 (d, J = 7.8H, 1H), 7.23 (s, 1H), 7.42 (d, J = 6.6 Hz, 1H), 7.55 (s, 1H), 7.97 (d, J = 7.8 Hz, 1H), 8.07 (d, J = 6.6 Hz, 1H), 8.62 (d, J = 4.8 Hz, 1H), 11.25 (s, 1H), 11.78 (s, 1H). |
| 37 | 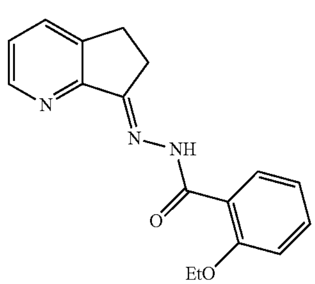 | $^1$H NMR (600 MHz, d6-DMSO) δ 1.49 (t, J = 7.2 Hz, 3H), 2.92 (t, J = 6.0 Hz, 2H), 3.12 (t, J = 6.0 Hz, 2H), 4.28 (q, J = 7.2 Hz, 2H), 7.11 (t, J = 7.8 Hz, 1H), 7.23 (d, J = 7.8 Hz, 1H), 7.35 (dd, J = 7.8, 4.8 Hz, 1H), 7.54 (t, J = 7.2 Hz, 1H), 7.83 (d, J = 7.2 Hz, 1H), 7.98 (dd, J = 7.8, 1.2 Hz, 1H), 8.56 (d, J = 4.8 Hz, 1H). m/z 296.14 [M + H]$^+$. |

The following 2-O-phenol substituted benzohydrazide derivatives were synthesised according to Scheme 3. Phenol intermediate E, synthesised using the procedure outlined in Scheme 1, was allowed to react with an alkyl halide in the presence of potassium carbonate to provide the required alkyl amino substituted ethers F.

Scheme 3

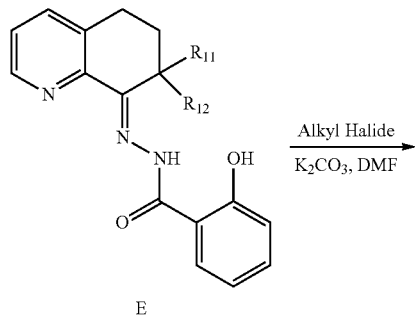

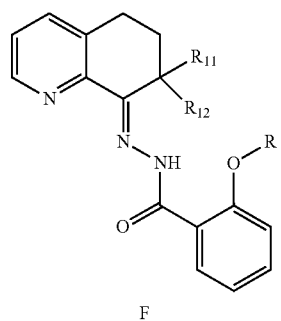

Example 3

(E)-N'-(6,7-Dihydroquinolin-8(5H)-ylidene)-2-(2-(pyrrolidin-1-yl)ethoxy)benzohydrazide hydrochloride (41)

To a suspension of the (E)-N'-(6,7-dihydroquinolin-8 (5H)-ylidene)-2-hydroxybenzohydrazide 12 (149 mg, 0.530 mmol) in dry DMF (10 mL) was added $K_2CO_3$ (246 mg, 1.78 mmol) and the chloroethylpyrrolidine hydrochloride (95 mg, 0.55 mmol). The reaction was heated to 45° C. for 2 days, then cooled to rt. The reaction was extracted into EtOAc (×3). Combined organic layers were washed with $H_2O$, brine, dried over $Na_2SO_4$, filtered and concentrated to afford a gummy brown solid. The residue was taken up in MeOH (7 mL) and treated with concentrated hydrochloric acid (0.3 mL). Solvent was removed in vacuo, the flask was cooled to rt, then ACN (5 mL) was added slowly. The flask was triturated and sonicated to provide (E)-N'-(6,7-dihydroquinolin-8(5H)-ylidene)-2-(2-(pyrrolidin-1-yl)ethoxy)benzohydrazide hydrochloride 41 as a fawn colored solid that was collected by filtration and dried at the pump. Yield 114 mg. $^1$H NMR (500 MHz, d6-DMSO) δ 1.85-1.92 (m, 2H), 1.94-1.99 (m, 4H), 2.95 (t, J=6.0 Hz, 2H), 2.99-3.07 (m, 4H), 3.54-3.62 (m, 4H), 4.22-4.26 (m, 2H), 7.16 (t, J=7.8 Hz, 1H), 7.24 (d, J=7.8 Hz, 1H), 7.58 (t, J=7.2 Hz, 1H), 7.83 (s, 1H), 7.89 (s, 1H), 8.41 (br s, 1H), 8.67 (br s, 1H), 11.37 (s, 1H), 11.45 (br s, 1H). MS m/z 379.21 $[M+H]^+$.

TABLE 3

| Compound | Structure | NMR Data | Mass Spec $[M + H]^+$ |
|---|---|---|---|
| 39 | 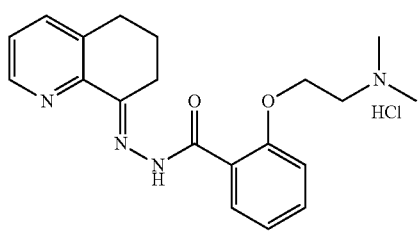 [SMILES: CN(C)CCOc1ccccc1C(=O)N/N=C1\CCCc2cccnc21 ; Cl] | $^1$H NMR (600 MHz, d6-DMSO) δ 1.97 (t, J = 6.0 Hz, 2H), 2.80 (s, 3H), 2.81 (s, 3H), 2.89 (t, J = 6.0 Hz, 2H), 3.00 (t, J = 6.0 Hz, 2H), 4.55 (s, 2H), 7.14 (t, J = 7.8 Hz, 1H), 7.26 J = 8.4 Hz, 1H), 7.57 (t, J = 7.2 Hz, 1H), 7.63 (d, J = 7.2 Hz, 1H), 7.96 (t, J = 7.2 Hz, 1H), 8.49 (d, J = 7.2 Hz, 1H), 8.71 (d, J = 4.2 Hz, 1H), 11.20 (br s, 1H), 11.42 (s, 1H). | m/z 353.20 |

TABLE 3-continued

Selected data for compounds according to Scheme 3

| Compound | Structure | NMR Data | Mass Spec [M + H]+ |
|---|---|---|---|
| 40 | 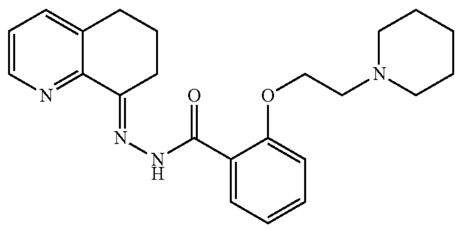 [SMILES: O=C(N/N=C1\CCCc2cccnc21)c1ccccc1OCCN1CCCCC1] | ¹H NMR (600 MHz, d6-DMSO) δ 1.29-1.35 (m, 2H), 1.40-1.45 (m, 4H), 1.89 (t, J = 6.0 Hz, 2H), 2.63-2.70 (m, 4H), 2.73 (t, J = 6.0 Hz, 2H), 2.78-2.84 (m, 4H), 4.34 (t, J = 6.0 Hz, 2H), 7.12 (t, J = 7.8 Hz, 1H), 7.28 (d, J = 7.8 Hz, 1H), 7.30-7.33 (m, 1H), 7.53 (t, J = 8.4 Hz, 1H), 7.64 (d, J = 6.6 Hz, 1H), 7.99 (d, J = 6.6 Hz, 1H), 8.52 (d, J = 3.0 Hz, 1H), 10.94 (s, 1H). | m/z 393.10 |
| 42 | 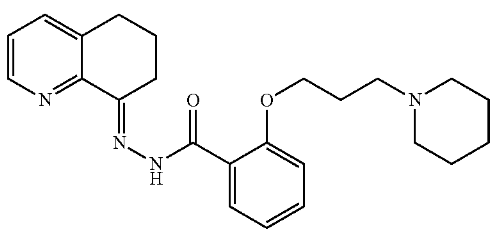 [SMILES: O=C(N/N=C1\CCCc2cccnc21)c1ccccc1OCCCN1CCCCC1] | ¹H NMR (600 MHz, d6-DMSO) δ 1.28-1.35 (m, 2H), 1.38-1.43 (m, 4H), 1.88 (t, J = 6.0 Hz, 2H), 1.97 (t, J = 6.0 Hz, 2H), 2.23-2.28 (m, 4H), 2.36 (t, J = 6.6 Hz, 2H), 2.70-2.78 (m, 4H), 4.23 (t, J = 6.6 Hz, 2H), 7.09 (t, J = 7.2 Hz, 1H), 7.92 (d, J = 7.2 Hz, 1H), 7.20 (d, J = 8.4 Hz, 1H), 7.29 (dd, J = 7.8, 4.8 Hz, 1H), 7.52 (t, J = 7.2 Hz, 1H), 7.62 (d, J = 7.2 Hz, 1H), 8.50 (d, J = 3.6 Hz, 1H), 10.83 (s, 1H). | m/z 407.24 |

A range of acyl hydrazones can be prepared by the synthetic route depicted in Scheme 4. Heating an equimolar mixture of the 6-membered heterocyclic ketone G and the acylhydrazide in ethanol or other suitable solvent in the presence a catalytic amount of acid, furnished target acyl hydrazone compounds H (see table 4). The ketone starting materials were available from commercial suppliers or known literature methods.

Scheme 4

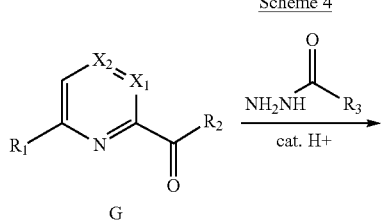

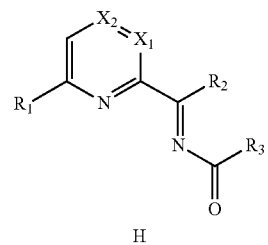

X1 = CH, N, C-alkyl
X2 = CH, N
R1 = CH, N
R1, R2 = H, alkyl, isoalkyl, cycloalkyl
R3 = Aryl, heteroaryl

Example 4

(E)-4-Methyl-N'-(1-(pyrimidin-2-yl)propylidene)-1,2,3-thiadiazole-5-carbohydrazide (43)

(Pyrimidin-2-yl)propan-1-one (114 mg) was heated together with 4-methyl-1,2,3-thiadiazole-5-carbohydrazide (132 mg) in EtOH (10 mL) in the presence of concentrated hydrochloric acid (one drop) to 60° C. for 30 min. The reaction was cooled to rt, then an off-white solid was collected by filtration. The crude product was further washed with ACN (×2) to generate (E)-4-methyl-N'-(1-(pyrimidin-2-yl)propylidene)-1,2,3-thiadiazole-5-carbohydrazide 43 (60 mg) as a white powder. $^1$H NMR (600 MHz, d6-DMSO) δ 1.07 (t, J=7.2 Hz, 3H), 2.97 (s, 3H), 3.06 (q, J=7.2 Hz, 2H), 7.57 (t, J=6.6 Hz, 1H), 9.01 (d, J=6.6 Hz, 2H), 11.96 (s, 1H). MS m/z 277.0865 [M+H]$^+$.

TABLE 4

| | MS Data for Compounds synthesised via Scheme 4 | |
| --- | --- | --- |
| Compound | Structure | Mass Spectrometry [M + H]$^+$ |
| 44 | | m/z 269.1397 |
| 45 | | m/z 285.1347 |
| 46 | | m/z 285.1345 |
| 47 | | m/z 271.12 |

TABLE 4-continued

MS Data for Compounds synthesised via Scheme 4

| Compound | Structure | Mass Spectrometry [M + H]+ |
|---|---|---|
| 48 | 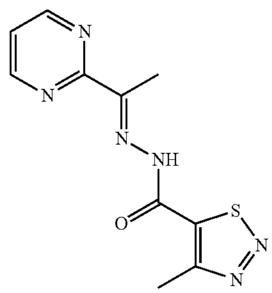 [SMILES: C/C(=N\NC(=O)c1snnc1C)c1ncccn1] | m/z 263.07 |
| 49 | 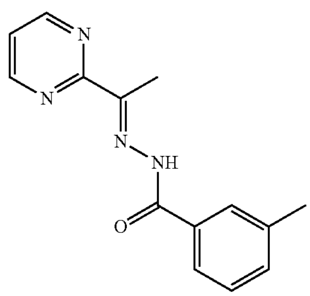 [SMILES: C/C(=N\NC(=O)c1cccc(C)c1)c1ncccn1] | m/z 255.12 |
| 50 | 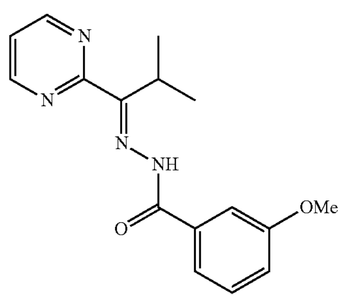 [SMILES: COc1cccc(C(=O)N/N=C(/c2ncccn2)C(C)C)c1] | m/z 299.15 |
| 51 | 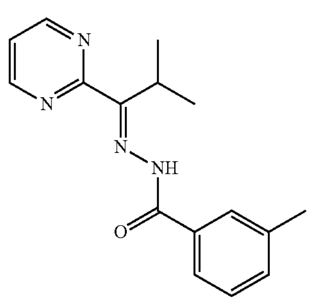 [SMILES: Cc1cccc(C(=O)N/N=C(/c2ncccn2)C(C)C)c1] | m/z 283.15 |
| 52 | 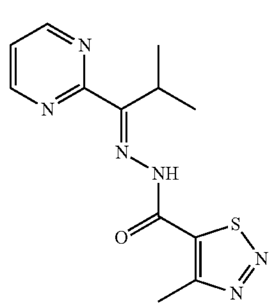 [SMILES: Cc1nnsc1C(=O)N/N=C(/c1ncccn1)C(C)C] | m/z 291.10 |

TABLE 4-continued

MS Data for Compounds synthesised via Scheme 4

| Compound | Structure | Mass Spectrometry [M + H]+ |
|---|---|---|
| 53 | 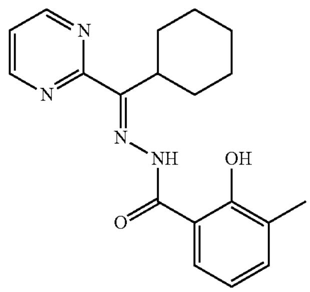 | m/z 306.1399 |
| 54 | 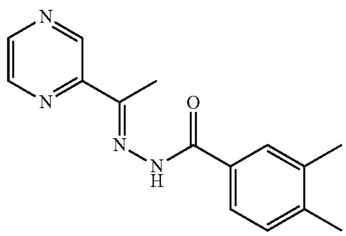 [SMILES: C/C(=N\NC(=O)c1ccc(C)c(C)c1)c1cnccn1] | m/z 269.1400 |
| 55 | 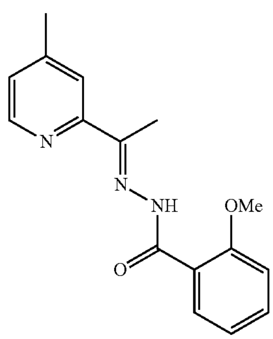 [SMILES: COc1ccccc1C(=O)N/N=C(\C)c1cc(C)ccn1] | m/z 284.1393 |
| 56 | 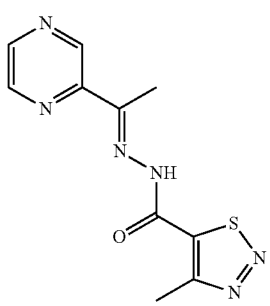 | m/z 276.0193 |
| 57 | 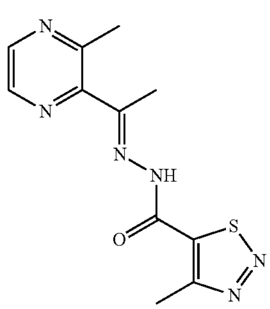 [SMILES: C/C(=N\NC(=O)c1snnc1C)c1nccnc1C] | m/z 277.0856 |

TABLE 4-continued

MS Data for Compounds synthesised via Scheme 4

| Compound | Structure | Mass Spectrometry [M + H]+ |
|---|---|---|
| 58 | 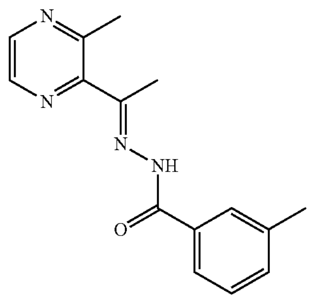 [SMILES: C/C(=N\NC(=O)c1cccc(C)c1)c1nccnc1C] | m/z 269.1396 |
| 59 | 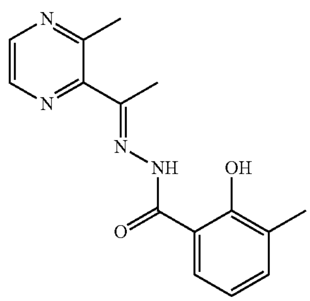 [SMILES: C/C(=N\NC(=O)c1cccc(C)c1O)c1nccnc1C] | m/z 285.1354 |
| 60 | 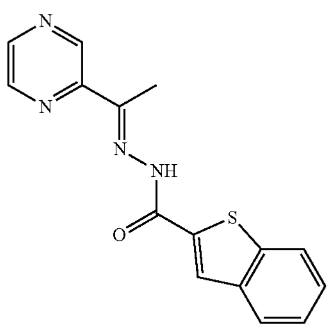 [SMILES: C/C(=N\NC(=O)c1cc2ccccc2s1)c1cnccn1] | m/z 297.0804 |
| 61 | 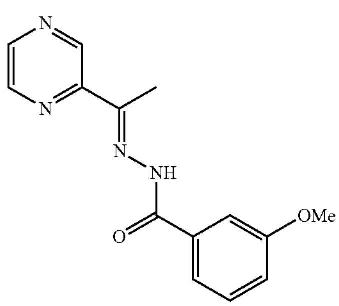 | m/z 285.1344 |
| 62 | 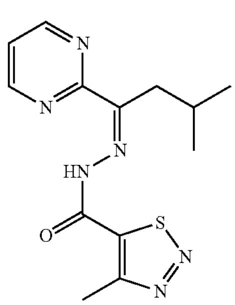 [SMILES: Cc1nnsc1C(=O)N/N=C(/CC(C)C)c1ncccn1] | m/z 305.1229 |

TABLE 4-continued

MS Data for Compounds synthesised via Scheme 4

| Compound | Structure | Mass Spectrometry [M + H]+ |
|---|---|---|
| 63 | 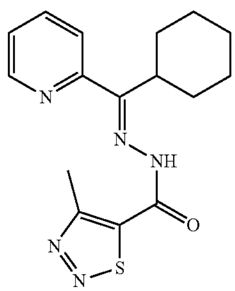 [SMILES: Cc1nnsc1C(=O)N/N=C(/c1ccccn1)C1CCCCC1] | m/z 330.1435 |
| 64 | 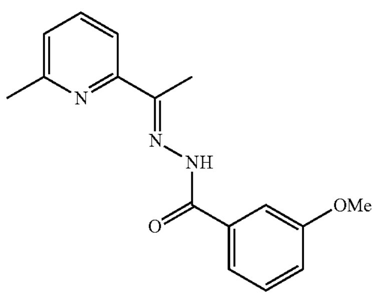 [SMILES: COc1cccc(C(=O)N/N=C(\C)c2cccc(C)n2)c1] | m/z 284.1963 |
| 65 | 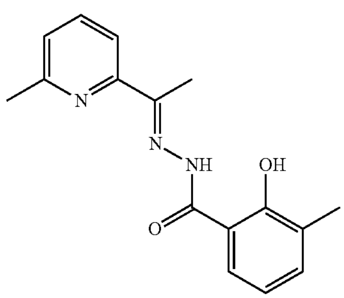 | m/z 284.2141 |
| 66 | 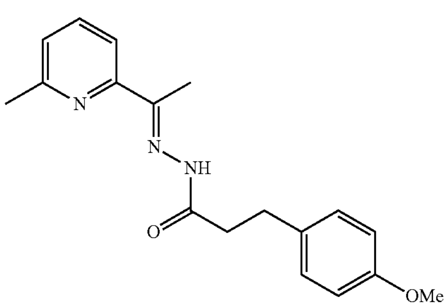 [SMILES: COc1ccc(CCC(=O)N/N=C(\C)c2cccc(C)n2)cc1] | m/z 312.2221 |
| 67 | 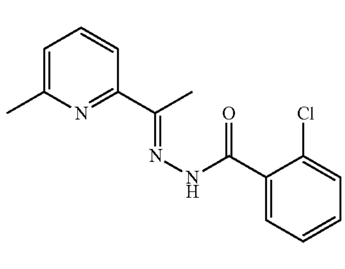 [SMILES: C/C(=N\NC(=O)c1ccccc1Cl)c1cccc(C)n1] | m/z 288.1760 |

TABLE 4-continued

MS Data for Compounds synthesised via Scheme 4

| Compound | Structure | Mass Spectrometry [M + H]+ |
|---|---|---|
| 68 | 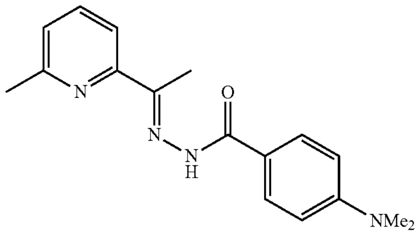 [SMILES: C/C(=N\NC(=O)c1ccc(N(C)C)cc1)c1cccc(C)n1] | m/z 297.2482 |
| 69 | 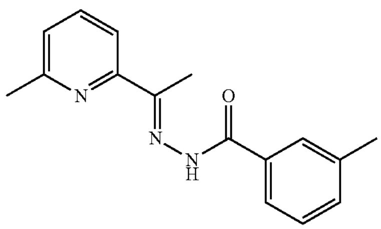 | m/z 268.1961 |
| 70 | 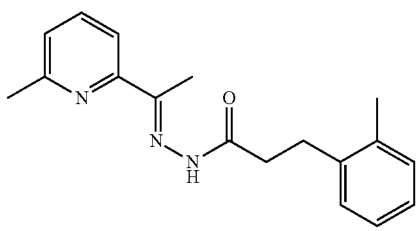 [SMILES: C/C(=N\NC(=O)CCc1ccccc1C)c1cccc(C)n1] | m/z 296.1758 |
| 71 | 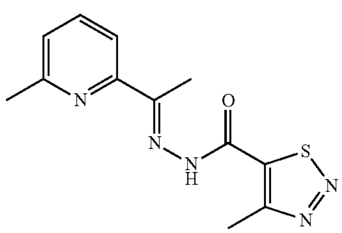 [SMILES: C/C(=N\NC(=O)c1snnc1C)c1cccc(C)n1] | m/z 276.0914 |
| 72 | 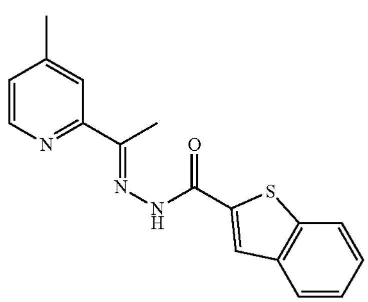 [SMILES: C/C(=N\NC(=O)c1cc2ccccc2s1)c1cc(C)ccn1] | m/z 310.0966 |
| 73 | 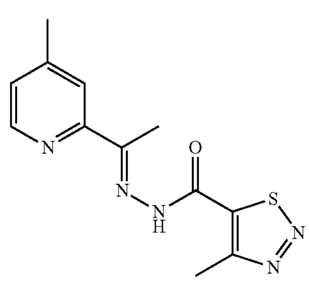 [SMILES: C/C(=N\NC(=O)c1snnc1C)c1cc(C)ccn1] | m/z 276.0913 |

TABLE 4-continued

MS Data for Compounds synthesised via Scheme 4

| Compound | Structure | Mass Spectrometry [M + H]+ |
|---|---|---|
| 74 | 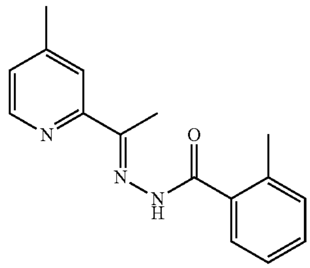 [SMILES: C/C(=N\NC(=O)c1ccccc1C)c1cc(C)ccn1] | m/z 268.1445 |
| 75 | 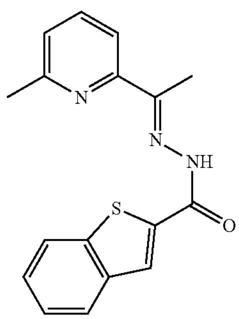 [SMILES: C/C(=N\NC(=O)c1cc2ccccc2s1)c1cccc(C)n1] | m/z 310.1210 |
| 197 | 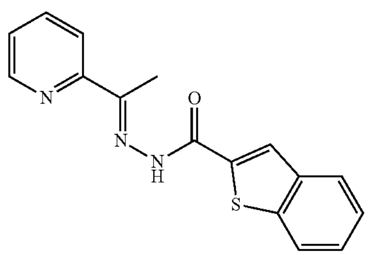 [SMILES: C/C(=N\NC(=O)c1cc2ccccc2s1)c1ccccn1] | m/z 296.0460 |

A range of substituted quinoline acyl hydrazones can be prepared by the synthetic route depicted in Scheme 5. Heating an equimolar mixture of acetyl quinoline I and substituted acylhydrazide in ethanol or other suitable solvent with a catalytic amount of acid, provided the target compounds J.

Scheme 5

R1 = Aryl, heteroaryl

-continued

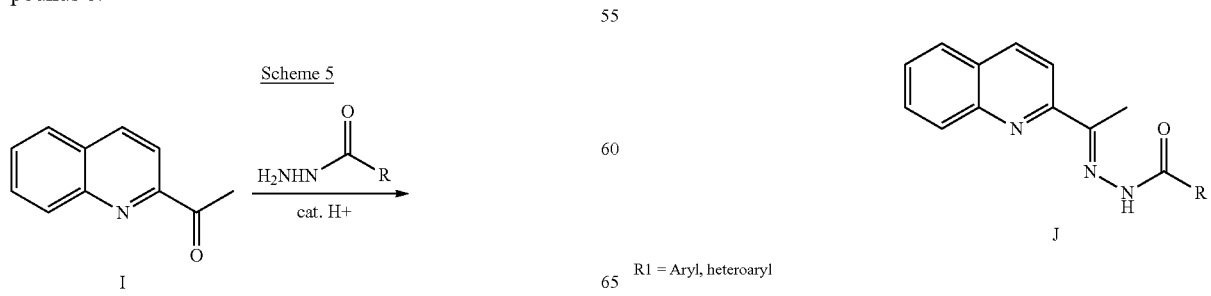

Example 5

(E)-N'-(1-(Quinolin-2-yl)ethylidene)picolinohydrazide (80)

2-Acetylquinoline (162 mg), pyridine-2-carboxylic acid hydrazide (113 mg) were heated together in EtOH (7 mL) at 60° C. One drop of concentrated hydrochloric acid was added and the reaction was stirred for 15 min at which time a precipitate formed. The reaction was cooled and the precipitate was collected by filtration to afford (E)-N'-(1-(quinolin-2-yl)ethylidene)picolinohydrazide 80 as an off-white powder (50 mg). $^1$H NMR (600 MHz, d6-DMSO) δ 2.64 (s, 3H), 7.62-7.65 (m, 1H), 7.74-7.77 (m, 1H), 7.80 (t, J8.4 Hz, 1H), 8.02 (d, J=7.2 Hz, 1H), 8.07-8.11 (m, 2H), 8.19 (d, J=7.2 Hz, 1H), 8.33 (d, J=9. Hz, 1H), 8.43 (d, J=9.0 Hz, 1H), 8.76 (d, J=3.6 Hz, 1H), 11.26 (s, 1H). MS m/z 291.1321 [M+H]+.

TABLE 5

Selected data for compounds synthesised according to Scheme 5

| Compound | Structure | NMR | Mass Spec[M + H]+ |
|---|---|---|---|
| 76 | 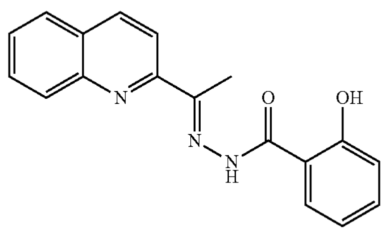 [SMILES: C/C(=N\NC(=O)c1ccccc1O)c1ccc2ccccc2n1] | $^1$H NMR (600 MHz, d6-DMSO) δ 2.56 (s, 3H), 7.00 (t, J = 7.2 Hz, 1H), 7.11 (d, J = 7.2 Hz, 1H), 7.44 (d, J = 7.2 Hz, 1H) 7.64 (t, J = 7.2 Hz, 1H), 7.81 (t, J = 7.2 Hz, 1H), 8.02 (d, J = 7.8 Hz, 2H), 8.09 (d, J = 8.4 Hz, 1H), 8.32 (d, J = 8.4 Hz, 1H), 8.45 (d, J = 8.4 Hz, 1H), 11.61 (s, 1H). | m/z 306.1399 |
| 77 | 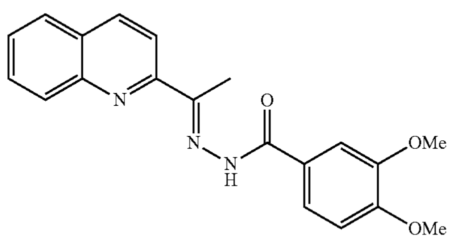 [SMILES: COc1ccc(C(=O)N/N=C(\C)c2ccc3ccccc3n2)cc1OC] | $^1$H NMR (600 MHz, d6-DMSO) some peaks are not well resolved δ 2.61 (s, 3H), 3.83 (s, 3H), 3.84 (s, 3H), 7.09 (d, J = 8.4 Hz, 1H), 7.49 (s, 1H), 7.58 (d, J = 7.2 Hz, 1H), 7.61-7.65 (m, 1H), 7.80 (t, J = 7.8 Hz, 1H), 8.01 (d, J = 7.8 Hz, 1H), 8.08 (d, J = 8.4 Hz, 1H), 8.24 (s, 1H), 8.39-8.43 (m, 1H), 10.82 (br s, 1H). | m/z 350.1635 |
| 78 | 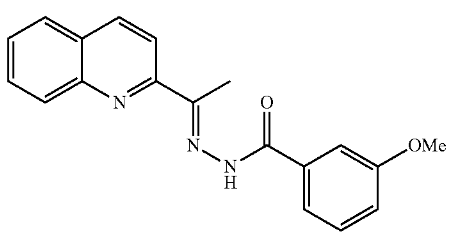 [SMILES: COc1cccc(C(=O)N/N=C(\C)c2ccc3ccccc3n2)c1] | $^1$H NMR (600 MHz, d6-DMSO) δ 2.60 (s, 3H), 3.86 (s, 3H), 7.18 (t, J = 8.4 Hz, 1H), 7.40-7.49 (m, 3H), 7.64 (t, J = 9.0 Hz, 1H), 7.80 (t, J = 9.0 Hz, 1H), 8.00 (d, J = 9.6 Hz, 1H), 8.09 (d, J = 9.6 Hz, 1H), 8.24-8.38 (m, 1H), 8.42 (br s, 1H), 11.00 (s, 1H). | m/z 320.1475 |
| 79 | 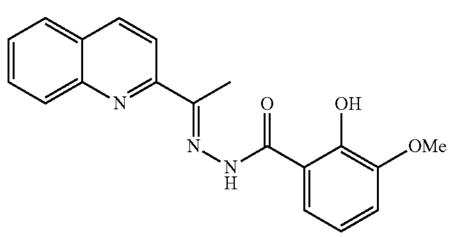 [SMILES: COc1cccc(C(=O)N/N=C(\C)c2ccc3ccccc3n2)c1O] | $^1$H NMR (500 MHz, d6-DMSO) δ 2.51 (s, 3H), 3.67 (s, 3H), 6.11 (t, J = 8.1 Hz, 2H), 6.64 (d, J = 7.5 Hz, 1H), 7.38 (d, J = 8.1 Hz, 1H), 7.57 (t, J = 8.4 Hz, 1H), 7.74 (t, J = 8.4 Hz, 1H), 7.95 (d, J = 8.1 Hz, 1H), 8.02 (d, J = 8.4 Hz, 1H), 8.32 (s, 2H) | m/z 336.1578 |
| 80 | 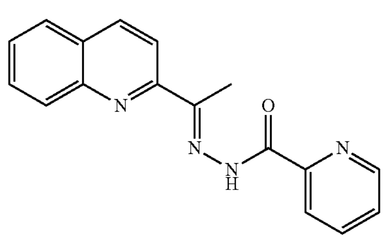 [SMILES: C/C(=N\NC(=O)c1ccccn1)c1ccc2ccccc2n1] | $^1$H NMR (600 MHz, d6-DMSO) δ 2.64 (s, 3H), 7.62-7.65 (m, 1H), 7.74-7.77 (m, 1H), 7.80 (t, J = 8.4 Hz, 1H), 8.02 (d, J = 7.2 Hz, 1H), 8.07-8.11 (m, 2H), 8.19 (d, J = 7.2 Hz, 1H), 8.33 (d, J = 9. Hz, 1H), 8.43 (d, J = 9.0 Hz, 1H), 8.76 (d, J = 3.6 Hz, 1H), 11.26 (s, 1H). | m/z 291.1321 |

TABLE 5-continued

Selected data for compounds synthesised according to Scheme 5

| Compound | Structure | NMR | Mass Spec[M + H]+ |
|---|---|---|---|
| 81 | 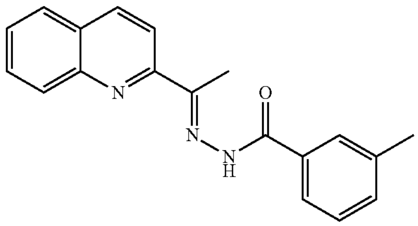 [SMILES: C/C(=N\NC(=O)c1cccc(C)c1)c1ccc2ccccc2n1] | $^1$H NMR (600 MHz, d6-DMSO) δ 2.41 (s, 3H), 2.60 (s, 3H), 7.40-7.44 (m, 2H), 7.62-7.80 (m, 4H), 7.99 (s, 1H), 8.06 (d, J = 8.4 Hz, 1H), 8.26-8.34 (m, 1H), 8.40 (s, 1H), 10.98 (br s, 1H). | m/z 304.1445 |
| 82 | 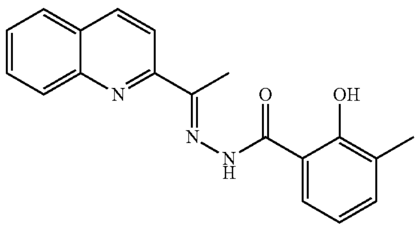 [SMILES: C/C(=N\NC(=O)c1cccc(C)c1O)c1ccc2ccccc2n1] | $^1$H NMR (600 MHz, d6-DMSO) δ 2.24 (s, 3H), 2.63 (s, 3H), 6.91 (t, J = 7.2 Hz, 1H), 7.38 (d, J = 6.6 Hz, 1H), 7.65 (t, J = 7.2 Hz, 1H), 7.81 (t, J = 7.2 Hz, 1H), 7.87 (s, 1H), 8.02 (d, J = 7.8 Hz, 1H), 8.35 (s, 1H), 8.43 (d, J = 7.8 Hz, 1H), ), 8.81 (d, J = 7.8 Hz, 1H), 11.39 (s, 1H). | m/z 320.1531 |
| 83 | 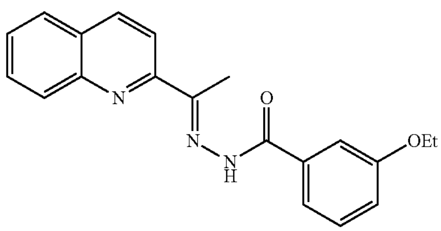 [SMILES: CCOc1cccc(C(=O)N/N=C(\C)c2ccc3ccccc3n2)c1] | $^1$H NMR (500 MHz, d6-DMSO) δ 1.37 (t, J = 7.2 Hz, 3H), 2.59 (s, 3H), 4.04 (q, J = 7.2 Hz, 2H), 7.11-7.16 (m, 1H), 7.38-7.51 (m, 3H), 7.63 (d, J = 7.2 Hz, 1H), 7.78 (d, J = 7.2 Hz, 1H), 7.95-8.02 (m, 1H), 8.04-8.09 (m, 1H), 8.17-8.24 (m, 1H), 8.41-8.45 (m, 1H), 11.01 (br s, 1H). | m/z 334.1549 |
| 84 | 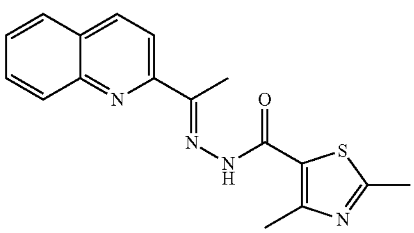 [SMILES: C/C(=N\NC(=O)c1sc(C)nc1C)c1ccc2ccccc2n1] | $^1$H NMR (600 MHz, d6-DMSO) δ 2.55 (s, 3H), 2.66 (s, 3H), 2.68 (s, 3H), 7.62-7.65 (m, 1H), 7.77-7.81 (m, 1H), 7.99-8.06 (m, 2H), 8.25 (d, J = 8.4 Hz, 1H), 8.44 (d, J = 8.4 Hz, 1H), 11.02 (br s, 1H). | m/z 325.1170 |
| 85 | 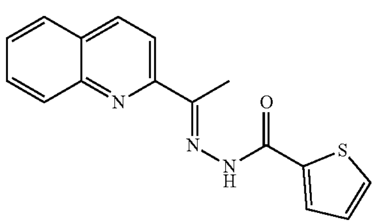 [SMILES: C/C(=N\NC(=O)c1cccs1)c1ccc2ccccc2n1] | $^1$H NMR (600 MHz, d6-DMSO) δ 2.59 (s, 3H), 7.25 (dd, J = 6.6, 4.2 Hz, 1H), 7.62-7.65 (m, 1H), 7.77-7.81 (m, 1H), 7.98-8.09 (m, 4H), 8.32-8.36 (m, 1H), 8.41-8.44 (m, 1H), 11.40 (br s, 1H). | m/z 296.0855 |
| 86 | 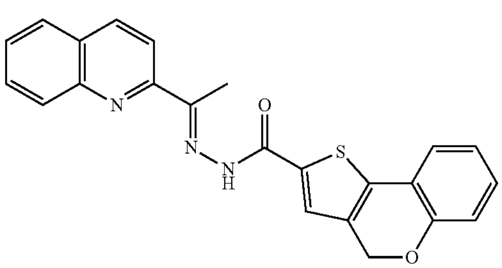 [SMILES: C/C(=N\NC(=O)c1cc2c(s1)-c1ccccc1OC2)c1ccc2ccccc2n1] | $^1$H NMR (600 MHz, d6-DMSO) δ 2.60 (s, 3H), 5.34 (s, 2H), 6.98 (d, J = 7.8 Hz, 1H), 7.04 (t, J = 7.8 Hz, 1H), 7.26 (t, J = 7.8 Hz, 1H), 7.48 (d, J = 6.6 Hz, 1H), 7.65 (t, J = 7.8 Hz, 1H), 7.81 (t, J = 7.8 Hz, 1H), 7.95 (s, 1H), 8.02 (d, J = 7.8 Hz, 1H), 8.08 (d, J = 7.8 Hz, 1H), 8.40 (br s, 1H), 8.53 (br s, 1H), 11.22 (br s, 1H). | m/z 400.11 |

TABLE 5-continued

Selected data for compounds synthesised according to Scheme 5

| Compound | Structure | NMR | Mass Spec[M + H]+ |
|---|---|---|---|
| 87 | 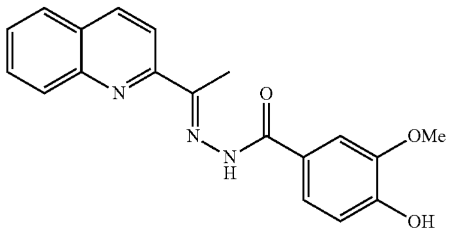 [SMILES: COc1cc(C(=O)N/N=C(\C)c2ccc3ccccc3n2)ccc1O] | 1H NMR (600 MHz, d6-DMSO) δ 2.59 (s, 3H), 3.85 (s, 3H), 6.89 (d, J = 7.8 Hz, 1H), 7.44-7.48 (m, 2H), 7.64 (d, J = 8.4 Hz, 1H), 7.89 (d, J = 8.4 Hz, 1H), 7.99 (d, J = 7.2 Hz, 1H), 8.06 (d, J = 8.4 Hz, 1H), 8.22-8.27 (m, 1H), 8.39 (d, J = 8.4 Hz, 1H), 10.94 (s, 1H). | m/z 336.1479 |
| 88 | 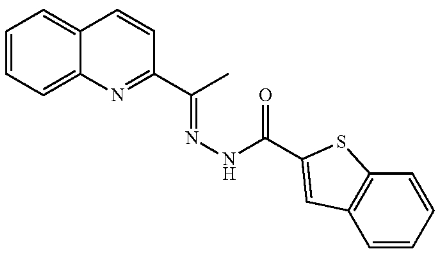 [SMILES: C/C(=N\NC(=O)c1cc2ccccc2s1)c1ccc2ccccc2n1] | 1H NMR (600 MHz, d6-DMSO) δ 2.64 (s, 3H), 7.05-7.38 (br m, 2H), 7.44-7.51 (m, 2H), 7.66 (s, 1H), 7.81 (s, 1H), 8.02-8.10 (m, 3H), 8.39-8.47 (m, 2H), 11.37 (br s, 1H). | m/z 346.1009 |
| 89 | 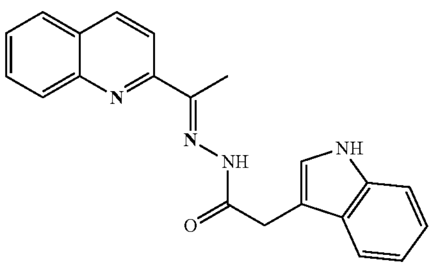 [SMILES: C/C(=N\NC(=O)Cc1c[nH]c2ccccc12)c1ccc2ccccc2n1] | 1H NMR (600 MHz, d6-DMSO) major regioisomer δ 2.54 (s, 3H), 4.22 (s, 2H), 6.95 (t, J = 7.8 Hz, 1H), 7.02-7.06 (m, 1H), 7.24 (s, 1H), 7.32-7.36 (m, 1H), 7.58-7.63 (m, 2H), 7.79 (d, J = 7.8 Hz, 1H), 8.01 (d, J = 7.8 Hz, 1H), 8.08-8.14 (m, 1H), 8.35 (d, J = 7.8 Hz, 1H), 8.42 (s, 1H), 10.81 (s, 1H), 10.89 (s, 1H). | m/z 343.1738 |
| 90 | 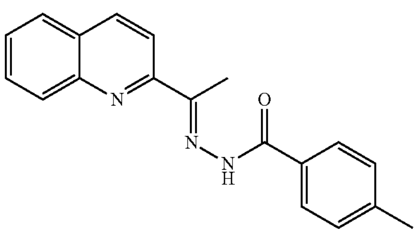 [SMILES: C/C(=N\NC(=O)c1ccc(C)cc1)c1ccc2ccccc2n1] | 1H NMR (600 MHz, d6-DMSO) δ 2.39 (s, 3H), 2.58 (s, 3H), 7.31-7.36 (m, 2H), 7.59-7.63 (m, 1H), 7.77-7.91 (m, 3H), 7.95-8.03 (m, 2H), 8.24-8.40 (m, 2H), 10.87 (br s, 1H). | m/z 304.1444 |
| 91 | 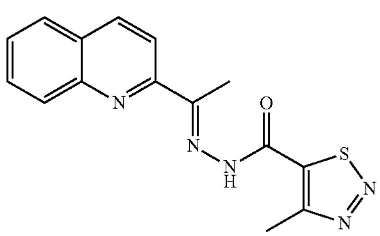 [SMILES: C/C(=N\NC(=O)c1snnc1C)c1ccc2ccccc2n1] | 1H NMR (600 MHz, d6-DMSO) δ 2.61 (s, 3H), 2.99 (s, 3H), 7.67 (d, J = 7.2 Hz, 1H), 7.81 (s, 1H), 8.02-8.06 (m, 2H), 8.23 (d, J = 8.4 Hz, 1H), 8.53 (d, J = 8.4 Hz, 1H), 11.79 (s, 1H). | m/z 312.0914 |
| 92 | 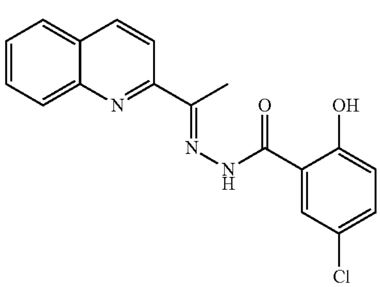 [SMILES: C/C(=N\NC(=O)c1cc(Cl)ccc1O)c1ccc2ccccc2n1] | | m/z 340.0848 |

TABLE 5-continued

Selected data for compounds synthesised according to Scheme 5

| Compound | Structure | NMR | Mass Spec[M + H]+ |
|---|---|---|---|
| 160 | 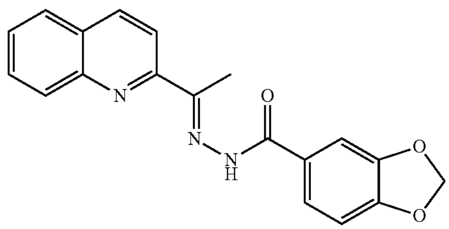 [SMILES: C/C(=N\NC(=O)c1ccc2c(c1)OCO2)c1ccc2ccccc2n1] | | m/z 334.1187 |
| 161 | 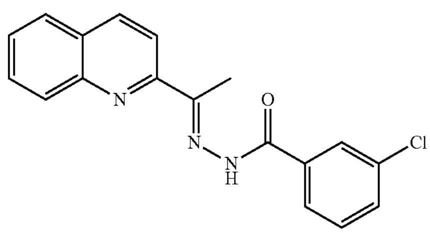 [SMILES: C/C(=N\NC(=O)c1cccc(Cl)c1)c1ccc2ccccc2n1] | $^1$H NMR (500 MHz, d6-DMSO) δ 2.62 (s, 3H), 7.58 (t, J = 8.0 Hz, 1H), 7.64 (t, J = 7.0 Hz 1H), 7.68 (d, J = 8.0 Hz, 1H), 7.79 (t, J = 8.0 Hz, 1H), 7.89 (br s, 1H), 7.97 (br s, 1H), 8.00 (br s, 1H), 8.31 (br s, 1H), 8.41 (br s, 1H), 11.08 (s, 1H). | m/z 324.0897 |
| 162 | 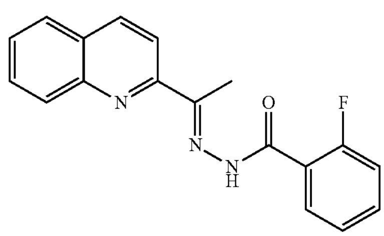 [SMILES: C/C(=N\NC(=O)c1ccccc1F)c1ccc2ccccc2n1] | | m/z 308.1191 |

A range of fused heterocyclic and heterocyclic substituted acyl hydrazones could be synthesised as outlined in Scheme 6. Starting ketone/aldehyde K is defined below in Scheme 6. Heating heterocyclic or fused heterocyclic ketone/aldehyde K with an appropriate ketohydrazide in the presence of catalytic acid and a suitable solvent provided the target compounds L.

Scheme 6

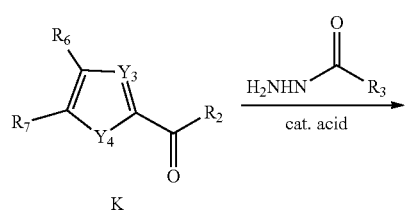

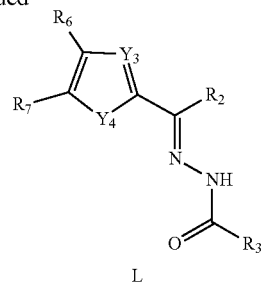

Y3 is CR8, NR5 or S and
Y4 is CR8 or N, provided both Y3 and Y4 are not CR8.
R6 and R7 taken together with atoms to which they are attached, form a 6 membered aryl or heteroaryl ring.
R2 is selected from hydrogen or alkyl
R3 is alkyl, aryl, heteroaryl

Example 6

(E)-4-Methyl-N'-(1-(4-methylthiazol-2-yl)ethylidene)-1,2,3-thiadiazole-5-carbohydrazide (100)

4-Methyl-2-acetylthiazole (76 mg) was heated together with 4-methyl-1,2,3-thiadiazole-5-carbohydrazide (81 mg) in EtOH (7 mL) at 65° C. Concentrated hydrochloric acid (2 drops) were added and the reaction was heated for 1.5 h. After cooling to rt, a pale yellow solid precipitated out of solution and was collected by filtration to afford 100 (124 mg). $^1$H NMR (600 MHz, d6-DMSO) δ 2.42 (s, 3H), 2.50 (s, 3H), 2.97 (s, 3H), 7.48 (s, 1H), 11.85 (s, 1H). MS m/z 282.0477[M+H]$^+$.

TABLE 6

Selected data for compounds synthesised according to Scheme 6

| Compound | Structure | NMR | Mass Spec [M + H]$^+$ |
|---|---|---|---|
| 93 | 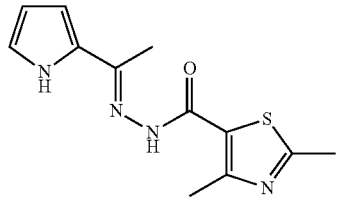 | $^1$H NMR (600 MHz, d6-DMSO) δ 2.29 (s, 3H), 2.96 (s, 3H), 6.18 (s, 3H), 6.70 (s, 1H), 7.02 (s, 1H), 10.90 (s, 1H), 11.30 (s, 1H). | m/z 250.0463 |
| 94 | 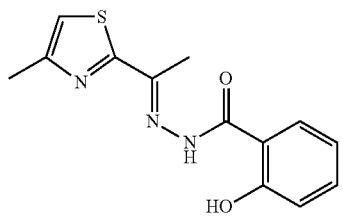 [SMILES: C/C(=N\NC(=O)c1ccccc1O)c1nc(C)cs1] | $^1$H NMR (600 MHz, d6-DMSO) δ 2.40 (s, 3H), 2.43 (s, 3H), 6.99 (s, 1H), 7.07 (d, J = 8.4 Hz, 1H), 7.36 (s, 1H), 7.44 (s, 1H), 7.98 (d, J = 7.2 Hz, 1H), 11.46 (s, 1H), 11.85 (s, 1H). | m/z 276.0802 |
| 95 | 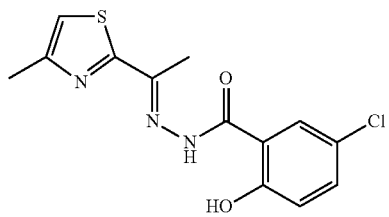 [SMILES: C/C(=N\NC(=O)c1cc(Cl)ccc1O)c1nc(C)cs1] | $^1$H NMR (600 MHz, d6-DMSO) δ 2.39 (s, 3H), 2.42 (s, 3H), 7.05 (d, J = 9.0 Hz, 1H), 7.37 (s, 1H), 7.46-7.49 (m, 1H), 7.89 (s, 1H), 11.42 (s, 1H), 12.03 (br s, 1H). | m/z 310.12 |
| 96 | 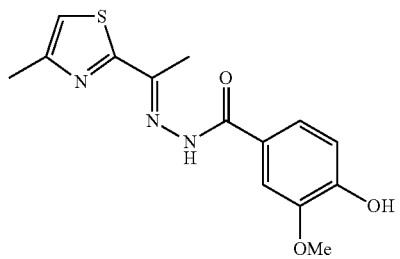 [SMILES: COc1cc(C(=O)N/N=C(\C)c2nc(C)cs2)ccc1O] | $^1$H NMR (600 MHz, d6-DMSO) δ 2.44 (s, 3H), 2.55 (s, 3H), 3.86 (s, 3H), 6.94 (d, J = 8.4 Hz, 1H), 7.30-7.34 (m, 2H), 7.68 (s, 1H), 9.87 (s, 1H). | m/z 306.0906 |
| 97 | 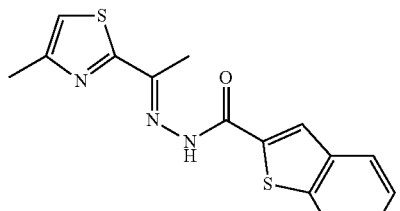 | $^1$H NMR (600 MHz, d6-DMSO) δ 2.37 (s, 3H), 2.41 (s, 3H), 7.38-7.52 (m, 3H), 8.02 (d, J = 7.8 Hz, 1H), 8.05 (d, J = 7.8 Hz, 1H), 8.41 (s, 1H). | m/z 316.0591 |

TABLE 6-continued

Selected data for compounds synthesised according to Scheme 6

| Compound | Structure | NMR | Mass Spec [M + H]+ |
|---|---|---|---|
| 98 | | ¹H NMR (600 MHz, d6-DMSO) δ 2.41 (s, 3H), 2.48 (s, 3H), 3.00 (s, 6H), 6.80 (d, J = 9.0 Hz, 2H), 7.67 (s, 1H), 7.77 (d, J = 9.0 Hz, 2H). | m/z 303.1273 |
| 99 | | ¹H NMR (600 MHz, d6-DMSO) δ 2.45 (s, 3H), 2.58 (s, 3H), 3.85 (s, 3H), 3.86 (s, 3H), 7.16 (d, J = 8.4 Hz, 1H), 7.46 (s, 1H), 7.53 (t, J = 8.4 Hz, 1H), 7.70 (s, 1H). | m/z 320.1061 |
| 100 | | ¹H NMR (600 MHz, d6-DMSO) δ 2.42 (s, 3H), 2.50 (s, 3H), 2.97 (s, 3H), 7.48 (s, 1H), 11.85 (s, 1H). | m/z 282.0477 |
| 101 | | ¹H NMR (600 MHz, d6-DMSO) δ 2.40 (s, 3H), 2.44 (s, 3H), 5.31 (s, 2H), 6.97 (dd, J = 6.6, 9.6 Hz, 1H), 7.03 (dt, J = 1.8, 9.0 Hz, 1H), 7.24-7.28 (m, 1H), 7.40-7.44 (m, 2H), 7.88 (s, 1H), 10.74 (br s, 1H). | m/z 370.0680 |
| 102 | | ¹H NMR (600 MHz, d6-DMSO) δ 2.36 (s, 3H), 2.46 (s, 3H), 2.96 (s, 3H), 6.85 (d, J = 3.6 Hz, 1H), 7.41 (d, J = 3.6 Hz, 1H), 11.48 (s, 1H). | m/z 281.05 |
| 103 | | ¹H NMR (600 MHz, d6-DMSO) δ 2.29 (s, 3H), 2.33 (s, 3H), 2.45 (s, 3H), 6.81-6.86 (m, 2H), 7.32-7.37 (m, 2H), 7.76 (d, J = 9.6 Hz, 1H), 11.05 (s, 1H), 12.17 (br s, 1H). | m/z 289.1008 |

TABLE 6-continued

Selected data for compounds synthesised according to Scheme 6

| Compound | Structure | NMR | Mass Spec [M + H]+ |
|---|---|---|---|
| 104 | | $^1$H NMR (600 MHz, d6-DMSO) δ 2.52 (s, 3H), 6.99-7.07 (m, 2H), 7.44-7.53 (m, 3H), 7.99-8.12 (m, 3H), 11.62 (s, 1H), 11.81 (s, 1H). | m/z 312.0857 |
| 105 | | $^1$H NMR (600 MHz, d6-DMSO) δ 2.23 (s, 3H), 2.59 (s, 3H), 6.91 (t, J = 7.8 Hz, 1H), 7.38 (d, J = 6.6 Hz, 1H), 7.48-7.56 (m, 2H), 7.82 (s, 1H), 8.05 (d, J = 7.8 Hz, 1H), 8.12 (d, J = 7.8 Hz, 1H), 11.47 (s, 1H), 11.58 (brs, 1H). | m/z 326.0958 |
| 106 | | $^1$H NMR (600 MHz, d6-DMSO) δ 2.20 (s, 3H), 2.37 (s, 3H), 2.51 (s, 3H), 7.41 (d, J = 4.2 Hz, 2H), 7.68-7.72 (m, 2H), 8.55 (s, 1H), 12.08 (s, 1H). | m/z 274.1007 |
| 107 | | $^1$H NMR (600 MHz, d6-DMSO) δ 2.28 (s, 3H), 2.37 (s, 3H), 3.82 (s, 3H), 7.17 (d, J = 7.2 Hz, 1H), 7.40-7.46 (m, 3H), 8.52 (s, 1H), 12.01 (s, 1H). | mz 290.0955 |
| 108 | | | m/z 248.0517 |
| 109 | | $^1$H NMR (600 MHz, d6-DMSO) δ 7.01 (d, J = 8.4 Hz, 1H), 7.46 (dd, J = 8.4, 2.4 Hz, 1H), 7.81 (d, J = 2.4 Hz, 1H), 7.87 (s, 1H), 7.98 (d, J = 2.4 Hz, 1H), 8.65 (s, 1H), 11.55 (brs, 1H), 12.06 (s, 1H). | m/z 282.0982 |
| 110 | | $^1$H NMR (600 MHz, d6-DMSO) δ 3.96 (s, 3H), 6.93 (d, J = 8.4 Hz, 2H), 6.96 (s, 1H), 7.35 (s, 1H), 7.40-7.45 (m, 1H), 7.84 (d, J = 5.4 Hz, 1H), 8.41 (s, 1H), 11.92 (s, 1H). | m/z 245.1050 |
| 111 | | $^1$H NMR (600 MHz, d6-DMSO) δ 2.17 (s, 3H), 4.00 (s, 3H), 6.80 (t, J = 7.8 Hz, 1H), 7.19 (s, 1H), 7.37 (d, J = 7.2 Hz, 1H), 7.47 (s, 1H), 7.62 (d, J = 7.2 Hz, 1H), 8.56 (s, 1H). | m/z 259.1179 |

TABLE 6-continued

Selected data for compounds synthesised according to Scheme 6

| Compound | Structure | NMR | Mass Spec [M + H]+ |
|---|---|---|---|
| 112 | 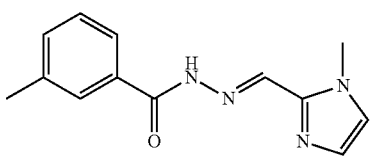 [SMILES: Cc1cccc(C(=O)N/N=C/c2nccn2C)c1] | ¹H NMR (600 MHz, d6-DMSO) δ 2.39 (s, 3H), 4.00 (s, 3H), 7.4 (d, J = 7.8 Hz, 2H), 7.71 (s, 1H), 7.80-7.85 (m, 3H), 8.80 (s, 1H), 12.88 (br s, 1H). | m/z 243.1241 |
| 113 | 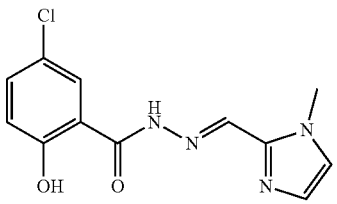 [SMILES: Cn1ccnc1/C=N/NC(=O)c1cc(Cl)ccc1O] | ¹H NMR (600 MHz, d6-DMSO) δ 3.96 (s, 3H), 6.99 (d, J = 9.0 Hz, 1H), 7.06 (s, 1H), 7.36 (s, 1H), 7.45 (dd, J = 9.0, 2.4 Hz, 1H), 7.86 (d, J = 2.4 Hz, 1H), 8.40 (s, 1H). | m/z 279.0651 |
| 114 | 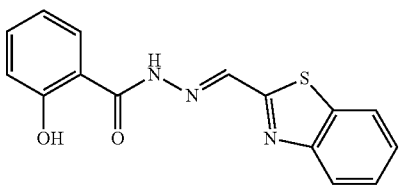 [SMILES: O=C(N/N=C/c1nc2ccccc2s1)c1ccccc1O] | ¹H NMR (600 MHz, d6-DMSO) δ 6.96-7.01 (m, 2H), 7.44-7.55 (m, 3H), 7.82 (d, J = 1.2 Hz, 1H), 8.05 (d, J = 7.2 Hz, 1H), 8.15 (d, J = 7.2 Hz, 1H), 8.77 (s, 1H), 11.41 (s, 1H), 12.42 (s, 1H). | m/z 298.0686 |
| 115 | 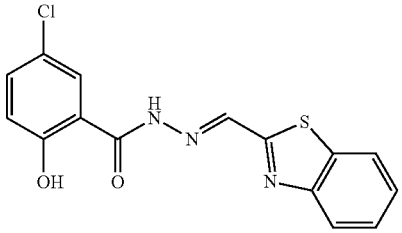 [SMILES: O=C(N/N=C/c1nc2ccccc2s1)c1cc(Cl)ccc1O] | ¹H NMR (600 MHz, d6-DMSO) δ 7.03 (d, J = 9.0 Hz, 1H), 7.47-7.56 (m, 3H), 7.81 (d, J = 3.0 Hz, 1H), 7.96 (d, J = 7.8 Hz, 1H), 8.15 (d, J = 7.8 Hz, 1H), 8.74 (s, 1H), 11.43 (br s, 1H), 12.22 (s, 1H). | m/z 332.0253 |
| 116 | 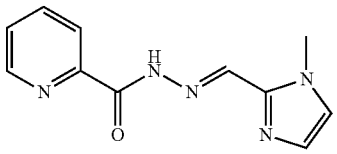 [SMILES: Cn1ccnc1/C=N/NC(=O)c1ccccn1] | ¹H NMR (600 MHz, d6-DMSO) δ 4.02 (s, 3H), 7.70-7.74 (m, 2H), 7.77 (s,1H), 8.06-8.15 (m, 2H), 8.74 (d, J = 7.2 Hz, 1H), 8.85 (s, 1H), 12.97 (s, 1H). | m/z 230.1032 |
| 117 | 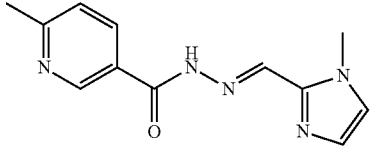 [SMILES: Cc1ccc(C(=O)N/N=C/c2nccn2C)cn1] | ¹H NMR (600 MHz, d6-DMSO) δ 2.58 (s, 3H), 4.02(s, 3H), 7.69 (d, J = 6.6 Hz, 1H), 7.67 (s, 1H), 7.79 (s, 1H), 8.30 (s, 1H), 8.73 (s, 1H), 9.06 (s, 1H), 12.97 (s, 1H). | m/z 244.1193 |
| 118 | 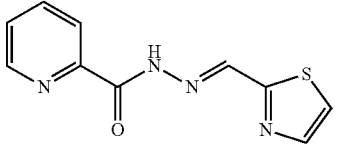 [SMILES: O=C(N/N=C/c1nccs1)c1ccccn1] | ¹H NMR (600 MHz, d6-DMSO) δ 7.68 (t,J = 8.4 Hz, 1H), 7.85 (s, 1H), 7.95 (s, 1H), 8.06 (t, J = 7.2 Hz, 1H), 8.13 (d, J = 7.2 Hz, 1H), 8.72 (d,./ 2.4 Hz. 1H), 8.88 (s, 1H), 12.62 (s, 1H). | m/z 233.0492 |
| 119 | 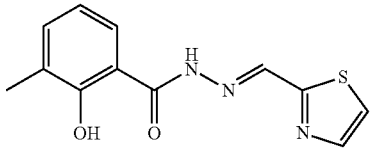 [SMILES: Cc1cccc(C(=O)N/N=C/c2nccs2)c1O] | ¹H NMR (600 MHz, d6-DMSO) δ 2.17(s, 3H), 6.87 (t, J = 9.0 Hz, 1H), 7.39 (d, J = 7.2 Hz, 1H), 7.88 (dd, J = 13.2, 8.4 Hz, 1H), 7.98 (s, 1H), 8.80 (s, 1H), 12.39 (brs, 1H), 12.46 (s, 1H). | m/z 262.0646 |

TABLE 6-continued

Selected data for compounds synthesised according to Scheme 6

| Compound | Structure | NMR | Mass Spec [M + H]+ |
|---|---|---|---|
| 163 | | | m/z 230.1034 |
| 164 | | | m/z 273.1346 |
| 165 | | $^1$H NMR (500 MHz, d6-DMSO) δ 4.01 (s, 3H), 7.56-7.62 (m, 1H), 7.70-7.74 (m, 2H), 7.83 (br s, 1H), 7.96-8.00 (m, 1H), 8.07 (s, 1H), 8.77 (s, 1H), 13.01 (s, 1H). | m/z 263.0692 |
| 166 | | $^1$H NMR (500 MHz, d6-DMSO) δ 3.97 (s, 3H), 7.24 (t, J = 4.5 Hz, 1H), 7.42 (s, 1H), 7.59 (s, 1H), 7.93 (d, J = 4.5 Hz, 1H), 8.04 (s, 1H), 8.58 (s, 1H), 12.51 (s, 1H). | m/z 235.06 |
| 167 | | $^1$H NMR (500 MHz, d6-DMSO) δ 2.48 (s, 3H), 3.94 (s, 3H), 6.67 (s, 1H), 7.24 (s, 1H), 7.48 (s, 1H), 8.51 (s, 1H), 12.47 (s, 1H). | m/z 234.10 |
| 168 | | | m/z 251.0709 |
| 169 | | | m/z 273.0980 |

Similarly, imidazopyridine derivatives were synthesised according to Scheme 7.

Scheme 7

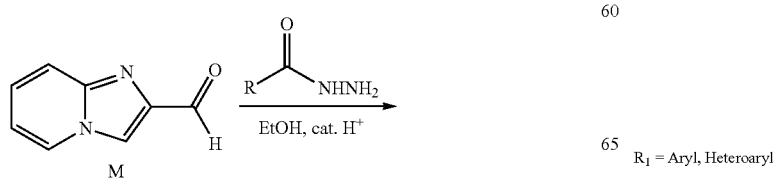

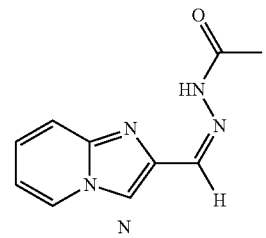

$R_1$ = Aryl, Heteroaryl

Example 7

(Z)—N'-(Imidazo[1,2-a]pyridin-2-ylmethylene)-3-methoxybenzohydrazide (120)

Imidiazo[1,2-a]pyridine-2-carboxaldehyde (101 mg) and 3-methoxybenzohydrazide (114 mg) were heated to reflux in EtOH (7 mL) in the presence of concentrated hydrochloric acid for 2 h. The reaction was allowed to cool and the resulting white precipitate was collected by filtration to afford (Z)—N'-(imidazo[1,2-a]pyridin-2-ylmethylene)-3-methoxybenzohydrazide 120 (61 mg) as an off-white solid. $^1$H NMR (600 MHz, d6-DMSO) δ 3.85 (s, 3H), 7.19 (dd, J=8.4, 2.4 Hz, 1H), 7.44-7.48 (m, 2H), 7.56-7.60 (m, 2H), 7.85 (d, J=3.0 Hz, 1H), 7.93 (t, J=7.8 Hz, 1H), 8.73 (s, 1H), 8.89 (d, J=6.0 Hz, 1H), 8.91 (s, 1H), 12.62 (s, 1H). MS m/z 295.1191[M+H]$^+$.

TABLE 7

NMR and MS Data for compounds synthesised via Scheme 7.

| Compound | Structure | NMR | Mass Spec [M + H]$^+$ |
|---|---|---|---|
| 121 | (3-methylbenzoyl hydrazone of imidazo[1,2-a]pyridine-2-carbaldehyde) | $^1$H NMR (600 MHz, d6-DMSO) δ 2.39 (s, 3H), 7.42-7.49 (m, 3H), 7.80-7.86 (m, 3H), 7.94 (t, J = 7.8 Hz, 1H), 8.72-8.76 (m, 2H), 8.91 (d, J = 6.6 Hz, 1H), 12.56 (s, 1H). | m/z 279.1242 |
| 138 | (benzothiophene-2-carbonyl hydrazone of imidazo[1,2-a]pyridine-2-carbaldehyde) | $^1$H NMR (600 MHz, d6-DMSO) δ 7.42-7.53 (m, 3H), 7.86 (br s, 1H), 7.92 (s, 1H), 8.00-8.08 (m, 2H), 8.46 (s, 1H), 8.74 (s, 1H), 8.90 (d, J = 6.0 Hz, 1H), 11.98 (br s, 1H), 12.90 (s, 1H). | m/z 321.1164 |
| 139 | (2-hydroxybenzoyl hydrazone of imidazo[1,2-a]pyridine-2-carbaldehyde) | $^1$H NMR (600 MHz, d6-DMSO) δ 6.94-7.03 (m, 3H), 7.35-7.45 (m, 2H), 7.61 (d, J = 9.0 Hz, 1H), 7.88 (d, J = 7.2 Hz, 1H), 8.41 (s, 1H), 8.54 (s, 1H), 8.61 (d, J = 3.6 Hz, 1H), 11.81 (s, 1H), 11.96 (s, 1H). | m/z 281.1391 |

A variety of dipyridyl acyl hydrazones were synthesised according to Scheme 8. Dimethyldipyridyl ketone O was heated together with substituted arylbenzhydrazides to afford target acyl hydrazones P.

Scheme 8

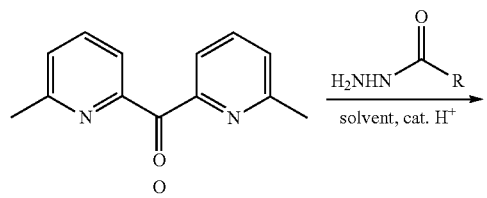

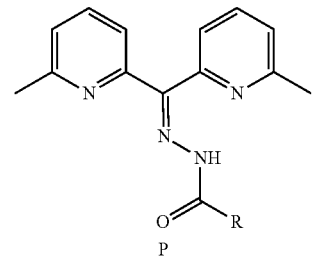

Example 8

N'-(bis(6-Methylpyridin-2-yl)methylene)-4-hydroxy-3-methoxybenzohydrazide (130)

Bis(6-methylpyridin-2-yl)methanone (227 mg) and vanillic acid hydrazide (195 mg) in EtOH (10 mL) were treated with 2 drops of concentrated hydrochloric acid and the reaction was heated to 60° C. for 1 h. The reaction was allowed to cool and a yellow solid was collected by filtration to afford N'-(bis(6-methylpyridin-2-yl)methylene)-4-hydroxy-3-methoxybenzohydrazide 130 (248 mg) as a beige solid. $^1$H NMR (600 MHz, d6-DMSO) δ 2.61 (s, 3H), 2.70 (s, 3H), 3.84 (s, 3H), 6.98 (d, J=8.4 Hz, 1H), 7.31 (d, J=8.4 Hz, 1H), 7.41-7.45 (m, 2H), 7.55 (d, J=7.8 Hz, 1H), 7.64 (s, 1H), 7.83 (d, J=7.8 Hz, 1H), 7.97 (d, J=7.8 Hz, 1H), 8.16 (s, 1H), 10.02 (br s, 1H), 15.25 (br s, 1H). MS m/z 377.1611 [M+H]$^+$.

In a further example, a phenolic hydrazone derivative 184 could be converted to the dimethylaminomethyl compound 185 by the action of tetramethylenediamine in refluxing toluene (see example 8a below).

Example 8a 5-chloro-N'-(di(pyridin-2-yl)methylene)-3-((dimethylamino)methyl)-2-hydroxybenzohydrazide (185)

5-chloro-N'-(di(pyridin-2-yl)methylene)-2-hydroxybenzohydrazide 184 (801 mg, 2.27 mmol) was suspended in toluene (95 mL) and treated with N, N, N, N,-tetramethylenediamine (4 mL). The reaction was heated to reflux for 4 h, then allowed to cool to rt o/n. Volatiles were removed in vacuo and the resulting residue was taken up in acetonitrile (4 mL) then ether (20 mL) was added slowly. The resulting precipitate was collected by filtration to afford 5-chloro-N'-(di(pyridin-2-yl)methylene)-3-((dimethylamino)methyl)-2-hydroxybenzohydrazide (747 mg) as a yellow solid. $^1$H NMR (600 MHz, d6-DMSO) δ 2.60 (s, 6H), 3.98 (s, 2H), 7.12 (s, 1H), 7.37-7.43 (m, 2H), 7.51 (d, J=6.0 Hz, 1H), 7.69 (s, 1H), 7.90-7.94 (m, 2H), 8.14 (d, J=9.6 Hz, 1H), 8.46 (s, 1H), 8.76-8.78 (m, 1H), 8.60 (br s, 1H), 8.76 (14.48 (s, 1H). MS m/z 410.2014[M+H]$^+$.

TABLE 8

MS Data for compounds synthesised according to Scheme 8

| Compound | Structure | Mass Spectrometry [M + H]$^+$ |
|---|---|---|
| 122 | 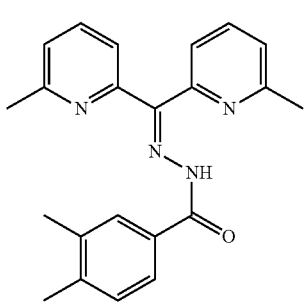 | m/z 345.1892 |
| 123 | 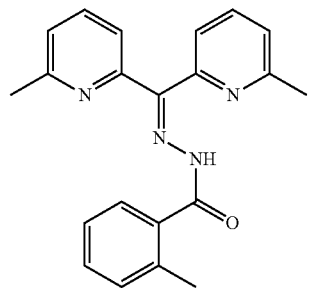 | m/z 374.18 |
| 124 | 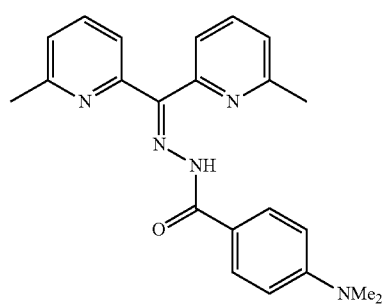 | m/z 359.27 |
| 125 | 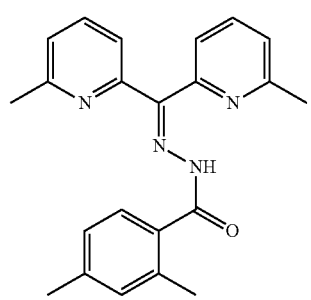 | m/z 359.19 |
| 126 | 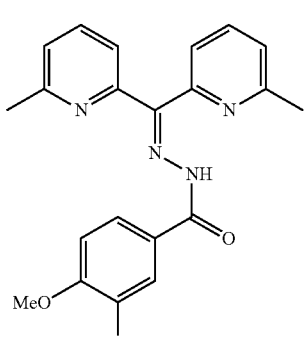 | m/z 391.1913 |
| 127 | 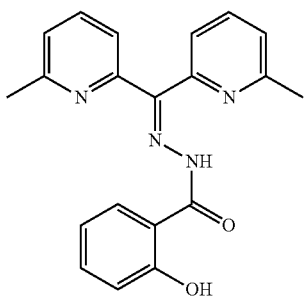 | m/z 347.1744 |
| 128 | 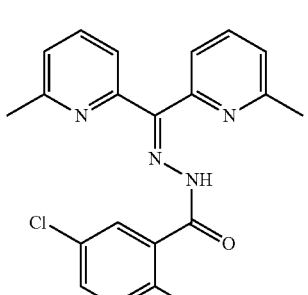 | m/z 381.1627 |

TABLE 8-continued

MS Data for compounds synthesised according to Scheme 8

| Compound | Structure | Mass Spectrometry [M + H]+ |
|---|---|---|
| 129 | bis(6-methylpyridin-2-yl)methylene hydrazide of 2-hydroxy-3-methylbenzoic acid | m/z 361.1789 |
| 131 | bis(6-methylpyridin-2-yl)methylene hydrazide of 3-methoxybenzoic acid | m/z 361.1160 |
| 132 | bis(6-methylpyridin-2-yl)methylene hydrazide of 3-ethoxybenzoic acid | m/z 375.1816 |
| 133 | bis(6-methylpyridin-2-yl)methylene hydrazide of 3-methylbenzoic acid | m/z 345.17 |
| 134 | bis(6-methylpyridin-2-yl)methylene hydrazide of 2-fluorobenzoic acid | m/z 349.1459 |
| 135 | bis(6-methylpyridin-2-yl)methylene hydrazide of picolinic acid | m/z 332.1506 |
| 136 | bis(6-methylpyridin-2-yl)methylene hydrazide of 5-methylisoxazole-3-carboxylic acid | m/z 336.1455 |
| 137 | bis(6-methylpyridin-2-yl)methylene hydrazide of 2,4-dimethylthiazole-5-carboxylic acid | m/z 366.1384 |
| 140 | bis(6-methylpyridin-2-yl)methylene hydrazide of 4-(trifluoromethyl)benzoic acid | m/z 399.1429 |

TABLE 8-continued

MS Data for compounds synthesised according to Scheme 8

| Compound | Structure | Mass Spectrometry [M + H]+ |
|---|---|---|
| 141 | 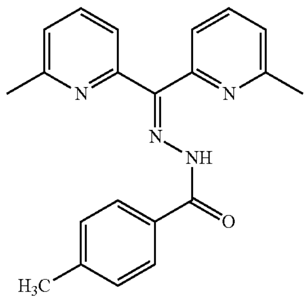 | m/z 345.17 |
| 142 | 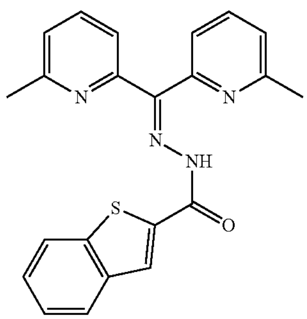 | m/z 387.1275 |
| 143 | 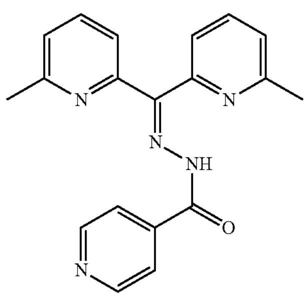 | m/z 332.1993 |
| 144 | 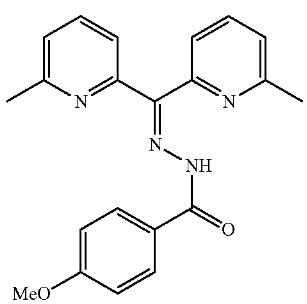 | m/z 361.1660 |
| 154 | 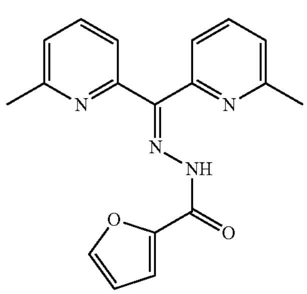 | m/z 321.1346 |
| 155 | | m/z 346.1666 |
| 181 | | m/z 375.1451 |
| 182 | | m/z 353.1181 |
| 183 | | m/z 332.1506 |

TABLE 8-continued

MS Data for compounds synthesised according to Scheme 8

| Compound | Structure | Mass Spectrometry [M + H]+ |
|---|---|---|
| 184 | 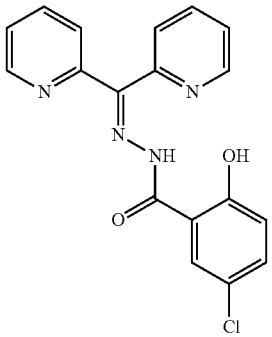 [SMILES: O=C(NN=C(c1ccccn1)c1ccccn1)c1cc(Cl)ccc1O] | m/z 381.1627 |
| 185 | 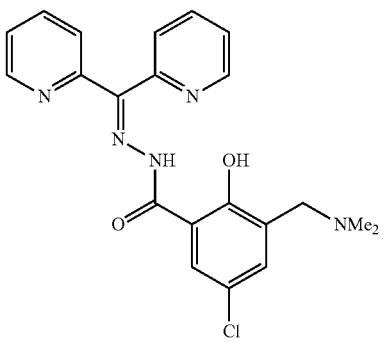 [SMILES: CN(C)Cc1cc(Cl)cc(C(=O)NN=C(c2ccccn2)c2ccccn2)c1O] | m/z 410.2014 |
| 186 | 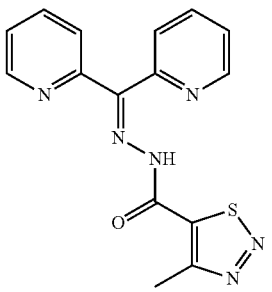 [SMILES: Cc1nnsc1C(=O)NN=C(c1ccccn1)c1ccccn1] | m/z 325.1081 |
| 187 | 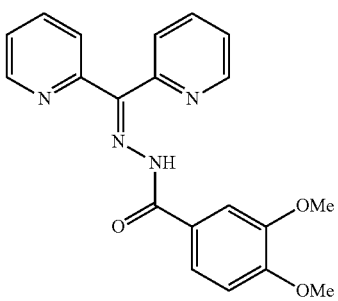 [SMILES: COc1ccc(C(=O)NN=C(c2ccccn2)c2ccccn2)cc1OC] | m/z 363.1684 |
| 188 | 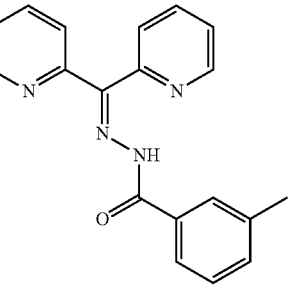 | m/z 317.1400 |
| 189 | 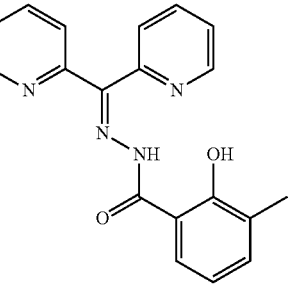 | m/z 333.1347 |
| 190 | 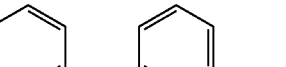 | m/z 349.1296 |
| 191 | 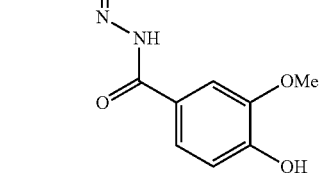 | m/z 361.1661 |

Acrylonitrile derivatives could be synthesised as outlined in Scheme 9 below

Quinolone ketone could be converted to the acetocyanohydrazide Q by allowing to react with 2-cyanoacetohydrazide under standard conditions. Intermediate Q is then allowed to react with an aldehyde in the presence of catalytic piperidine to afford the required acrylonitrile derivative R.

Scheme 9

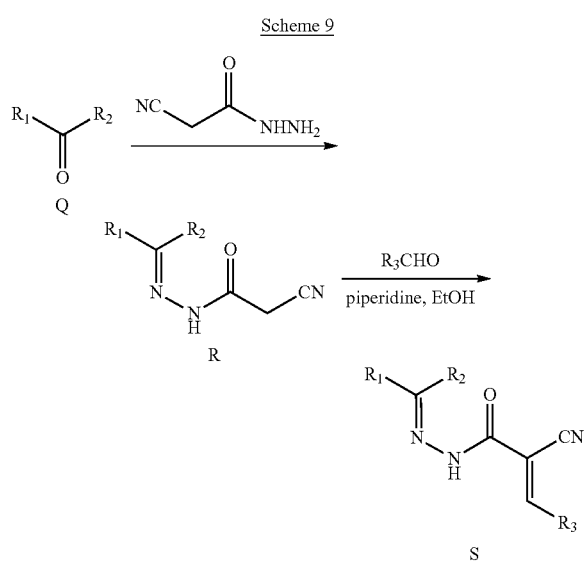

R1, R2 = pyridyl or 2-methylpyridyl
R1 = pyridyl,
R2 = H,
R1, R2 = fused quinolone

Synthesis of (E)-2-cyano-N'-(6,7-dihydroquinolin-8(5H)-ylidene)acetohydrazide To a mixture of 6,7 dihydroquinolin-8-one (906 mg) Q ($R_1$, $R_2$=fused quinoline), acetocyanohydrazide (712 mg) in EtOH (40 mL) was added conc. hydrochloric acid (3 drops) and the reaction was heated to 50° C. for 1 h. After cooling to rt, (E)-2-cyano-N'-(6,7-dihydroquinolin-8(5H)-ylidene) acetohydrazide R ($R_1$, $R_2$=fused quinoline) precipitated out of solution as a tan solid. The solid was collected by filtration and dried at the pump to afford 1.2 g of material. MS m/z 229.1081 [M+H]$^+$.

Example 9

(2E,N'E)-2-Cyano-N'-(6,7-dihydroquinolin-8(5H)-ylidene)-3-(2-hydroxyphenyl) acrylohydrazide 145

To a mixture of the (E)-2-cyano-N'-(6,7-dihydroquinolin-8(5H)-ylidene)acetohydrazide (70 mg) R (179) in EtOH (8 mL) was added salicylaldehyde (110 μL). This was followed by the addition of a 0.1M solution of piperidine in EtOH (0.2 mL) with vigorous stirring at room temp and gentle heating to get all into solution. After 30 min, a pale yellow solid was collected by filtration and washed with EtOH (×3). After drying 17 mg of (2E,N'E)-2-cyano-N'-(6,7-dihydroquinolin-8(5H)-ylidene)-3-(2-hydroxyphenyl)acrylohydrazide S (145) was obtained. $^1$H NMR (600 MHz, d6-DMSO) δ 1.89 (t, J=6.0 Hz, 2H), 2.70 (t, J=6.0 Hz, 2H), 2.80 (t, J=6.0 Hz, 2H), 7.24-7.31 (m, 3H), 7.58 (dt, J=8.4, 1.2 Hz, 1H), 7.62 (d, J=8.4 Hz, 1H), 7.82 (dd, J=7.8, 1.2 Hz, 1H), 8.50 (dd, J=4.8, 1.2 Hz, 1H), 8.64 (s, 1H), 9.27 (s, 1H), 13.53 (s, 1H). MS m/z 333.1347 [M+H]$^+$.

TABLE 9

Selected data for compounds synthesised according to Scheme 9

| Compound | Structure | NMR | Mass Spec [M + H]$^+$ |
|---|---|---|---|
| 170 | (tetrahydroquinoline hydrazone with 2-hydroxy-5-fluorophenyl acrylonitrile) | $^1$H NMR (500 MHz, d6-DMSO) δ 1.91 (t, J = 6.0 Hz, 2H), 2.72 (t, J = 6.0 Hz, 2H), 2.82 (t, J = 6.0 Hz, 2H), 7.29-7.34 (m, 2H), 7.45 (dt, J = 8.5, 3.0 Hz, 2H), 7.65 (d, J = 7.5 Hz, 1H), 7.74 (dd, J = 8.5, 3.0 Hz), 8.53 (d, J = 3.5 Hz, 1H), 8.64 (s, 1H), 9.37 (s, 1H), 13.51 (s, 1H). | m/z 351.1251 |
| 179 (R) | (tetrahydroquinoline cyanoacetohydrazone) | | m/z 229.1081 |

TABLE 9-continued

Selected data for compounds synthesised according to Scheme 9

| Compound | Structure | NMR | Mass Spec [M + H]+ |
|---|---|---|---|
| 192 | 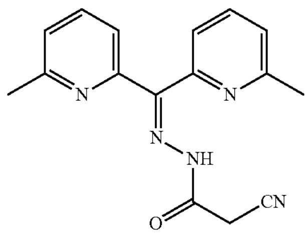 | | m/z 294.1439 |
| 193 | 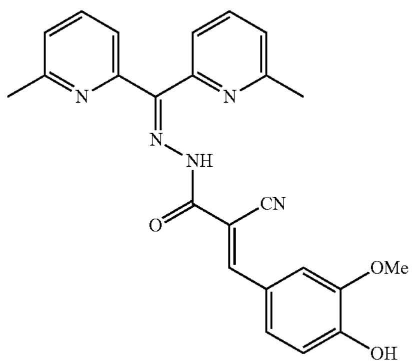 [SMILES: COc1cc(/C=C(\C#N)C(=O)NN=C(c2cccc(C)n2)c2cccc(C)n2)ccc1O] | ¹H NMR (600 MHz, d6-DMSO) δ 2.44 (s, 3H), 2.71 (s, 3H), 3.81 (s, 3H), 4.33 (s, 1H), 6.94 (d, J = 8.4 Hz, 1H), 7.19 (d, J = 7.2 Hz, 1H), 7.34 (d, J = 7.2 Hz, 1H), 7.44 (d, J = 7.2 Hz, 1H), 7.60-7.64 (m, 2H), 7.75 (s, 1H), 7.82-7.87 (m, 2H), 8.31 (s, 1H). | m/z 428.1271 |
| 194 | 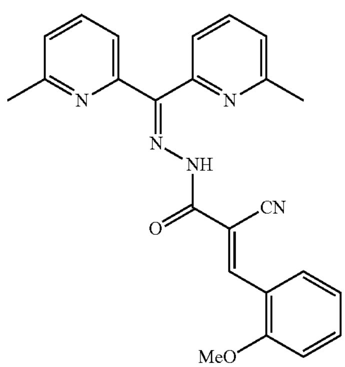 [SMILES: COc1ccccc1/C=C(\C#N)C(=O)NN=C(c1cccc(C)n1)c1cccc(C)n1] | ¹H NMR (600 MHz, d6-DMSO) δ 2.47 (s, 3H), 2.71 (s, 3H), 3.92 (s, 3H), 7.15 (t, J = 7.8 Hz, 1H), 7.23 (t, J = 4.2 Hz, 2H), 7.37 (d, J = 7.8 Hz, 1H), 7.47 (d, J = 7.8 Hz, 1H), 7.61-7.65 (m, 2H), 7.84-7.89 (m, 2H), 8.65 (s, 1H). | m/z 412.1774 |
| 195 | 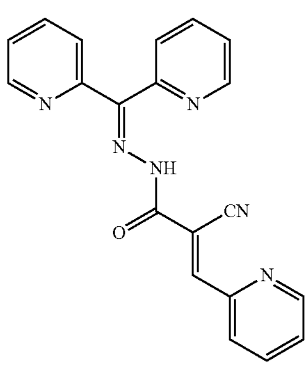 [SMILES: N#C/C(=C\c1ccccn1)C(=O)NN=C(c1ccccn1)c1ccccn1] | ¹H NMR (600 MHz, d6-DMSO) δ 7.51-7.57 (m, 2H), 7.57-7.60 (m, 1H), 7.63-7.66 (m, 1H), 7.92 (d, J = 7.8 Hz, 1H), 7.96 (d, J = 7.8 Hz, 1H), 7.99-8.05 (m, 3H), 8.47 (s, 1H), 8.65 (d, J = 4.8 Hz, 1H), 8.80 (t, J = 4.8 Hz, 2H). | m/z 355.1303 |

TABLE 9-continued

Selected data for compounds synthesised according to Scheme 9

| Compound | Structure | NMR | Mass Spec [M + H]+ |
|---|---|---|---|
| 196 | 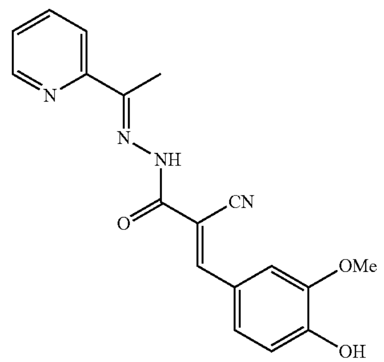 [SMILES: COc1cc(/C=C(\C#N)C(=O)N/N=C(\C)c2ccccn2)ccc1O] | ¹H NMR (600 MHz, d6-DMSO) δ 2.50 (s, 3H), 3.83 (s, 3H), 6.95 (d, J = 8.4 Hz, 1H), 7.59-7.63 (m, 2H), 7.77 (s, 1H), 7.85 (d, J = 8.4 Hz, 1H), 8.13 (t,J = 7.8 Hz, 1H), 8.29 (s, 1H), 8.71 (d, J = 3.6 Hz, 1H), 10.4 (br s, 1H). | m/z 337.1296 |

In a further example, substitution of the hydrazide group could be achieved by allowing an acyl hydrazone compound to react with a substituted alkyl halide in the presence of potassium carbonate to generate compounds U as described in Scheme 10 below. Heating 2-acetylpyridine with a substituted hydrazide afforded acyl hydrazone T. Alkylation of T by the action of a methyl bromoacetate and potassium carbonate in DMF generated ester U. In addition, compound U could be readily hydrolysed to a carboxylic acid derivative V by reaction with lithium hydroxide in a mixture of THF and water.

Scheme 10

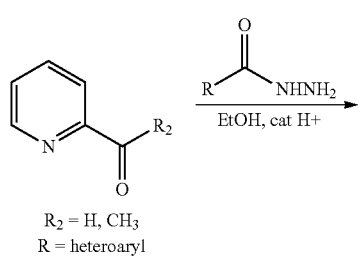

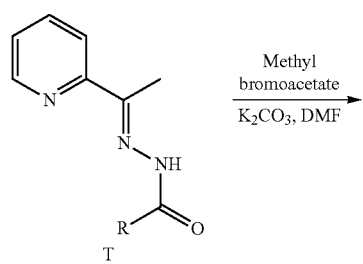

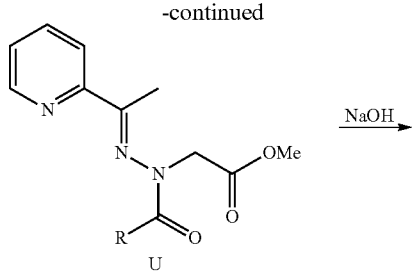

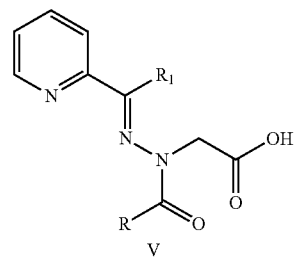

Example 10

(E)-N'-(1-(Pyridin-2-yl)ethylidene)benzo[b]thiophene-2-carbohydrazide (146)

To a mixture of 2-acetylpyridine (326 mg), benzothiophene-2-carboxylic acid hydrazide (518 mg) in EtOH (15 mL) at 60° C. was added 3 drops of conc. HCl. After heating for 30 min, the reaction was cooled overnight and a white solid precipitated out of solution to provide (E)-N'-(1-(pyridin-2-yl)ethylidene)benzo[b]thiophene-2-carbohydrazide (650 mg). MS m/z 296.0460[M+H]+.

TABLE 10

Hydrazone Intermediates synthesized according to Scheme 10

| Compound | Structure | Spectroscopic Data |
|---|---|---|
| 152 | | ¹H NMR (600 MHz, d6-DMSO) δ 2.45 (s, 3H), 2.97 (s, 3H), 7.47-7.50 (m, 1H), 7.98 (t, J = 7.8 Hz, 1H), 8.06 (d, 7=7.8 Hz, 1H), 8.65 (d, J = 3.6 Hz, 1H), 11.7 (s, 1H). MS mz 262.087 [M + H]⁺. |
| 153 | | ¹H NMR (600 MHz, d6-DMSO) δ 2.97 (s, 3H), 7.69 (dd, J = 6.6, 4.8 Hz, 1H), 8.01 (s, 1H), 8.11 (d, J = 8.4 Hz, 1H), 8.25 (s, 1H), 8.66 (d, J = 4.2 Hz, 1H), 12.59 (s, 1H) |

(E)-Methyl 2-(1-(benzo[b]thiophene-2-carbonyl)-2-(1-(pyridin-2-yl) ethylidene) hydrazinyl) Acetate 147

To a solution of (E)-N'-(1-(pyridin-2-yl)ethylidene)benzo[b]thiophene-2-carbohydrazide (190 mg) in DMF (8 mL) was added methyl bromoacetate (200 μL) and K₂CO₃ (210 mg). The reaction was heated to 50° C. for 1.5 h during which time a white precipitate formed. The reaction was cooled, and H₂O (8 mL) was added slowly. After allowing to stand for 30 min, (E)-methyl 2-(1-(benzo[b]thiophene-2-carbonyl)-2-(1-(pyridin-2-yl) ethylidene)hydrazinyl)acetate precipitated out of solution as a yellow solid (90 mg) 147. ¹H NMR (d6-DMSO) δ 2.44 (s, 3H), 3.73 (s, 3H), 5.06 (s, 2H), 7.44-7.49 (m, 2H), 7.53 (d, J=7.2 Hz, 1H), 8.00-8.06 (m, 3H), 8.21 (s, 1H), 8.41 (d, J=7.8 Hz, 1H), 8.69 (d, J=3.6 Hz, 1H). MS m/z 368.1061 [M+H]⁺.

(E)-2-(1-(Benzo[b]thiophene-2-carbonyl)-2-(1-(pyridin-2-yl)ethylidene)hydrazinyl) acetic acid 148

To a solution of (E)-methyl 2-(1-(benzo[b]thiophene-2-carbonyl)-2-(1-(pyridin-2-yl) ethylidene)hydrazinyl) acetate (64 mg) in THF (7 mL) was added LiOH (65 mg) and H₂O (3 mL). The reaction was heated to 50° C. for 2 h and then cooled to rt. THF was removed in vacuo and a yellow precipitate formed. The product was collected by filtration to afford (E)-2-(1-(benzo[b]thiophene-2-carbonyl)-2-(1-(pyridin-2-yl)ethylidene) hydrazinyl)acetic acid as a yellow powder. MS m/z 354.09 [M+H]⁺.

TABLE 11

Target compounds prepared according to Scheme 10.

| Compound | Structure | Spectroscopic Data |
|---|---|---|
| 149 | | ¹H NMR (600 MHz, d6-DMSO) δ 2.50 (s, 3H), 2.99 (s, 3H), 3.74 (s, 3H), 5.14 (s, 2H), 7.55 (dd, J = 7.2, 4.8 Hz, 1H), 8.04 (t, J = 7.8 Hz, 1H), 8.24 (d, J = 7.8 Hz, 1H), 8.71 (d, J = 4.8 Hz, 1H). MS m/z 334.0996 [M + H]⁺. |
| 150 | | ¹H NMR (600 MHz, d6-DMSO) δ 2.98 (s, 3H), 3.77 (s, 3H), 5.15 (s, 2H), 7.48-7.52 (m, 1H), 8.01-8.09 (m, 2H), 8.20 (s, 1H), 8.74-8.78 (m, 1H). MS m/z 320.0822 [M + H]⁺. |

TABLE 11-continued

Target compounds prepared according to Scheme 10.

| Compound | Structure | Spectroscopic Data |
|---|---|---|
| 151 | 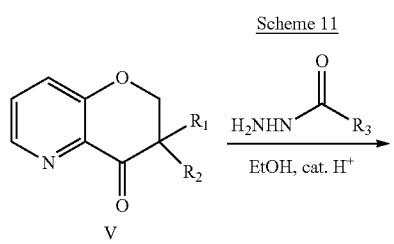 | H NMR (600 MHz, d6-DMSO) δ 2.51 (s, 3H), 2.98 (s, 3H), 5.05 (s, 2H), 7.54-7.57 (m, 1H), 8.05 (t, J = 7.2 Hz, 1H), 8.25 (d, J = 7.8 Hz, 1H), 8.71 (d,J = 3.6 Hz, 1H). MS m/z 320.08 [M + H]$^+$. |

In a further example, a number fused pyridopyrano acyl hydrazones were synthesised according to Scheme 11. ketone V was heated together with substituted aryl benzhydrazides in the presence of catalytic acid to afford target acyl hydrazones W.

Scheme 11

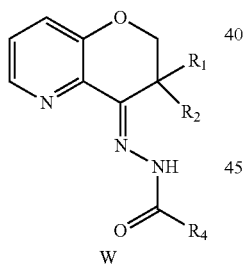

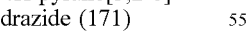

Example 11 (E)-N'-(2,3-dihydro-4H-pyrano[3,2-b]pyridin-4-ylidene)nicotinohydrazide (171)

To a mixture of 2H-pyran[3,2-b]pyridine-4(3H)-one V (49 mg, 0.33 mmol) in EtOH (6 mL) was added nicotinic acid hydrazide (44 mg, 0.32 mmol) followed by one drop of conc. HCl. The reaction was heated to 55° C. for 30 min, then cooled to room temp to afford (E)-N'-(2,3-dihydro-4H-pyrano[3,2-b]pyridin-4-ylidene)nicotinohydrazide 171 as an off-white solid. (34 mg). $^1$H NMR (500 MHz, d6-DMSO) δ 2.96 (t, J=6.0 Hz, 2H), 4.47 (t, J=6.0 Hz, 2H), 7.56-7.64 (m, 2H), 7.77 (t, J=5.0 Hz, 1H), 8.41 (d, J=7.5 Hz, 1H), 8.50 (d, J=5 Hz, 1H), 8.88 (d, J=5.0 Hz, 1H), 9.13 (s, 1H), 15.63 (s, 1H). MS: m/z 269.1033 [M+H]+.

TABLE 12

Compounds synthesized according to Scheme 11

| Compound | Structure | Mass Spectrometry [M + H]$^+$ |
|---|---|---|
| 172 | 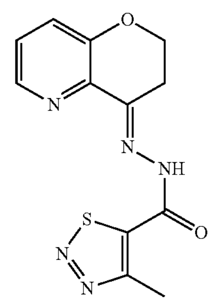 [SMILES: Cc1nnsc1C(=O)N/N=C1\CCOc2cccnc21] | m/z 290.0708 |
| 173 | 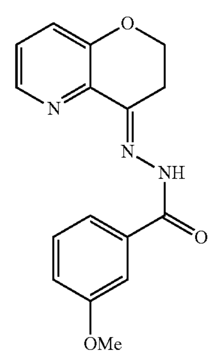 [SMILES: COc1cccc(C(=O)N/N=C2\CCOc3cccnc32)c1] | m/z 298.1189 |
| 174 | 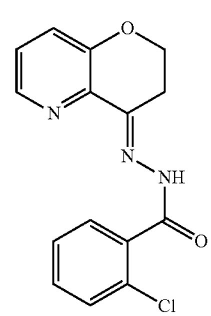 [SMILES: O=C(N/N=C1\CCOc2cccnc21)c1ccccc1Cl] | m/z 302.0692 |

TABLE 12-continued

Compounds synthesized according to Scheme 11

| Compound | Structure | Mass Spectrometry [M + H]+ |
|---|---|---|
| 175 | 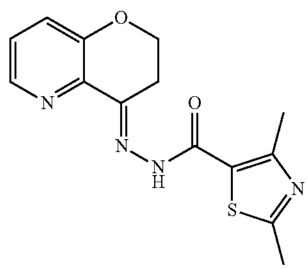 [SMILES: Cc1nc(C)c(C(=O)N/N=C2\CCOc3cccnc32)s1] | m/z 303.0911 |
| 176 | 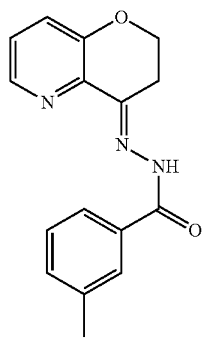 [SMILES: Cc1cccc(C(=O)N/N=C2\CCOc3cccnc32)c1] | m/z 282.1236 |
| 177 | 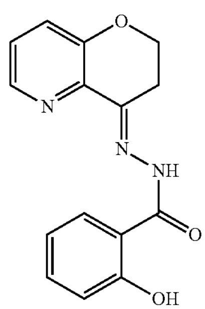 [SMILES: O=C(N/N=C1\CCOc2cccnc21)c1ccccc1O] | m/z 284.1027 |
| 178 | 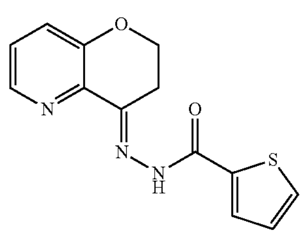 [SMILES: O=C(N/N=C1\CCOc2cccnc21)c1cccs1] | m/z 274.0646 |

BIOLOGICAL EXAMPLES

GSK 3b Assay

The phosphorylation of GSK-3β is enhanced when Zn is imported into a cell by a Zn ionophore. This property was measured for the compounds of the current invention and the data presented relative to the know Zn ionophore PBT2 using the following protocol.

The human neuroblastoma SH-SY5Y cells were obtained from Cell bank Australia (Catalogue number: 94030304). SH-SY5Y cell culture was maintained in DMEM/F12+15% FBS inside an incubator at 37° C. in the presence of 5% $CO_2$. The cells were sub-cultured once a week and the media exchanged once during the week. Cells for the assay were plated at a density of 60,000 cells/well.

Stock solutions of the samples were prepared as a 5 mM stock in DMSO and a stock solution of 1 mM $ZnCl_2$/3 mM Glutamic acid was prepared in water. Immediately before use the compounds were diluted 1:10 with water before being added to Locke's buffer in a treatment tube. Samples were subsequently treated with either distilled water or the $ZnCl_2$/Glutamic acid solution to yield a treatment solution which has a final concentration of the test compound at 2 µM+/−$ZnCl_2$ at 5 µM.

The culture media was aspirated from the wells and the media replaced with the treatment solution prepared above. In addition to the relative standard (PBT2+/−$ZnCl_2$), control wells were also included consisting of +/−$ZnCl_2$ at 5 µM with all treatments done in triplicate. The plate was incubated at 37° C. with the treatment solution for 2 h after which time the wells were aspirated and washed with sterile PBS.

Measurement of the change of phospho-GSK-3β was determined using an AlphaScreen® SureFire® Phospho-GSK 30β (Ser9) Kit with the cells being processed as per the manufacturer's instructions using an initial incubation of 2 h/24° C. and a final incubation of 16 h/24° C.

The fluorescence was measured on an Enspire plate reader. In the absence of the metal, the compounds had no effect on the signal whereas, in the presence of the metal, positive compounds showed an increased signal which is presented as a % of the positive standard PBT2+$ZnCl_2$ set as 10000. Representative data is presented in Table 12 using the following ranges: A<50%, B 50-<100%, C 100-<150%, D>150%.

TABLE 12

GSK Data for Selected Compounds

| Compound | GSK-Zn | Compound | GSK-Zn | Compound | GSK-Zn |
|---|---|---|---|---|---|
| 1 | A | 43 | C | 92 | C |
| 2 | A | 44 | B | 94 | C |
| 3 | A | 45 | C | 95 | C |
| 4 | A | 46 | C | 100 | C |
| 6 | A | 47 | C | 103 | B |
| 7 | A | 48 | C | 104 | D |
| 8 | A | 49 | B | 105 | B |
| 9 | A | 50 | C | 106 | A |
| 10 | B | 51 | B | 109 | B |
| 11 | C | 52 | B | 115 | A |
| 12 | B | 64 | B | 119 | A |
| 15 | D | 65 | B | 121 | A |
| 16 | A | 67 | C | 122 | A |
| 17 | A | 72 | C | 123 | C |
| 18 | B | 73 | C | 126 | C |
| 20 | A | 74 | B | 128 | D |
| 21 | A | 75 | C | 129 | C |
| 23 | C | 76 | C | 130 | A |
| 24 | A | 77 | C | 131 | B |
| 25 | B | 78 | C | 132 | C |
| 26 | A | 81 | C | 133 | C |
| 38 | A | 82 | C | 134 | B |
| 39 | A | 87 | C | 135 | B |
| 41 | A | 91 | C | 146 | C |

Method I: Measurement of Fe Efflux from Cells

Compounds of the current invention were assessed for their ability to efflux iron (Fe) from a cell using the following protocol.

The human neuroblastoma line BE(2)-M17 (M17) cell cultures were acquired from Sigma Aldrich (Catalogue #: 95011816). M17 Cells were maintained in Opti-MEM reduced serum media supplemented with 10% fetal bovine serum (Bovogen, SFBSF) and passaged twice weekly. Cells were cultured at 37° C. in the presence of 5% $CO_2$. Culture supplies were sourced from Thermo Fisher unless otherwise stated.

A solution of $^{57}Fe$ cold isotope was prepared by dissolving $^{57}Fe$ metal (>95% enrichment, Trace Sciences International) in concentrated HCl to give a final concentration of 573 mM. From this master solution, a 10 mM working solution was prepared in sterile water. The working solution was used within two months of preparation.

M17 cells were loaded with iron initially by seeding into 48-well plates at a density of $0.15 \times 10^6$ cells per well in 0.5 mL media. After 48 h, old media was discarded. Fresh media was supplemented with 20 µM $^{57}Fe$ isotope, from the 10 mM $^{57}Fe$ working solution. Cells received 0.2 mL of this $^{57}Fe$ enriched media and were returned to the incubator for 20 h. The ability of experimental compounds to efflux iron was determined by the dissolution of compounds in DMSO and diluted in Hanks' Balanced Salt Solution (HBSS) for treatment of M17 cells. After $^{57}Fe$ incubation, cells were rinsed twice with HBSS and treated with 0.15 mL trial compound for 2 h at a concentration of 20 µM. All assays included a relevant vehicle (0.4%-0.8% DMSO) as well as a positive control (20 µM). Following the treatment period, 0.1 mL of media was collected from cells and the extracellular $^{57}Fe$ content was analysed via inductively coupled mass spectrometry (ICP-MS, Agilent 7700x series instrument).

To perform this protocol the following supplies were purchased from Sigma Aldrich: anhydrous dimethyl sulfoxide (DMSO, Catalogue #: 276855), Hanks' Balanced Salt Solution supplemented with 20 mM HEPES and 4.2 mM Sodium Bicarbonate (HBSS, pH: 7.4, Catalogue #: H1387).

The ability of the compounds of the invention to efflux Fe from a cell was determined using the above protocol hence cells having been pre-treated with Fe in the media for 24 h were subsequently washed and treated with fresh, Fe free media either with or without the compound (20 µM). After 2 h the Fe levels in the media were measured and the increase determined as a percentage increase relative to the cell media in the absence of the compound.

$$\% \text{ Fe efflux} = \frac{([\text{Fe in media}]_{Compound} - [\text{Fe in media}]_{No\ Compound})}{[\text{Fe in media}]_{No\ Compound}} \times 100$$

Representative data is provided in Table 13 where the % Fe efflux for the specified compounds of the invention lie in the following ranges: A<30%, B 30-100%, C 100-150%; D>150%.

TABLE 13

Fe efflux data for Selected Compounds

| Compound | Fe-Efflux | Compound | Fe-Efflux | Compound | Fe-Efflux |
|---|---|---|---|---|---|
| 1 | D | 31 | B | 55 | B |
| 2 | C | 32 | C | 56 | B |
| 3 | D | 33 | D | 57 | C |
| 4 | B | 39 | D | 58 | A |
| 6 | A | 40 | D | 61 | B |
| 7 | B | 42 | D | 91 | B |
| 8 | C | 47 | B | 101 | A |
| 9 | B | 48 | D | 117 | A |
| 10 | B | 49 | D | 122 | A |
| 15 | D | 50 | A | 138 | A |

TABLE 13-continued

Fe efflux data for Selected Compounds

| Compound | Fe-Efflux | Compound | Fe-Efflux | Compound | Fe-Efflux |
|---|---|---|---|---|---|
| 23 | D | 52 | B | 147 | A |
| 171 | A | 172 | C | 178 | C |

The invention claimed is:

1. A compound of formula (Ib):

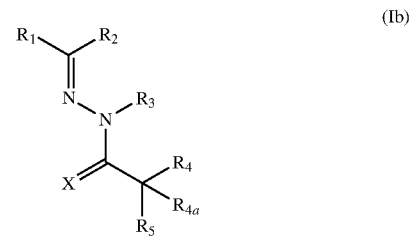

(Ib)

wherein X is O;

$R_1$ is selected from:

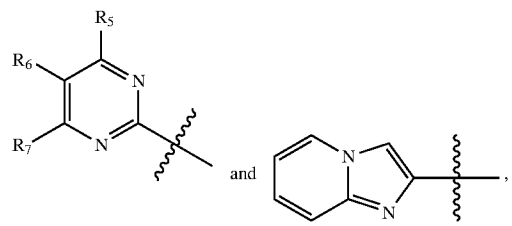

and $R_6$ and $R_7$ are independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, CN, $CO_2R_9$ and $N(R_9)_2$; or $R_6$ and $R_7$ taken together with the atoms to which they are attached form an unsubstituted 6 membered aryl or heteroaryl ring;

each $R_8$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, halo, $(CH_2)_mCO_2R_9$ and $(CH_2)_mN(R_9)_2$;

each $R_9$ is independently selected from $C_{1-6}$alkyl, $C_{2-6}$alkenyl, $C_{2-6}$alkynyl and $C_{1-6}$haloalkyl;

$R_2$ is selected from hydrogen, $C_{1-6}$alkyl, $C_{2-6}$alkenyl, $C_{2-6}$alkynyl, $C_{1-6}$haloalkyl, $C_{3-8}$ cycloalkyl and

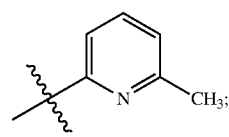 [SMILES: *c1cccc(C)n1]

or $R_1$ and $R_2$ taken together form

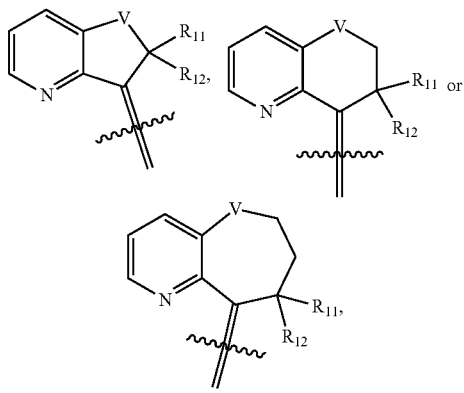

wherein V is $CH_2$, O or S and $R_{11}$ and $R_{12}$ are each independently selected from hydrogen, $C_{1-6}$alkyl, $C_{2-6}$alkenyl, $C_{2-6}$alkynyl, halo, $C_{1-6}$haloalkyl, $(CH_2)_mC_{3-8}$cycloalkyl, $(CH_2)_m$aryl, $(CH_2)_m$heterocyclyl, $(CH_2)_m$heteroaryl and $COR_{13}$ where $R_{13}$ is selected from OH, $OC_{1-6}$alkyl, $OC_{2-6}$alkenyl, $OC_{2-6}$alkynyl and $N(R_9)_2$, wherein the cycloalkyl, heterocycloalkyl or heteroaryl ring of the bicyclic structure formed by $R_1$ and $R_2$ may be optionally substituted by one or more first substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O) $C_{1-6}$alkyl, —$NH_2$, —$NH(C_{1-6}$alkyl), —$N(C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl, or $R_1$ and $R_2$ are both:

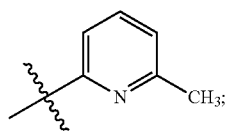 [SMILES: *c1cccc(C)n1]

$R_3$ is selected from hydrogen, $C_{1-6}$alkyl, $C_{2-6}$alkenyl, $C_{2-6}$alkynyl and $C(R_{10})_2)_mCO_2R_9$;

$R_4$ and $R_{4a}$ are each independently selected from hydrogen, $C_{1-6}$alkyl, $C_{2-6}$alkenyl, $C_{2-6}$alkynyl and $C_{1-6}$haloalkyl; and $R_5$ is hydrogen, $(C(R_{10})_2)_m$aryl, $(C(R_{10})_2)_m$heteroaryl or $O(C(R_{10})_2)_m$heteroaryl wherein the aryl and heteroaryl are optionally substituted by one or more second substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O) $C_{1-6}$alkyl, —$NH_2$, —$NH(C_{1-6}$alkyl), —$N(C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl; or $R_{4a}$ is CN and $R_4$ and $R_5$ are both hydrogen or taken together form:

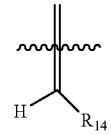

where $R_{14}$ is hydrogen, $(C(R_{10})_2)_m$aryl or $(C(R_{10})_2)_m$heteroaryl wherein the aryl and heteroaryl are optionally substituted by one or more third substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O) $C_{1-6}$alkyl, —$NH_2$, —$NH(C_{1-6}$alkyl), —$N(C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl; or $R_{4a}$ is absent and $R_4$ and $R_5$ taken together form an aryl or heteroaryl group, said aryl or heteroaryl being monocyclic or bicyclic, and wherein the aryl or heteroaryl is optionally substituted by one or more fourth substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O) $C_{1-6}$alkyl, —$NH_2$, —$NH(C_{1-6}$alkyl), —$N(C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl;

each $R_{10}$ is independently selected from hydrogen, $C_{1-6}$alkyl, $C_{2-6}$alkenyl, $C_{2-6}$alkynyl, hydroxy, $C_{1-6}$alkoxy, $C_{1-6}$haloalkyl, $C_{1-6}$haloalkoxy, CN, halo and $N(R_9)_2$;

m is 0 or an integer of 1 to 6;

or a pharmaceutically acceptable salt thereof.

2. The compound according to claim 1 wherein one or both of the following applies:

i) $R_1$ is selected from the group consisting of:

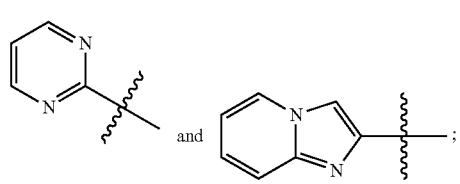 [SMILES: *c1ncccn1 ; *c1cn2ccccc2n1]

or a pharmaceutically acceptable salt thereof; and ii) $R_2$ is selected from hydrogen, $C_{1-6}$alkyl, $C_{2-6}$alkenyl, $C_{2-6}$alkynyl, $C_{3-8}$cycloalkyl.

3. The compound according to claim 1 wherein one of the following applies:

i) $R_1$ and $R_2$ are both

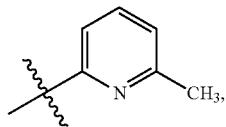 [SMILES: *c1cccc(C)n1]

or a pharmaceutically acceptable salt thereof; or ii) $R_1$ and $R_2$ together are selected from:

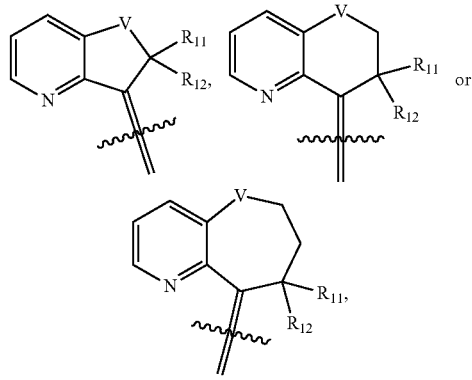

wherein V is $CH_2$ or O and $R_{11}$ and $R_{12}$ are each independently selected from hydrogen, $C_{1-6}$alkyl, $C_{2-6}$alkenyl, $C_{2-6}$alkynyl, $C_{1-6}$haloalkyl, halo, $(CH_2)_m C_{3-8}$cycloalkyl, $(CH_2)_m$aryl, $(CH_2)_m$heterocyclyl, $(CH_2)_m$heteroaryl and $COR_{13}$ where $R_{13}$ is selected from OH, $OC_{1-6}$alkyl, $OC_{2-6}$alkenyl, $OC_{2-6}$alkynyl and $N(R_9)_2$, or a pharmaceutically acceptable salt thereof.

4. The compound according to claim 1 wherein $R_3$ is selected from hydrogen, $C_{1-6}$alkyl, $CH_2CO_2H$ and $CH_2CO_2CH_3$ or a pharmaceutically acceptable salt thereof.

5. The compound according to claim 1 wherein $R_4$ and $R_{4a}$ are each independently selected from hydrogen, $C_{1-3}$alkyl, $C_{2-3}$alkenyl, $C_{2-3}$alkynyl and $C_{1-3}$haloalkyl; and $R_5$ is hydrogen, $(CH_2)_m$aryl or $(CH_2)_m$heteroaryl wherein the aryl and heteroaryl are optionally substituted by the one or more second substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O)$C_{1-6}$alkyl, —$NH_2$, —NH($C_{1-6}$alkyl), —N($C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl, or a pharmaceutically acceptable salt thereof.

6. The compound according to claim 1 wherein $R_{4a}$ is absent and $R_4$ and $R_5$ taken together form an aryl or heteroaryl group, said aryl or heteroaryl being monocyclic or bicyclic, and wherein the aryl or heteroaryl is optionally substituted by the one or more fourth substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O) $C_{1-6}$alkyl, —$NH_2$, —NH($C_{1-6}$alkyl), —N($C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl, or a pharmaceutically acceptable salt thereof.

7. The compound according to claim 6 wherein $R_4$ and $R_5$ taken together form a phenyl ring, a 2-pyridinyl ring, 3-pyridinyl ring, 4-pyridinyl ring, 3-pyridazinyl ring, 4-pyridazinyl ring, 2-furanyl, 3-furanyl, 2-thiophenyl ring, 3-thiophenyl ring, 2-thiazolyl ring, 3-thiazolyl ring, 4-thiazolyl ring, 3-isoxazolyl ring, 4-isoxazolyl ring, 5-isoxazolyl ring, 4-(1,2,3-thiadiazolyl) ring, 5-(1,2,3-thiadiazolyl) ring, 4-thiadiazolyl ring, 5-thiadiazolyl ring, 2-benzo[b]thiophenyl, 3-benzothiophenyl ring, 3-(1H)-indolyl ring or a 4H-thieno[3,2-c]chromene ring, or a pharmaceutically acceptable salt thereof.

8. The compound according to claim 1 wherein one of the following applies:

i) $R_{4a}$ is CN and $R_4$ and $R_5$ taken together form:

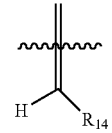

where $R_{14}$ is hydrogen, $(C(R_{10})_2)_m$aryl or $(C(R_{10})_2)_m$heteroaryl wherein the aryl and heteroaryl are optionally substituted by the one or more third substituents selected from the group consisting of $C_{1-6}$alkyl, $C_{2-6}$alkenyl, oxo (=O), —OH, $C_{1-6}$alkylO—, $C_{2-6}$alkenylO—, —$CO_2H$, —$CO_2C_{1-6}$alkyl, —OC(=O) $C_{1-6}$alkyl, —$NH_2$, —NH($C_{1-6}$alkyl), —N($C_{1-6}$alkyl)$_2$, —$C_{1-6}$alkyl$NH_2$, —$C_{1-6}$alkylNH($C_{1-6}$alkyl), —$C_{1-6}$alkylN($C_{1-6}$alkyl)$_2$, —$OC_{1-6}$alkyl$NH_2$, —$OC_{1-6}$alkylNH ($C_{1-6}$alkyl), —$OC_{1-6}$alkylN($C_{1-6}$alkyl)$_2$, —CN, -halogen, —$CF_3$, —$OCF_3$, —$CHF_2$, —$OCHF_2$, heterocyclyl, heteroaryl, —$OC_{1-6}$alkylheterocyclyl, and —C(=O)$C_{1-6}$alkyl, or a pharmaceutically acceptable salt thereof; or ii) $R_{4a}$ is CN and $R_4$ and $R_5$ are both hydrogen.

9. A compound according to claim 1 which is a compound of formula (II):

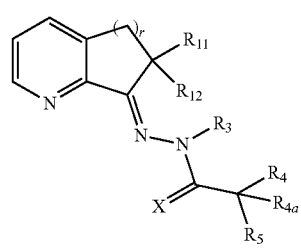

(II)

wherein X, $R_3$, $R_4$, $R_{4a}$ and $R_5$ are as defined in claim 1, $R_{11}$ and $R_{12}$ are each independently selected from hydrogen, $C_{1-6}$alkyl, $C_{2-6}$alkenyl, $C_{2-6}$alkynyl, $C_{1-6}$haloalkyl, halo, $(CH_2)_m C_{3-8}$cycloalkyl, $(CH_2)_m$aryl, $(CH_2)_m$heterocyclyl, $(CH_2)_m$heteroaryl and $COR_{13}$ where $R_{13}$ is selected from OH, $OC_{1-6}$alkyl, $OC_{2-6}$alkenyl, $OC_{2-6}$alkynyl and $N(R_9)_2$ and r is 1, 2 or 3, or a pharmaceutically acceptable salt thereof.

10. A compound according to claim 9 which is a compound of formula (IIa):

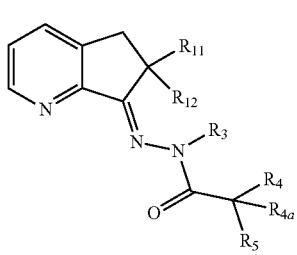

(IIa)

wherein $R_3$, $R_4$, $R_{4a}$, $R_5$, $R_{11}$ and $R_{12}$ are as defined for formula(II), or a pharmaceutically acceptable salt thereof.

11. A compound according to claim 9 which is a compound of formula (IIb):

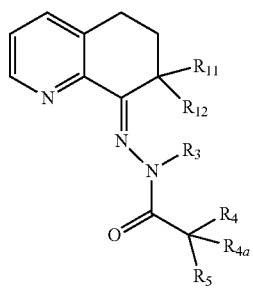

(IIb)

wherein $R_3$, $R_4$, $R_{4a}$, $R_5$, $R_{11}$ and $R_{12}$ are as defined for formula(II), or a pharmaceutically acceptable salt thereof.

12. A compound according to claim 9 which is a compound of formula (IIc):

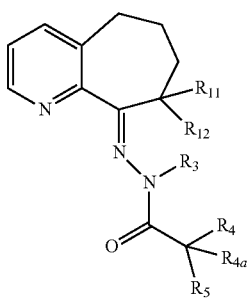

wherein $R_3$, $R_4$, $R_{4a}$, $R_5$, $R_{11}$ and $R_{12}$ are as defined for formula(II), or a pharmaceutically acceptable salt thereof.

13. A compound according to claim 1 which is a compound of formula (IIIa):

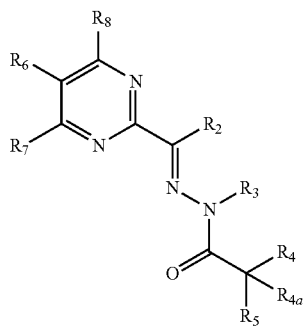

(IIIa)

wherein $R_2$, $R_3$, $R_4$, $R_{4a}$, $R_5$, $R_6$, $R_7$ and $R_8$ are as defined in claim 1, or a pharmaceutically acceptable salt thereof.

14. The compound according to claim 1 which is a compound of formula (IIId):

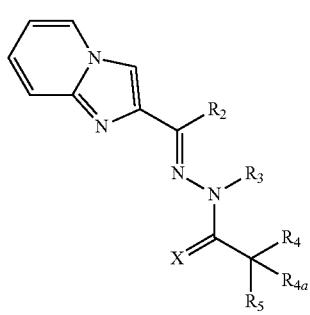

(IIId)

wherein $R_3$, $R_4$, $R_{4a}$ and $R_5$ are as defined in claim 1, or a pharmaceutically acceptable salt thereof.

15. A compound according to claim 1 which is a compound of formula (V):

(V)

wherein X, $R_2$, $R_3$, $R_4$, $R_{4a}$ and $R_5$ are as defined in claim 1, or a pharmaceutically acceptable salt thereof.

16. A compound according to claim 1, which is a compound of formula (VI):

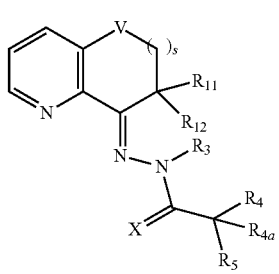

(VI)

wherein X, V, $R_3$, $R_4$, $R_{4a}$ and $R_5$ are as defined for formula (Ib), $R_{11}$ and $R_{12}$ are each independently selected from hydrogen, $C_{1-6}$alkyl, $C_{2-6}$alkenyl, $C_{2-6}$alkynyl, halo, $C_{1-6}$haloalkyl, $(CH_2)_mC_{3-6}$ cycloalkyl, $(CH_2)_m$aryl, $(CH_2)_m$heterocyclyl, $(CH_2)_m$heteroaryl and $COR_{13}$ where $R_{13}$ is selected from OH, $OC_{1-6}$alkyl, $OC_{2-6}$alkenyl, $OC_{2-6}$alkynyl and $N(R_9)_2$ and s is 0, 1 or 2, or a pharmaceutically acceptable salt thereof.

17. A compound according to claim 16, which is a compound of formula (VIb):

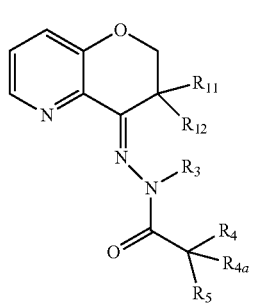

(VIb)

wherein $R_3$, $R_4$, $R_{4a}$, $R_5$, $R_{11}$ and $R_{12}$ are as defined for formula(VI), or a pharmaceutically acceptable salt thereof.

18. A compound according to claim 1, which is any one of the following compounds:

(E)-N'-(6,7-Dihydroquinolin-8(5H)-ylidene)nicotinohydrazide;
(E)-N'-(5H-Cyclopenta[b]pyridin-7(6H)-ylidene)-3,4-dimethoxybenzohydrazide;
(E)-N'-(6,7-Dihydroquinolin-8(5H)-ylidene)-2-(2-(pyrrolidin-1-yl)ethoxy) benzohydrazide hydrochloride;
(E)-4-Methyl-N'-(1-(pyrimidin-2-yl)propylidene)-1,2,3-thiadiazole-5-carbohydrazide;
(Z)—N'-(Imidazo[1,2-a]pyridin-2-ylmethylene)-3-methoxybenzohydrazide;
(2E,N'E)-2-Cyano-N'-(6,7-dihydroquinolin-8(5H)-ylidene)-3-(2-hydroxyphenyl) acrylohydrazide;
(E)-N'-(2,3-dihydro-4H-pyrano[3,2-b]pyridin-4-ylidene) nicotinohydrazide;
N'-(bis(6-Methylpyridin-2-yl)methylene)-4-hydroxy-3-methoxybenzohydrazide;
5-chloro-N'-(di(pyridin-2-yl)methylene)-3-((dimethylamino)methyl)-2-hydroxybenzohydrazide;

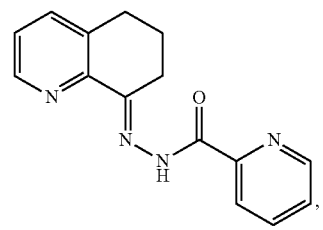
,

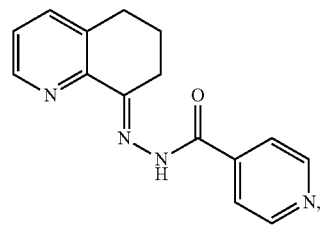
,

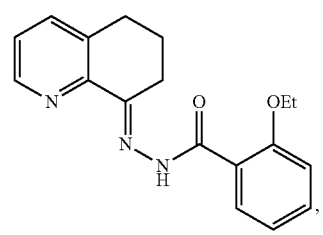
,

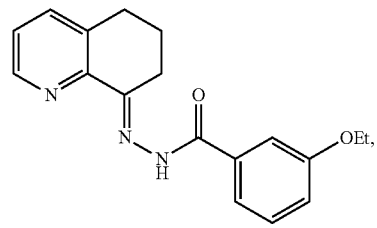
,

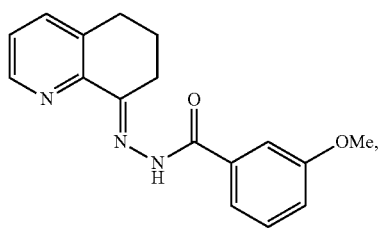
,

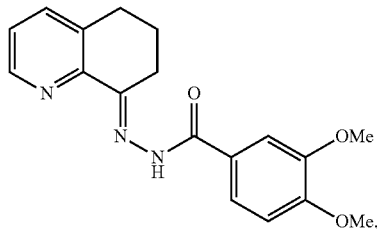
,

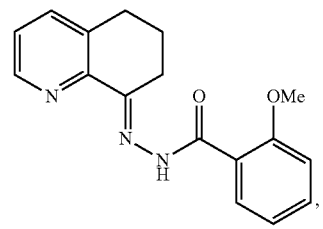
,

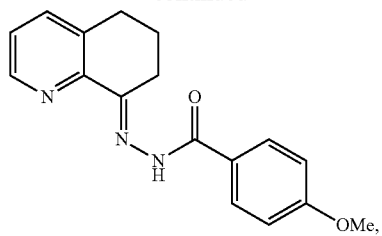
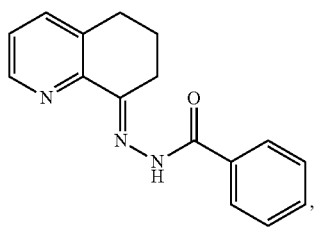
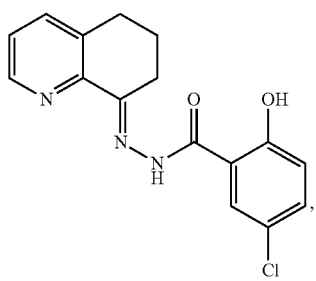
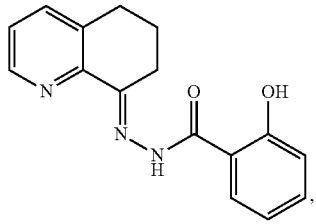
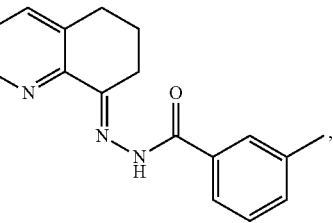
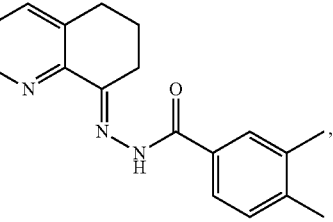
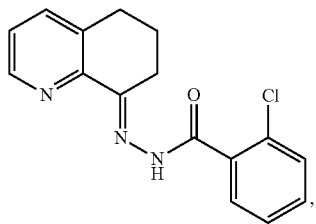
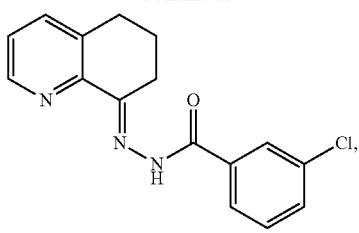
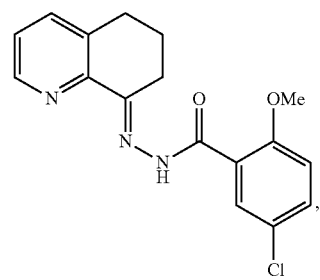
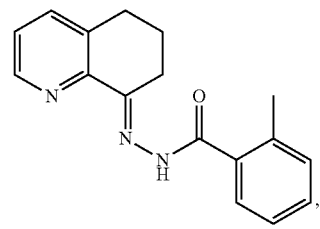
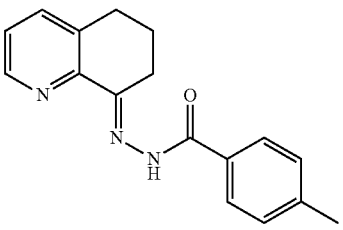
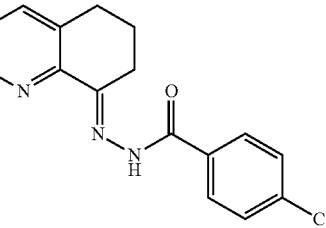
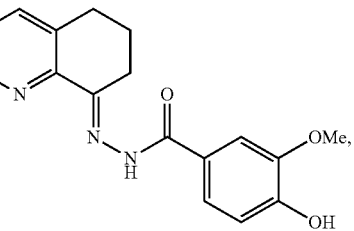
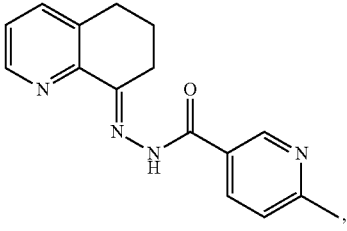

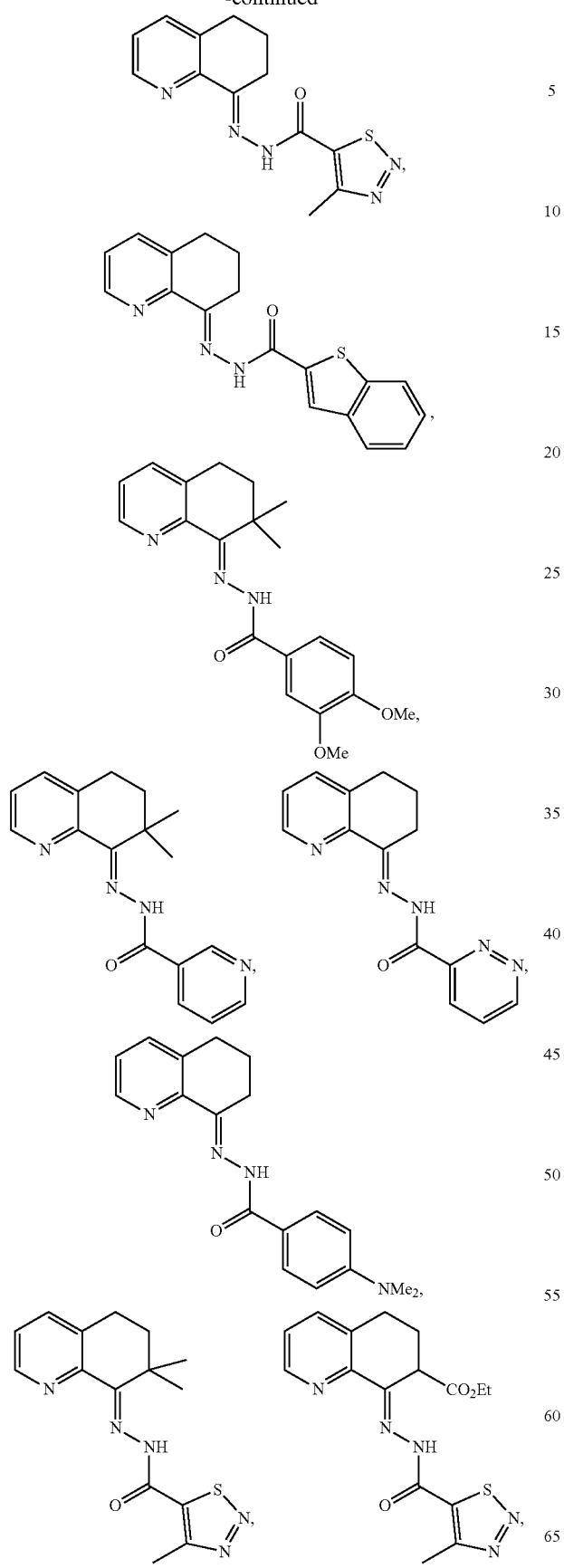
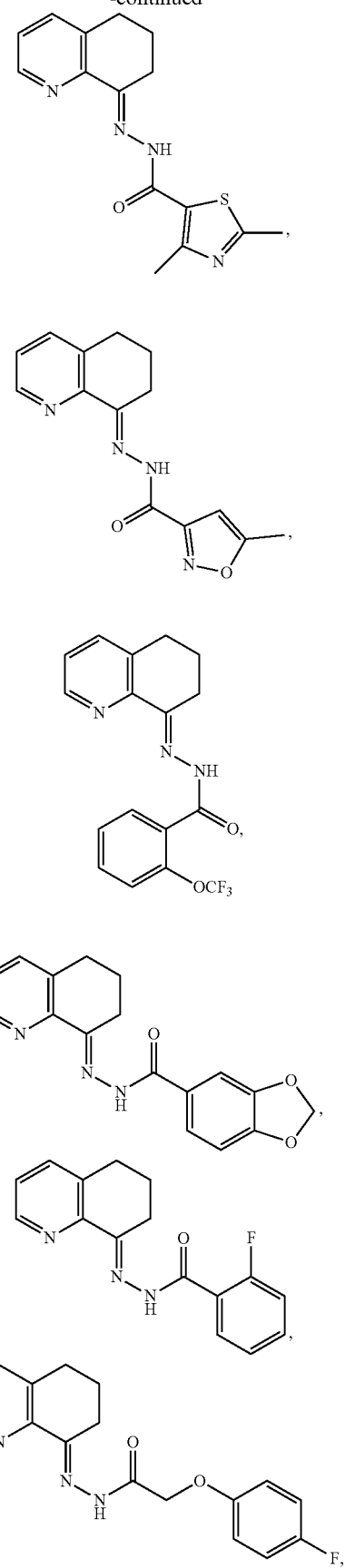

127
-continued
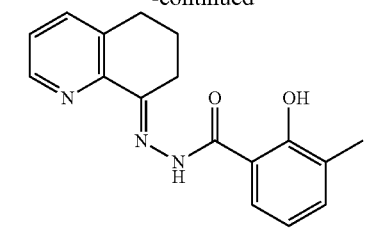
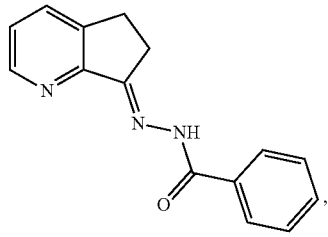
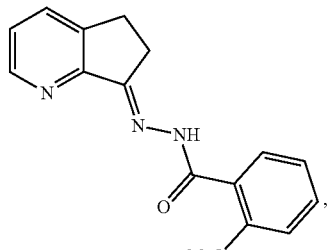
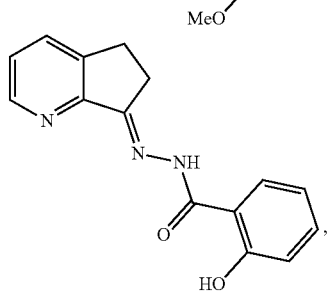
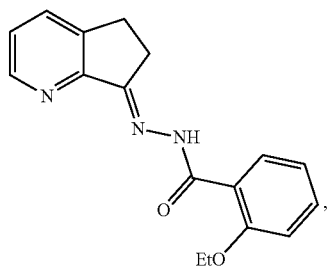
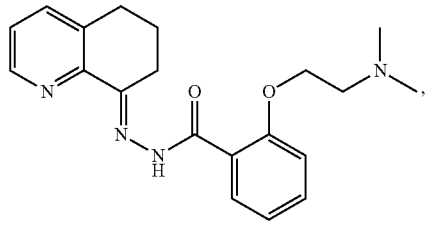
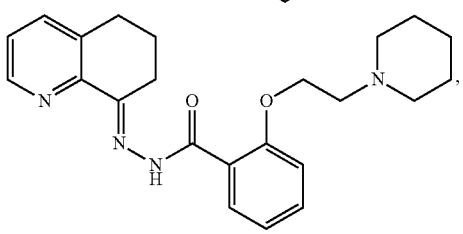
128
-continued
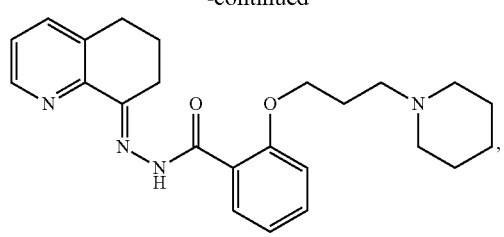
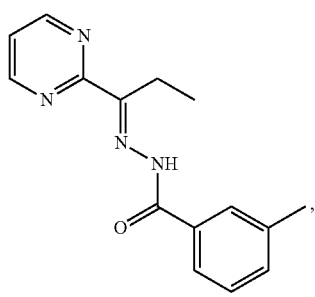
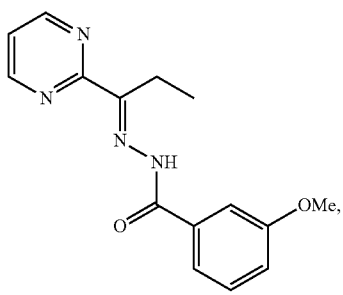
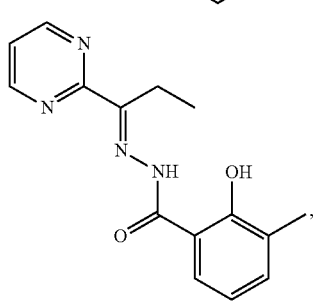
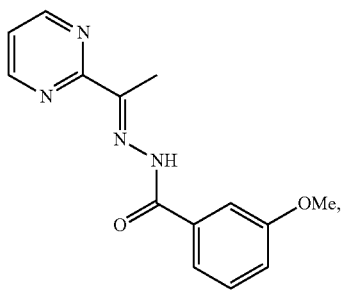
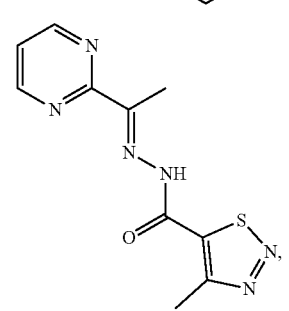

129
-continued
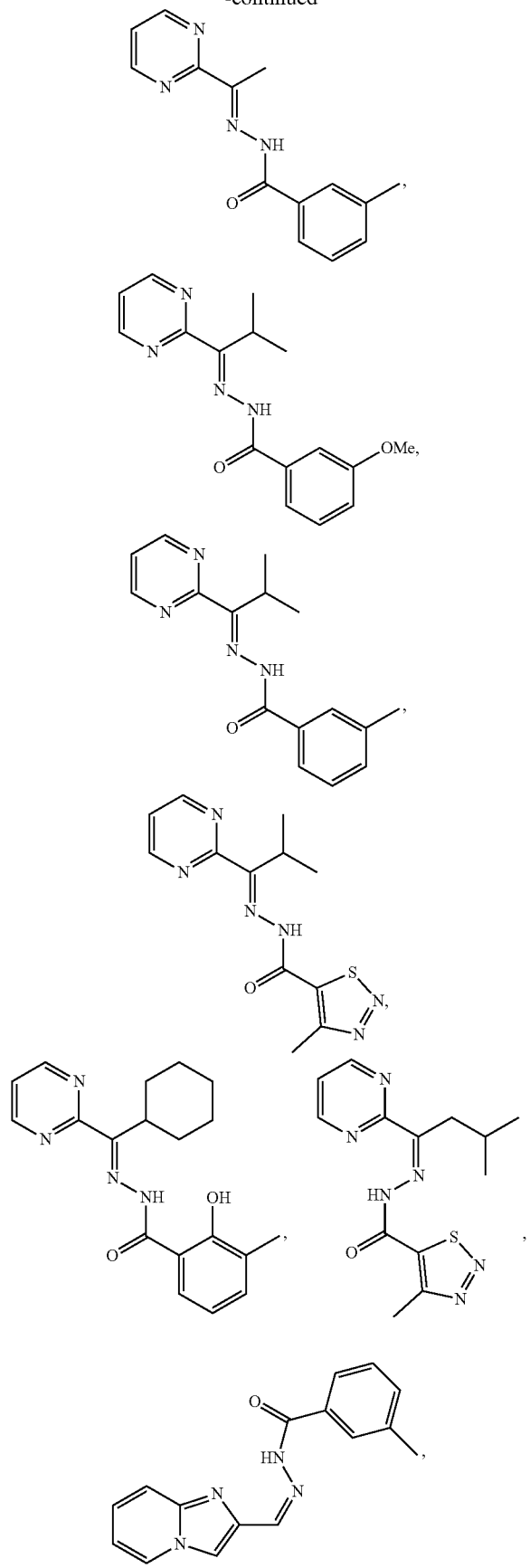
130
-continued
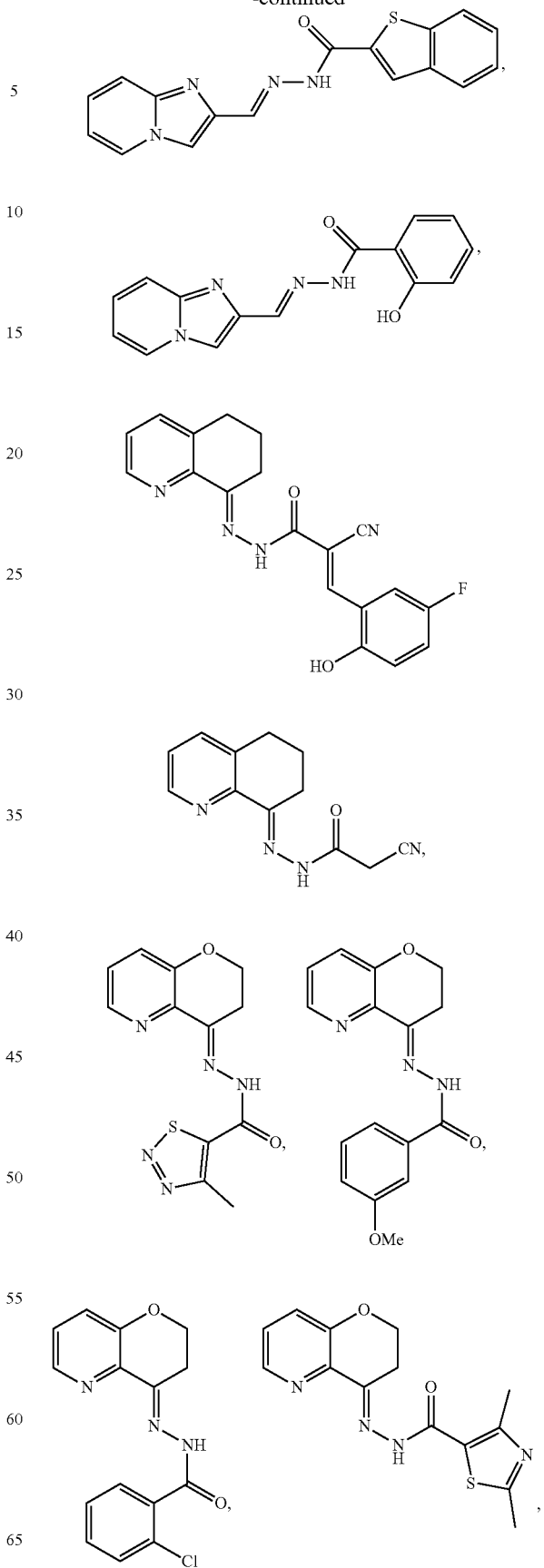

131
-continued
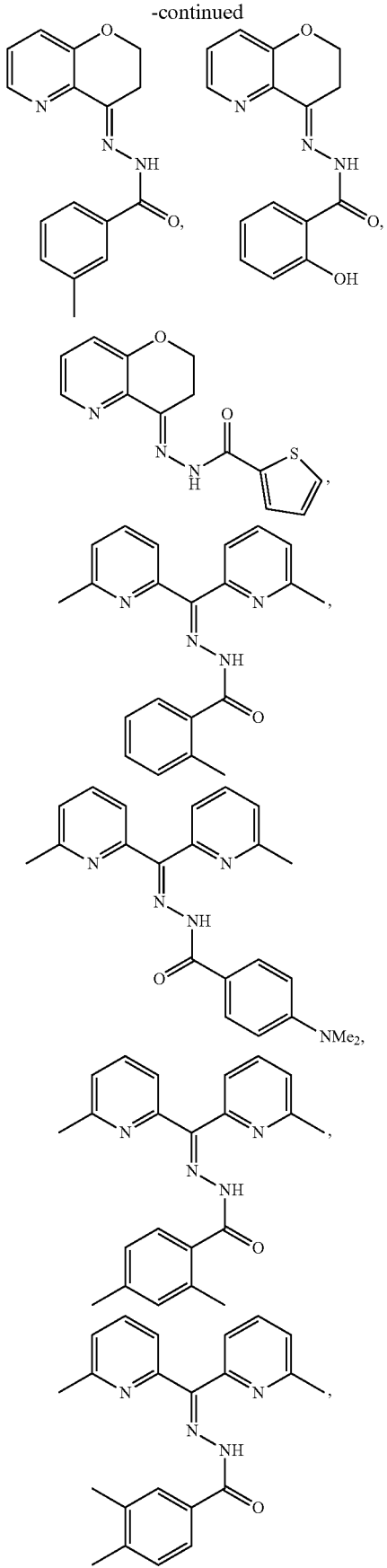
132
-continued
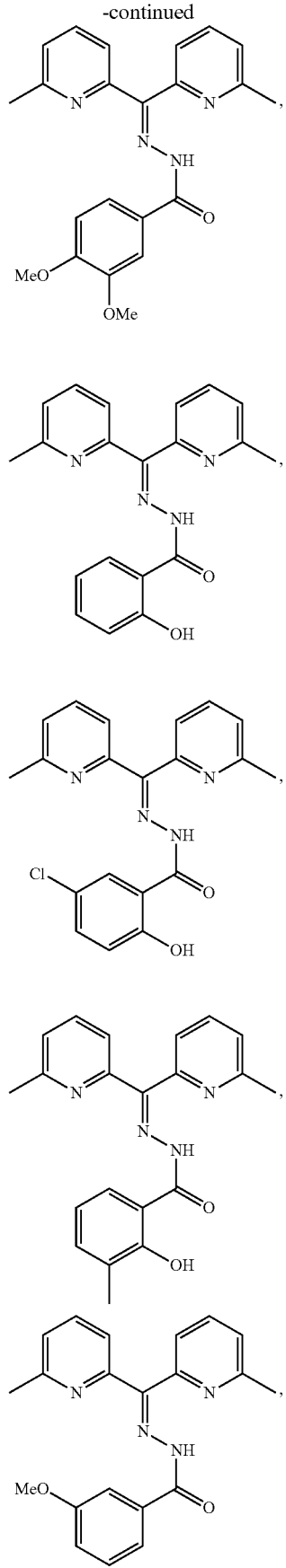

133
-continued
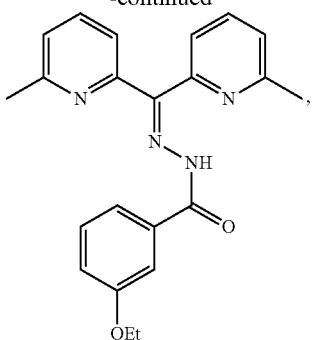
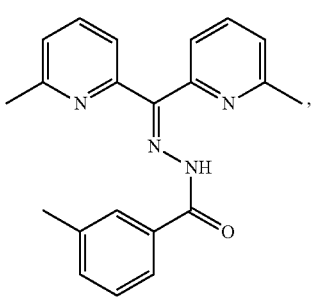
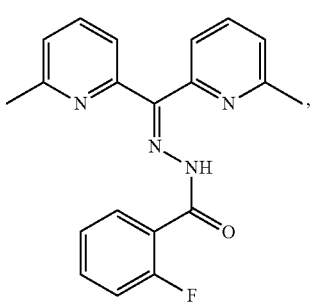
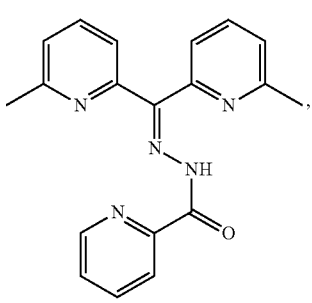
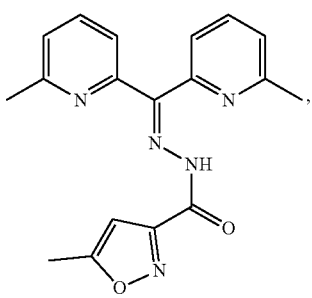
134
-continued
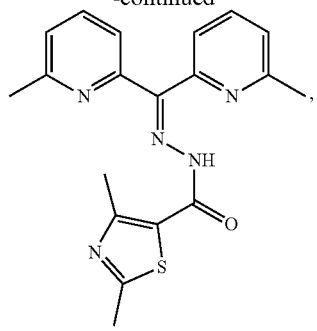
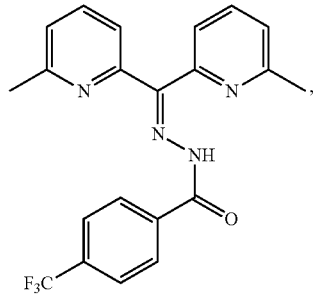
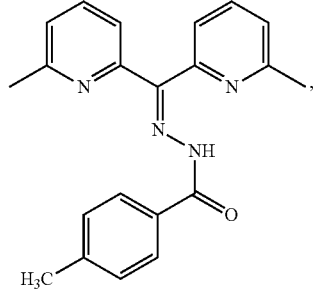
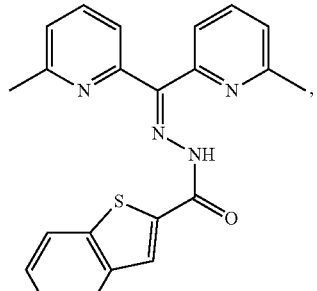
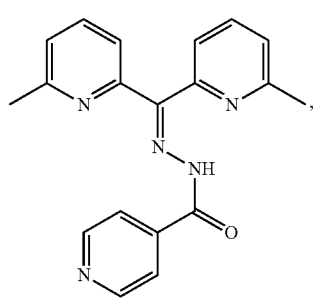

135
-continued
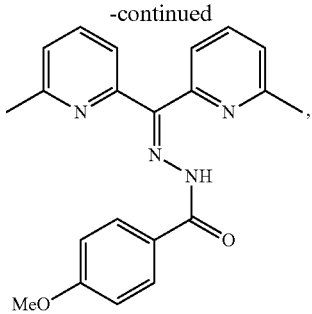
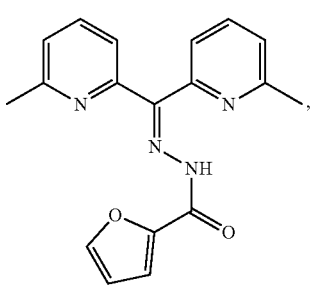
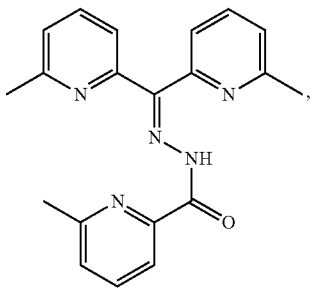
136
-continued
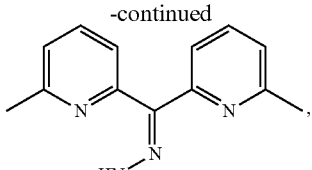
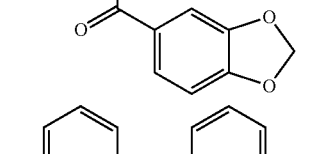
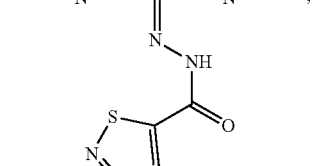
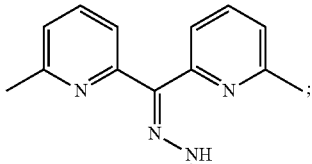
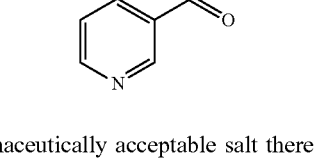
or a pharmaceutically acceptable salt thereof.
19. A pharmaceutical composition comprising a compound according to claim 1 or a pharmaceutically acceptable salt thereof and a pharmaceutically acceptable carrier.
* * * * *